US008765802B2

(12) United States Patent
Shoemaker et al.

(10) Patent No.: US 8,765,802 B2
(45) Date of Patent: Jul. 1, 2014

(54) KINASE INHIBITORS, COMPOSITIONS THEREOF, AND METHODS OF USE THEREWITH

(75) Inventors: Robert Shoemaker, Boyds, MD (US); John Cardellina, Walkersville, MD (US); Michael Currens, Frederick, MD (US); Sudhir Kondapaka, North Potomac, MD (US); Yves Pommier, Bethesda, MD (US); Andy Jobson, Rockville, MD (US); Dominic Scudiero, Frederick, MD (US); David Waugh, Walkersville, MD (US); George Lountos, Frederick, MD (US); Charles M. Cook, Mendham, NJ (US); Janet Cicariello Cook, legal representative, Mendham, NJ (US); Guangtao Zhang, Princeton, NJ (US); Andrew Colasanti, Scotch Plains, NJ (US); Christopher R. Self, West Caldwell, NJ (US)

(73) Assignees: Provid Pharmaceuticals, Inc., Monmouth Junction, NJ (US); United States of America as represented by the Department of Health and Human Resources NIH, Washington, DC (US)

( * ) Notice: Subject to any disclaimer, the term of this patent is extended or adjusted under 35 U.S.C. 154(b) by 1031 days.

(21) Appl. No.: 12/135,575

(22) Filed: Jun. 9, 2008

(65) Prior Publication Data
US 2009/0018141 A1 Jan. 15, 2009

Related U.S. Application Data

(60) Provisional application No. 60/934,375, filed on Jun. 12, 2007, provisional application No. 61/066,696, filed on Feb. 21, 2008.

(51) Int. Cl.
*A61K 31/40* (2006.01)
*C07D 209/42* (2006.01)

(52) U.S. Cl.
USPC .......................................... 514/419; 548/492

(58) Field of Classification Search
USPC .......................................... 514/419; 548/492
See application file for complete search history.

(56) References Cited

U.S. PATENT DOCUMENTS

| | | | |
|---|---|---|---|
| 2,668,178 A | 2/1954 | Behnisch et al. | |
| 3,560,557 A | 2/1971 | Thioureas et al. | |
| 3,560,566 A | 2/1971 | Thioureas et al. | |
| 3,673,241 A * | 6/1972 | Marxer | 564/27 |
| 3,955,338 A | 5/1976 | Winzeler et al. | |
| 3,980,034 A | 9/1976 | Debenham et al. | |
| 4,024,183 A * | 5/1977 | Swallow | 564/51 |
| 4,028,380 A | 6/1977 | Panneman et al. | |
| 4,289,769 A * | 9/1981 | Wright, Jr. et al. | 514/237.5 |
| 4,889,935 A * | 12/1989 | Musser | 546/176 |
| 5,599,984 A | 2/1997 | Bianchi et al. | |
| 5,750,573 A | 5/1998 | Bianchi et al. | |
| 6,172,113 B1 * | 1/2001 | Ohtani et al. | 514/562 |
| 6,951,881 B2 * | 10/2005 | Cole et al. | 514/415 |
| 2006/0204993 A1 * | 9/2006 | Li et al. | 435/6 |

FOREIGN PATENT DOCUMENTS

| | | |
|---|---|---|
| CH | 278134 | 1/1952 |
| CH | 281035 | 6/1952 |
| CH | 281036 | 6/1952 |
| CH | 281037 | 6/1952 |
| CH | 281038 | 6/1952 |
| CH | 281039 | 6/1952 |
| CH | 281040 | 6/1952 |
| CH | 496671 | 11/1970 |
| DE | 23 09 260 A1 | 2/1971 |
| DE | 10 2005 025 906 | 7/2006 |
| EP | 1 389 480 | 2/2004 |
| GB | 672370 | 5/1952 |
| GB | 1457911 | 12/1996 |
| PL | 109038 | 8/1991 |
| WO | WO 95/19767 | 7/1995 |
| WO | WO 01/56553 | 8/2001 |
| WO | WO 02/00613 | 1/2002 |
| WO | WO 03/006426 | 1/2003 |
| WO | WO 2005/039494 | 5/2005 |
| WO | WO 2007/016338 | 2/2007 |

OTHER PUBLICATIONS

Korytnyk, W. et al., "Guanylhydrazones with Potential Antileukemic Activity. 2. Synthesis and Structure-Activity Relationships of Analogues of 4,4'Diacetyl-N,N'-diphenylurea Bis(guanylhydrazone)", Journal of Medicinal Chemistry, 21(6), 507-513, 1978.*
Golub et al., Science, 286, 531-537, 1999.*
Donovick et al., Journal of Bacteriology (1950), 59, 667-74.*
Registry No. 701899-76-5, STN file registry, Jun. 30, 2004.*
Cavrini et al., Il Farmaco-Ed Sc., 35(8), pp. 636-641, 1980.*
Mitrenin et al., Voprosy Met. i Fiz. Poluprovodnikov (Moscow: Akad. Nauk S.S.S.R.) Sbornik (1957) 24-34, abstract only.*

(Continued)

*Primary Examiner* — Rebecca Anderson
(74) *Attorney, Agent, or Firm* — Jones Day

(57) ABSTRACT

Provided herein are Compounds having the following structure:

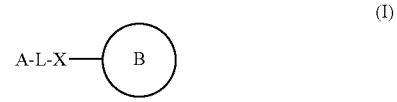

(I)

Figure 1A:
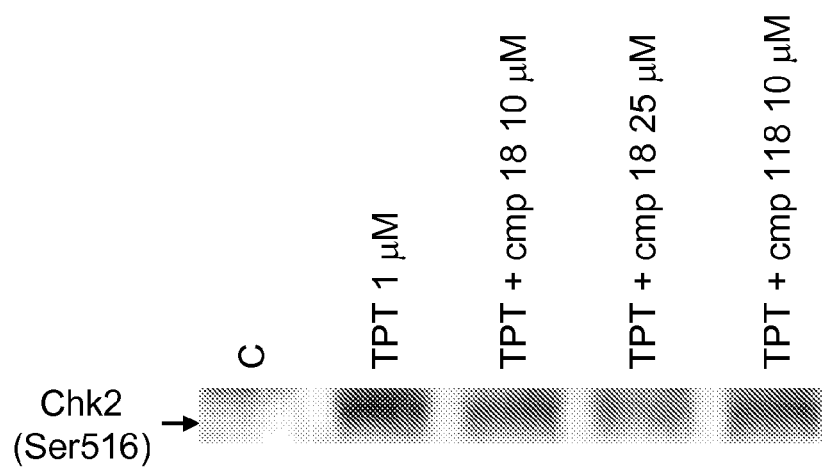

wherein A, L, X and ring B are as defined herein, compositions comprising an effective amount of a Compound and methods for treating or preventing cancer, hypoxia, diabetes, stroke, autoimmune disease or a condition treatable or preventable by inhibition of Chk2, the ATM-Chk2 pathway or RSK2 comprising administering an effective amount of a Compound to a patient in need thereof.

3 Claims, 4 Drawing Sheets

(56) References Cited

OTHER PUBLICATIONS

Registry No. 773790-66-2, STN file registry, Nov. 1, 2004.*

Antoni et al., 2007, "CHK2 kinase: cancer susceptibility and cancer therapy—two sides of the same coin?," Nature Rev Can., vol. 7:925-936.

Cho et al., 2007, "Ribosomal S6 kinase 2 is a key regulator in tumor promoter-induced cell transformation," Can Res., vol. 67(17):8104-8112.

Clark et al., 2005, "The serine/threonine protein kinase, p90 ribosomal S6 kinase, is an important regulator of prostate cancer cell proliferation," Can Res., vol. 65(8):3108-3116.

Cohen et al., 2007, "A clickable inhibitor reveals context-dependent autoactivation of p90 RSK," Nat. Chem Biol., vol. 3(3):156-160.

David et al., 2005, "Essential role of RSK2 in c-Fos-dependent osteosarcoma development," J. Clin. Invest., vol. 115(3):664-672.

Kang et al., 2007, "FGFR3 activates RSK2 to mediate hematopoietic transformation through tyrosine phosphorylation of RSK2 and activation of the MEK/ERK pathway," Cancer Cell, vol. 12(3):201-214.

Kuang et al., 2008, "Activation of p90 ribosomal S6 kinase by ORF45 of kaposi's sarcoma-associated herpesvirus and its role in viral lytic replication," J. of Virol., vol. 82(4):1838-1850.

Lin et al., 2008, "Critical role or RSK2 in T-lymphocyte activation," Blood, vol. 111(2):525-533.

Pommier et al., 2005, "Targeting Chk2 kinase: Molecular interaction maps and therapeutic rationale," Curr Pharm Design, vol. 11:2855-2872.

Sapkota et al., 2007, "BI-D1870 is a specific inhibitor of the p90 RSK (ribosomal S6 kinase) isoforms in vitro and in vivo," Biochem. J., vol. 401(1):29-38.

Denny et al., 1979, "Potential Antitumor Agents. 29. Quantitative Structure-Activity Relationships for the Antileukemic Bisquaternary Ammonium Heterocycles," J. Med. Chem, vol. 22(2):135-150.

Atwell et al., 1973, "Potential Antitumore Agents. 13. Bisquaternary Salts," J. Med. Chem., vol. 16(6):673-678.

Cain et al., 1969, "Potential Antitumore Agents. X. Bisquaternary Salts," J. Med. Chem., vol. 12(2):199-206.

* cited by examiner

KINASE INHIBITORS, COMPOSITIONS THEREOF, AND METHODS OF USE THEREWITH

This application claims the benefit of U.S. provisional application No. 60/934,375, filed Jun. 12, 2007 and U.S. provisional application No. 61/066,696, filed Feb. 21, 2008, the disclosures of which are incorporated by reference herein in their entireties.

1. STATEMENT REGARDING FEDERALLY SPONSORED RESEARCH OR DEVELOPMENT

The invention was made with United States Government support under NIH SBIR contract no. R44AI52940-2. The United States Government may have certain rights in the invention.

2. FIELD

Provided herein are certain guanidinyl hydrazone-substituted compounds and derivatives, compositions comprising such compounds and methods for treating or preventing cancer, hypoxia, diabetes, stroke, autoimmune disease or a disease, disorder or condition treatable or preventable by inhibition of Chk2, the ATM-Chk2 pathway or RSK2. comprising administering a compound disclosed herein to a patient.

3. BACKGROUND

Cellular checkpoints are molecular pathways which are activated in response to DNA damage, such as DNA double-strand breaks (DSB). Pommier et al., 2005, *Current Pharmaceutical Design* 11:2855-2872. Modulation of these checkpoints can kill damaged cells via apoptosis or arrest cell cycle progression allowing for DNA repair prior to cellular reproduction, thus preventing or slowing tumor progression. Id. The ATM-Chk2 pathway, which is primarily activated by DSB, is thought to play a key role in apoptosis and cell cycle arrest. Id. Chk2 has emerged as an important multifunctional player in the DNA-damage response signalling pathway. Antoni et al., 2007, *Nat. Rev. Can.* 7(12):925-936. Without being limited by theory, the level of intrinsic DNA damage in a given tumor cell and the degree to which Chk2 functions are essential for maintenance of the transformed phenotype of the cell can guide the use of Chk2 inhibitors against the tumor. Id. For example, when there is high intrinsic DNA damage a Chk2 inhibitor could have potential for single-agent efficacy. Id. Whereas in tumors where activated Chk2 contributes directly to the malignant phenotype or to resistance to DNA-damaging agents, a combination of a Chk2 inhibitor with a DNA-damaging agent might be more useful. Id.

Inhibitors of Chk2 kinase are set forth in International Publication No. WO 2007/016338 A2, published Feb. 8, 2007. However, in view of the key role played by Chk2 in apoptosis and cell cycle arrest, there still remains a need for pharmaceutically useful inhibitors of Chk2.

RSK2 is a serine/threonine kinase involved in cell signaling which is activated by ERK and PDK1 (Kang et al., 2007, *Cancer Cell.* 12(3):201-14). Several investigators have found evidence for a role of RSK2 in malignant transformation (Cho et al., 2007, *Cancer Res.* (17):8104-12; David et al., 2005, *J. Clin Invest.* 115(3):664-72). Clark et al. have shown a role for RSK2 in regulation of prostate cancer growth and reported a novel inhibitor as a potential therapeutic lead (Clark et al., 2005, *Cancer Res.* 65(8):3108-16). Their work provides a strong rational for targeting RSK2 in prostate cancer. In addition, RSK2 appears to be essential for certain aspect of normal lymphocyte activation (Lin et al., 2008, *Blood* 111(2):525-33). Furthermore, in view of the role of this kinase in the HHV8 lifecycle, it is conceivable that an inhibitor could have an anti-viral effect (Kuang et al., 2008, *J. Virol.* 82(4):1838-50). RSK2 inhibitors have also been described by Cohen et al. (Cohen et al., 2007, *Nat. Chem. Biol.* 3(3): 156-60) and by Sapkota et al. (Sapkota et al., 2007, *Biochem J.* 401(1):29-38). However, there still remains a need for pharmaceutically useful inhibitors of RSK2.

Citation or identification of any reference in Section 3 of this application is not to be construed as an admission that the reference is prior art to the present application.

4. SUMMARY

Provided herein are compounds having the following formula (I):

(I)

and pharmaceutically acceptable salts, solvates, hydrates, or stereoisomers thereof, wherein A, L, X and ring B are as defined herein.

Also provided herein are uses of a compound of formula (I) or a pharmaceutically acceptable salt, solvate, hydrate, or stereoisomer (each being referred to herein as a "Compound") for treating or preventing cancer, hypoxia, diabetes, stroke, autoimmune disease or a disease, disorder or condition treatable or preventable by inhibition of Chk2 or the ATM-Chk2 pathway.

Further provided herein are compositions comprising a Compound, and compositions (e.g., pharmaceutical compositions) comprising a Compound and a pharmaceutically acceptable carrier, vehicle or diluent. Also provided herein are methods of using the compositions for treating or preventing cancer, hypoxia, diabetes, stroke, autoimmune disease or a disease, disorder or condition treatable or preventable by inhibition of Chk2 or the ATM-Chk2 pathway.

Further provided herein are methods for treating or preventing cancer, hypoxia, diabetes, stroke, autoimmune disease or a disease, disorder or condition treatable or preventable by inhibition of Chk2 or the ATM-Chk2 pathway comprising administering a Compound to a patient in need of the treating or preventing.

Further provided herein are methods for treating or preventing a disease, disorder or condition treatable or preventable by inhibition of RSK2 or the RSK2 pathway comprising administering a Compound to a patient in need of the treating or preventing.

Further provided herein are methods for identifying a patient in need of administration of a Compound by determining the level of a biological marker and administering a Compound to the patient.

Further provided herein are methods for inhibiting Chk2 or the ATM-Chk2 pathway in a cell comprising contacting said cell with a Compound.

Further provided herein are methods for inhibiting RSK2 or the RSK2 pathway in a cell comprising contacting said cell with a Compound.

Further provided herein are methods for inhibiting Chk2 or the ATM-Chk2 pathway in tissue comprising contacting said tissue with a Compound.

Further provided herein are methods for inhibiting RSK2 or the RSK2 pathway in tissue comprising contacting said tissue with a Compound.

Further provided herein are methods for protecting normal (in one embodiment, healthy) tissue in a patient, comprising identifying a patient having tissue in need of such protection and administering to the patient an amount of a Compound effective to protect normal tissue. In a particular embodiment, the tissue is protected from becoming cancerous or metastases are reduced or avoided.

Further provided herein are methods for preventing or reducing apopstosis in a normal cell in a patient, comprising identifying a patient having one or more cells in need of such prevention or reduction and administering to the patient an amount of a Compound effective to prevent or reduce apoptosis in a normal cell.

Further provided herein are methods for sensitizing a tumor, a cancer cell or cancerous tissue to an anticancer agent, anticancer treatment or a DNA targeted agent, comprising administering a patient who has cancer or a tumor an amount of a Compound effective to sensitize the cancer or tumor to an anticancer agent, anticancer treatment or a DNA targeted agent. In one embodiment, the Compounds and the anticancer agent, anticancer treatment or a DNA targeted agent are administered in combination (e.g., sequentially or simultaneously). In a particular embodiment, the Compounds and the anticancer agent, anticancer treatment or a DNA targeted agent provide a synergistic effect when administered in combination to a patient.

Further provided herein are methods for modulating a substrate in a normal (in one embodiment, healthy) cell in a patient, comprising identifying a patient having one or more cells in need of such modulation and administering to the patient an amount of a Compound effective to modulate the substrate in a normal cell.

Further provided herein are methods for modulating a protein in a patient, comprising identifying a patient in need of such modulation and administering to the patient an amount of a Compound effective to modulate the protein.

Further provided herein are methods for modulating Chk2 phosphorylation in a patient (e.g., in a patient's cell(s)), comprising administering to the patient an amount of a Compound effective to modulate Chk2 phosphorylation. In a particular embodiment, Chk2 phosphorylation is inhibited or down-regulated. In another embodiment, a patient is identified as being in need of such modulation through a screening assay prior to such administration.

In one embodiment, the Compound targets two or more of the following: kinases from the Chk kinase family, kinases from the MEK kinase family, kinases from the src kinase family, kinases from the RSK kinase family (e.g., RSK2), kinases from the CDK family, kinases from the MAPK kinase family, and tyrosine kinases such as Fes, Lyn, and Syk kinases. The Compound may target two or more kinases of the same family, or may target kinases representing two or more kinase families or classes. The Compound may also target kinases with differing potencies. In other words, without being limited by any theory, a Compound, or composition thereof, may have multi-kinase activity and thus can treat or prevent one or more diseases, disorders or conditions based upon their kinase modulation profile.

In one embodiment, the Compound is selective for Chk2 over Chk1.

The present embodiments can be understood more fully by reference to the detailed description and examples, which are intended to exemplify non-limiting embodiments.

5. DETAILED DESCRIPTION

5.1 Brief Description of the Drawings

Without being limited by theory, particularly useful Compounds include those which can abrogate DNA damage-induced Chk2 autophosphorylation on S516, abrogate DNA damage-induced HDMX degradation, abrogate Chk2-mediated IR-induced apoptosis in mouse thymocytes and provide or promote synergism of DNA damaging agents in human cancer cells. The figures set forth herein provide direct and indirect measurements of Chk2 inhibition and provide such functional endpoints for Compounds.

Figure 1B:
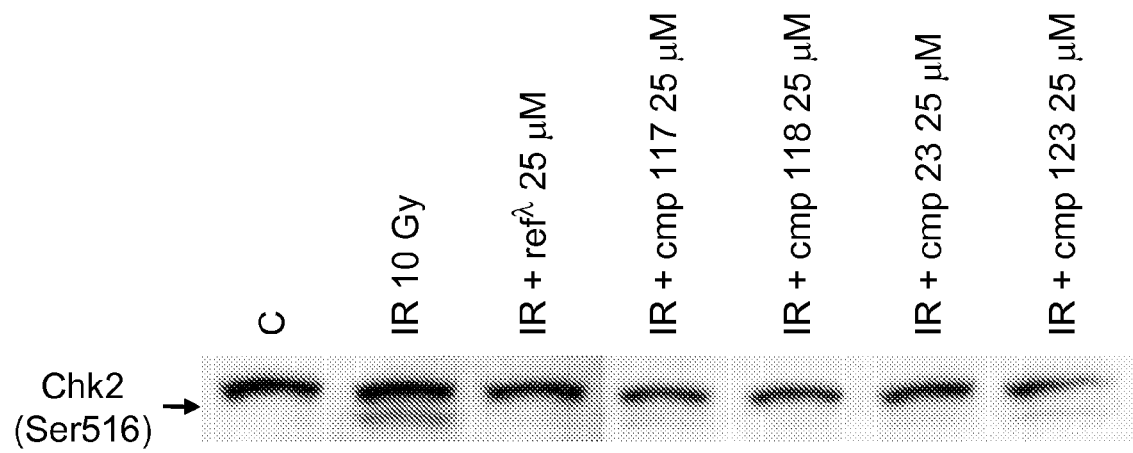

FIG. 1. Effect of Compounds on the Chk2 autophosphorylation residue S516 following DNA damage in HT29 cells. A HT29 cells were treated with compound 18 (10 and 25 µM) or compound 118 (10 µM) for 1 hour. Following this, 1 µM topotecan (TPT) was added for a further hour. Nuclear extracts were made from the cells and Western blotting for Chk2 S516 was performed. B HT29 cells were treated with Compounds (25 µM) for 1 hour. Following this the cells were exposed to 10 Gy IR and incubated for a further hour. Whole cell extracts were made and Western blotting for Chk2 S516 was performed. Asterisks indicate non-specific band running slightly slower than Chk2 S516. This data demonstrates that Compounds are useful for the treatment of cancer, either alone or in combination with other anti-cancer agents or therapies (e.g., chemotherapy or radiation therapy).

Figure 2:
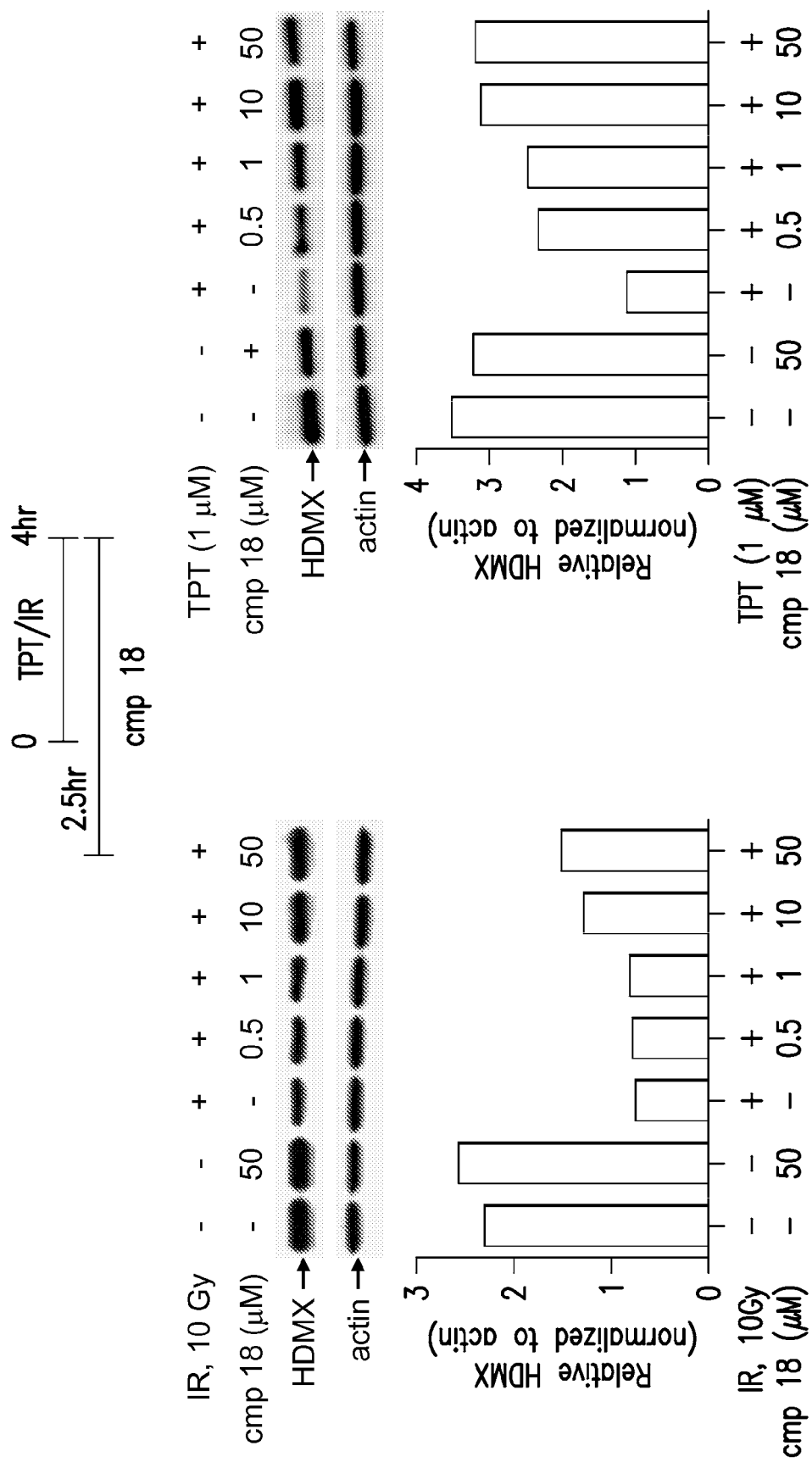

FIG. 2. Abrogation of HDMX degradation by compound 18 in MCF7 cells following DNA damage. MCF7 cells were treated in the absence (control) or presence of compound 18 at varying concentrations for 2.5 hours. The cells were then exposed to either 1 µM topotecan (TPT) for 4 hours or they were exposed to 10 Gy IR and incubated for 4 hours. Whole cell extracts were made and Western blotting was performed to detect HDMX. The levels of HDMX were quantified from the blots and normalized to actin. The normalized levels of HDMX are depicted as bar graphs under the blots. This data demonstrates that Compounds are useful for the treatment of cancer, either alone or in combination with other anti-cancer agents or therapies.

Figure 3:
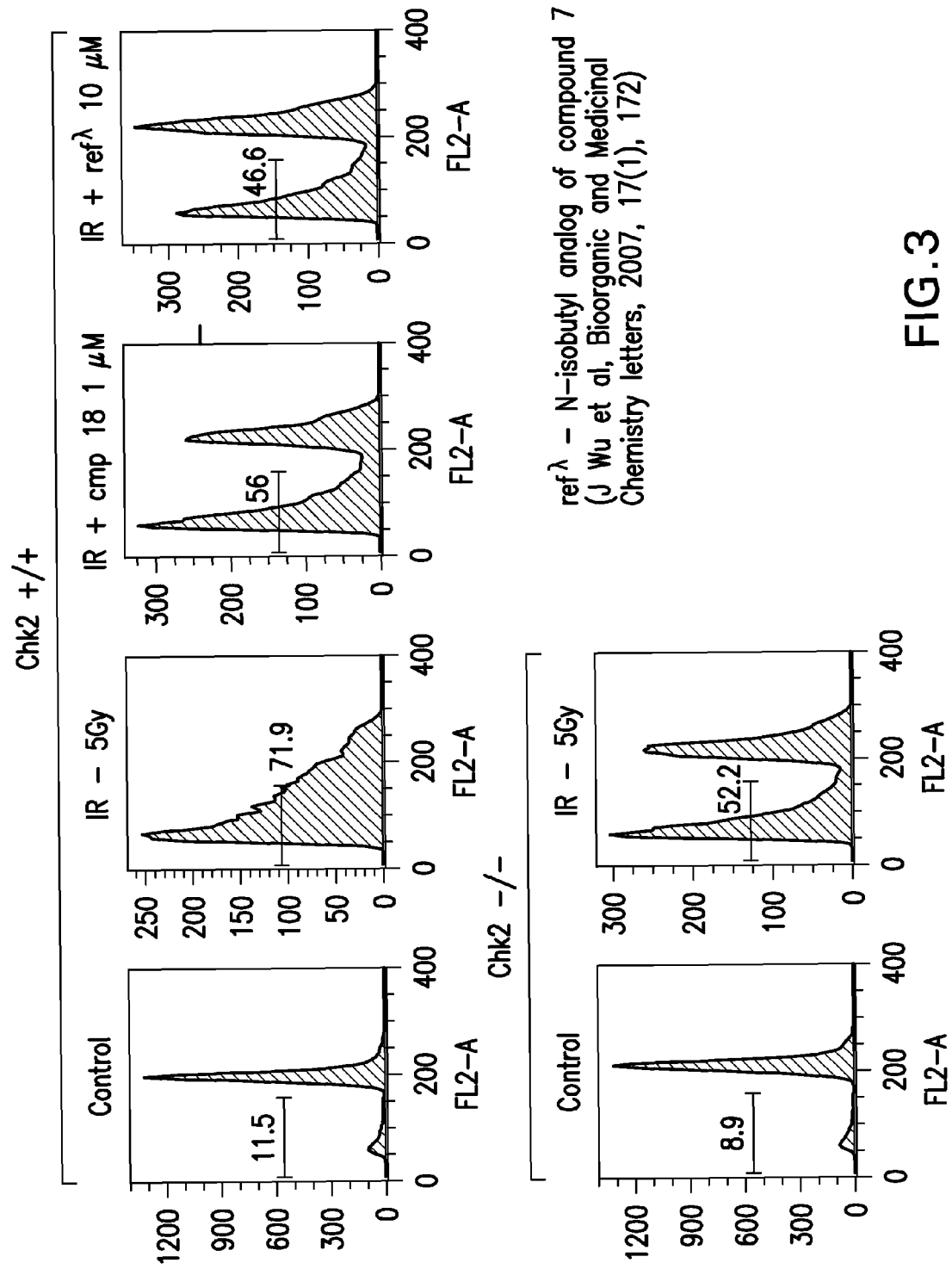

FIG. 3. Compound 18-mediated abrogation of IR-induced apoptosis in mouse thymocytes. Thymocytes were isolated from Chk2+/+ or Chk2−/− mice by mechanical disaggregation. The isolated thymocytes were treated in the absence or presence of 1 µM compound 18 or ref$^\lambda$ (J. Wu et al, Bioorganic and Medicinal Chemistry letters, 2007, 17(1), 172, [N-isobutyl analog of compound 7]) for 1 hour. The cells were then exposed to 5 Gy IR and incubated for 16 hours. The cells were then washed in PBS and fixed in ethanol. Propidium isodide (PI) was added in the presence of RNAse A before being subjected to flow cytometry. The graphs show FACS analysis of the PI stained cells. This data demonstrates that Compounds are useful for the treatment of cancer, either alone or in combination with other anti-cancer agents or therapies.

Figure 4:
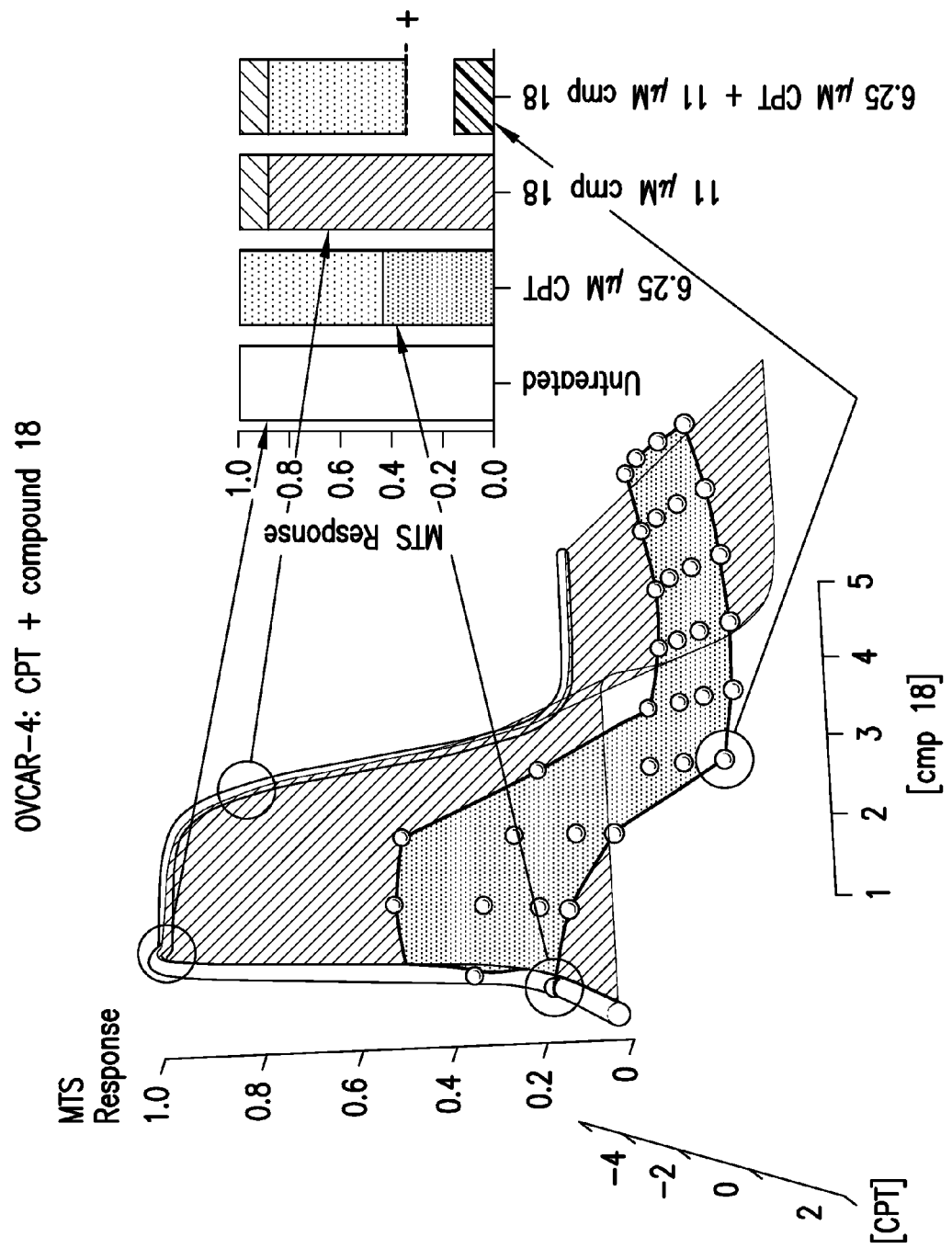

FIG. 4. Compound 18 is synergistic with camptothecin (CPT) in OVCAR-4 cells. OVCAR-4 cells were treated with either compound 18 or CPT as single agents in 96 well tissue culture plates. In addition, the cells were exposed to 40 combinations of compound 18 and CPT. The drug treatments were for 48 hours and the cells were then subjected to MTS staining to determine the growth inhibitory effect. The graph represents a 3-dimensional plot of the MTS data obtained. The upper, light gray surface represents a theoretical surface of additivity that was generated from dose response curves of compound 18 alone and CPT alone. The lower, dark grey surface depicts the surface of the combination of compound 18 and CPT that was generated from data obtained in the MTS assay (shown by the blue circles). Data points lying under the green additivity surface are deemed to synergistic combinations. The bar graph on the right is a 2-dimensional representation of 1 combination of 11 μM compound 18 and 6.25 μM CPT taken from the 3-D model. This data demonstrates that Compounds are useful for the treatment of cancer, either alone or in combination with other anti-cancer agents or therapies.

5.2 Definitions

A "$C_{1-6}$alkyl" group is a saturated straight chain or branched non-cyclic hydrocarbon having from 1 to 6 carbon atoms. Representative $C_{1-6}$alkyl groups or radicals include -methyl, -ethyl, -n-propyl, -n-butyl, -n-pentyl, -n-hexyl; -isopropyl, -sec-butyl, -isobutyl, -tert-butyl, -isopentyl, 2-methylpentyl, 3-methylpentyl, 4-methylpentyl, 2,3-dimethylbutyl and the like. A $C_{1-6}$alkyl group can be substituted or unsubstituted.

A "$C_{1-6}$alkylene" group is a saturated straight chain or branched non-cyclic hydrocarbon linker having from 1 to 6 carbon atoms. $C_{1-6}$alkylene groups include, but are not limited to, —$CH_2$—, —$(CH_2)_2$—, —$(CH_2)_3$—, —$(CH_2)_4$—, —$(CH_2)_5$— and —$(CH_2)_6$—. A $C_{1-6}$alkylene group can be substituted or unsubstituted.

A "$C_{3-10}$cycloalkyl" group is a cyclic alkyl group of from 3 to 10 carbon atoms having a single cyclic ring or multiple condensed or bridged rings which can be unsubstituted or substituted with from 1 to 3 alkyl groups. Such $C_{3-10}$cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantanyl and the like. A $C_{3-10}$cycloalkyl group can be substituted or unsubstituted. Such substituted $C_{3-10}$cycloalkyl groups include, by way of example, cyclohexanone and the like.

A "5- or 6-membered cycloalkenyl" ring is an unsaturated cyclic alkenyl group of from 5 to 6 carbon atoms having one or more double bonds. Such groups include, by way of example, cyclopentene, cyclohexene, and the like. The double bond can be shared with an aryl (e.g., phenyl) group when the 5- or 6-membered cycloalkenyl ring is fused to an aryl (e.g., phenyl) group. A 5- or 6-membered cycloalkenyl ring can be substituted or unsubstituted.

A "carboxyl" or "carboxy" is a —COOH group.

A "halogen" is fluorine, chlorine, bromine or iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, benzyl, biphenyl, naphthyl, 2,3-dihydro-1H-indene, 1,2,3,4-tetrahydronaphthalene and the like. An aryl group can be substituted or unsubstituted.

A "$C_{3-10}$heteroaryl" group is an aryl ring system having one to four heteroatoms as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include aromatic groups selected from the following:

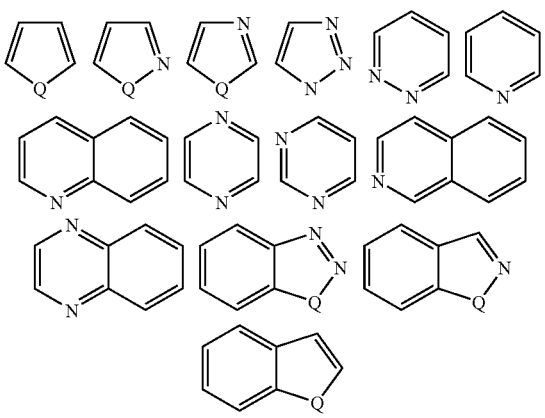

wherein Q, where appropriate, is $CH_2$, CH=CH, O, S or NH. Further representative examples of $C_{3-10}$heteroaryl groups include, but are not limited to, benzofuranyl, benzothienyl, indolyl, benzopyrazolyl, coumarinyl, furanyl, isothiazolyl, imidazolyl, isoxazolyl, thiazolyl, triazolyl, tetrazolyl, thiophenyl, pyrimidinyl, isoquinolinyl, quinolinyl, pyridinyl, pyrrolyl, pyrazolyl, 1H-indolyl, 1H-indazolyl, benzo[d]thiazolyl, 1H-benzo[d]imidazole and pyrazinyl. $C_{3-10}$heteroaryls can be bonded at any ring atom (i.e., at any carbon atom or heteroatom of the $C_{3-10}$heteroaryl ring) A $C_{3-10}$heteroaryl group can be substituted or unsubstituted.

A "$C_{3-10}$heterocycloalkyl" group is a non-aromatic cycloalkyl in which one to four of the ring carbon atoms are independently replaced with a heteroatom from the group consisting of O, S and N. Representative examples of $C_{3-10}$heterocycloalkyl groups include, but are not limited to, morpholinyl, pyrrolidinyl, piperizinyl, (1,4)-dioxane, (1,3)-dioxolane, and 4,5-dihydro-1H-imidazolyl. $C_{3-10}$heterocycloalkyls can be bonded at any ring atom (i.e., at any carbon atom or heteroatom of the $C_{3-10}$heterocycloalkyl ring). A $C_{3-10}$heterocycloalkyl group can be substituted or unsubstituted.

In one embodiment, when the groups described herein are said to be "substituted," they may be substituted with any suitable substituent. Illustrative examples of substituents are those found in the exemplary compounds and embodiments disclosed herein, as well as halogen (chloro, iodo, bromo, or fluoro); $C_{1-6}$alkyl; $C_{2-6}$alkenyl; $C_{2-6}$alkynyl; hydroxyl; $C_{1-6}$alkoxyl; amino; nitro; thiol; thioether; imine; cyano; amido; carbamate; phosphonato; phosphine; carboxyl; thiocarbonyl; sulfonyl; sulfonamide; ketone; aldehyde; ester; oxygen (=O); haloalkyl (e.g., trifluoromethyl); $B(OH)_2$, carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

As used herein, the term "pharmaceutically acceptable salt(s)" refers to a salt prepared from a pharmaceutically acceptable non-toxic acid or base including an inorganic acid and base and an organic acid and base. When a Compound contains an acidic or basic moiety, it can be provided as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, alpha-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

As used herein and unless otherwise indicated, the term "hydrate" means a Compound, or a salt thereof, that further includes a stoichiometric or non-stoichiometric amount of water bound by non-covalent intermolecular forces.

As used herein and unless otherwise indicated, the term "solvate" means an a Compound, or a salt thereof, that further includes a stoichiometric or non-stoichiometric amount of a solvent bound by non-covalent intermolecular forces.

As used herein and unless otherwise indicated, the term "stereoisomer" or "stereomerically pure" means one stereoisomer of a Compound that is substantially free of other stereoisomers of that compound. In certain embodiments, the stereoisomer is an enantiomer or diastereomer. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Compounds can have chiral centers and can occur as racemates, individual enantiomers or diastereomers, and mixtures thereof. All such isomeric forms are included within the embodiments disclosed herein, including mixtures thereof.

Various Compounds contain one or more chiral centers, and can exist as racemic mixtures of enantiomers, mixtures of diastereomers or enantiomerically or optically pure compounds. The use of stereomerically pure forms of such Compounds, as well as the use of mixtures of those forms are encompassed by the embodiments disclosed herein. For example, mixtures comprising equal or unequal amounts of the enantiomers of a particular Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Compounds can include E and Z isomers, or a mixture thereof, and cis and trans isomers or a mixture thereof. In certain embodiments, the Compounds are isolated as either the E or Z isomer. In other embodiments, the Compounds are a mixture of the E and Z isomers. Compounds encompassed by the formulas set forth herein and Compounds specifically set forth herein (structurally and/or by name) are intended to represent all E/Z stereoisomers. For example, a compound containing two double bonds capable of having E/Z stereochemistry whose structure is depicted with both double bonds having E stereochemistry is intended to include compounds with E/E, E/Z, Z/E and Z/Z stereochemistry.

It should further be noted that the Compounds can exist in different tautomeric forms or in an equilibrium between tautomeric forms. Compounds encompassed by the formulas set forth herein and Compounds specifically set forth herein (structurally and/or by name) are intended to represent all tautomeric forms or a mixture of possible tautomeric forms. For example, the structure

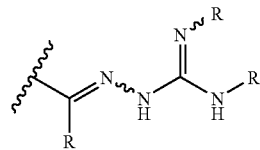

includes the tautomer

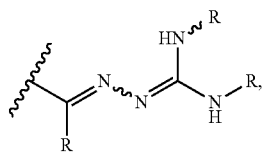

and the structure

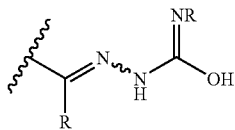

includes the tautomer

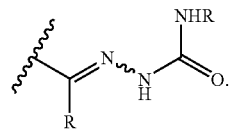

The term "effective amount" in connection with a Compound can mean an amount capable of treating or preventing a disease disclosed herein, such as cancer, a precancerous lesion, hypoxia, diabetes, stroke, autoimmune disease or a condition treatable or preventable by inhibition of Chk2, the ATM-Chk2 pathway or RSK2.

The term "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In a particular embodiment, the patient is an animal, such as a human, in need of the treatment or prevention of cancer, hypoxia, diabetes, stroke, autoimmune disease or a disease, disorder or condition treatable or preventable by inhibition of Chk2, the ATM-Chk2 pathway or RSK2.

5.3 Compounds

Provided herein are Compounds having the formula (I):

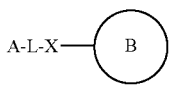

(I)

and pharmaceutically acceptable salts, solvates, hydrates and stereoisomers thereof, wherein:
ring B is

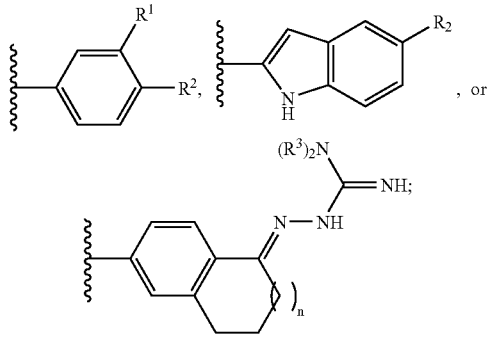, or

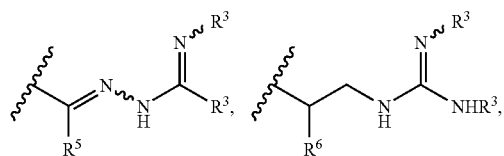

n is an integer selected from 0 and 1;
$R^1$ is H;
$R^2$ is —C(O)H, —C(O)C$_{1-6}$alkyl, —OC$_{1-6}$alkyl or a group selected from:

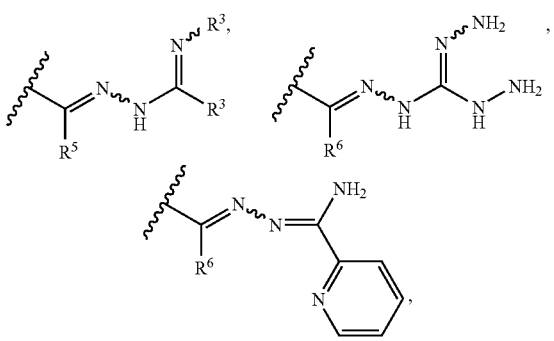

or $R^1$ and $R^2$ taken together with the atoms to which they are attached form a substituted or unsubstituted 5- or 6-membered cycloalkenyl ring; or $R^1$ and either $R^5$ or $R^6$ taken together with the atoms to which they are attached form a substituted or unsubstituted 5- or 6-membered cycloalkenyl ring;

X is —N($R^4$)—C(O)—N($R^4$)—, —C(O)—N($R^4$)—, —N($R^4$)—C(O)—, —N($R^4$)—N($R^4$)—C(O)—, —C(O)—N($R^4$)—N($R^4$)—, —C(O)—, —NH—SO$_2$—NH—, —NHSO$_2$— or —SO$_2$NH—;

L is a direct bond or C$_{1-6}$alkylene;

A is substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl;

$R^3$ is at each occurrence independently H, —OH, —OC$_{1-6}$alkyl, —NH$_2$, —NHOH, —NHR$^6$, —SH or —S—C$_{1-6}$alkyl; and $R^4$, $R^5$ and $R^6$ are at each occurrence independently H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl, wherein either A is substituted with at least one of the following groups or $R^2$ is one of the following groups:

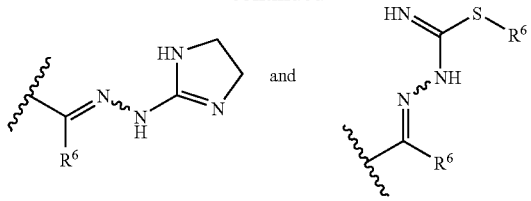 and 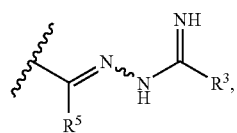

In one embodiment, the Compounds of formula (I) are those wherein ring B is

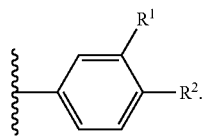

In another embodiment, the Compounds of formula (I) are those wherein ring B is

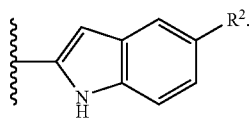

In another embodiment, the Compounds of formula (I) are those wherein A is aryl substituted with one or more substituents other than $C_{1-6}$alkyl, halo or alkoxy, substituted or unsubstituted $C_{3-10}$heteroaryl, substituted $C_{3-10}$cycloalkyl, substituted or unsubstituted $C_{3-10}$heterocycloalkyl, or substituted $C_{1-6}$alkyl.

In another embodiment, the Compounds of formula (I) are those wherein A is: phenyl substituted with halogen, $C_{1-6}$alkyl, C(O)$C_{1-6}$alkyl, CN, urea (e.g., —NH—C(=O)—NH—) or pyrimidine; unsubstituted $C_{3-10}$heteroaryl; $C_{3-10}$heteroaryl substituted with NH$_2$, NO$_2$, OH, halogen, $C_{1-6}$alkyl, alkoxy, carbamate or hydrazino guanidine (e.g., —CH(CH$_3$)=N—NH—CH(=NH)—NH$_2$); unsubstituted heterocycloalkyl; unsubstituted naphthyl; or naphthyl substituted with guanidine.

In another embodiment, the Compounds of formula (I) are those wherein A is substituted aryl, wherein the aryl group has 2-5 substituents (e.g., 2-5 substituents selected from substituents set forth herein).

In another embodiment, the Compounds of formula (I) are those wherein A is substituted or unsubstituted 1H-indole, substituted or unsubstituted 1H-indazole, substituted or unsubstituted benzofuran or substituted or unsubstituted benzo[d]thiazole.

In another embodiment, the Compounds of formula (I) are those wherein $R^1$ is H.

In another embodiment, the Compounds of formula (I) are those wherein $R^2$ is

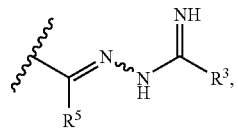

wherein $R^3$ and $R^5$ are as described above.

In another embodiment, the Compounds of formula (I) are those wherein $R^2$ is —C(CH$_3$)=N—NH—C(=NH)—NH$_2$ (E/Z or cis/trans).

In another embodiment, the Compounds of formula (I) are those wherein $R^2$ is H and $R^2$ is

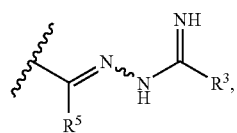

wherein $R^3$ and $R^5$ are as described above.

In another embodiment, the Compounds of formula (I) are those wherein X is —N(R$^4$)—C(O)—N(R$^4$)—, wherein R$^4$ is as described above.

In another embodiment, the Compounds of formula (I) are those wherein X is —C(O)—N(R$^4$)— or —N(R$^4$)—C(O)—, wherein R$^4$ is as described above.

In another embodiment, the Compounds of formula (I) are those wherein L is a direct bond.

In another embodiment, the Compounds of formula (I) are those wherein X is —N(R$^4$)—C(O)—N(R$^4$)— and L is a direct bond, wherein R$^4$ is as described above.

In another embodiment, the Compounds of formula (I) are those wherein $R^3$ is —NH$_2$.

In another embodiment, the Compounds of formula (I) are those wherein $R^5$ is H, substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{3-6}$alkyl.

In another embodiment, the Compounds of formula (I) are those wherein $R^5$ is $C_{1-6}$alkyl.

In another embodiment, the Compounds of formula (I) are those wherein $R^4$ is H.

In another embodiment, the Compounds of formula (I) are those wherein A is substituted aryl.

In another embodiment, the Compounds of formula (I) are those wherein A is substituted or unsubstituted $C_{3-10}$heteroaryl.

In another embodiment, the Compounds of formula (I) are those wherein A is aryl or $C_{3-10}$heteroaryl substituted with

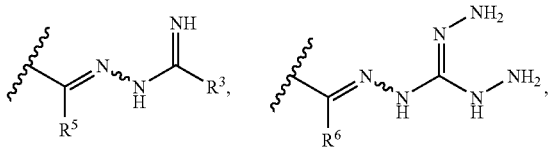

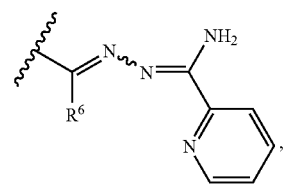

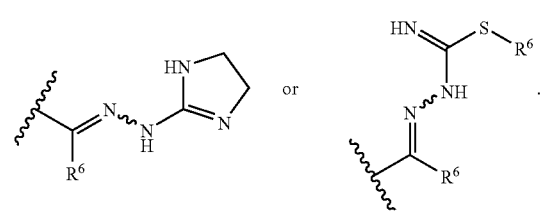

In a further embodiment, provided herein are Compounds of formula (II):

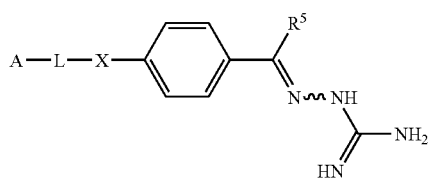

and pharmaceutically acceptable salts, solvates, hydrates and stereoisomers thereof, wherein:

X is —N(R$^4$)—C(O)—N(R$^4$)—, —C(O)—N(R$^4$)—, —N(R$^4$)—C(O)—, —N(R$^4$)—N(R$^4$)—C(O)—, —C(O)—N(R$^4$)—N(R$^4$)—, —C(O)—, —NH—SO$_2$—NH—, —NHSO$_2$— or —SO$_2$NH—;

L is a direct bond or C$_{1-6}$alkylene;

A is substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl; and R$^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl In one embodiment, the Compounds of formula (II) are those wherein A is aryl substituted with one or more substituents other than C$_{1-6}$alkyl, halo or alkoxy, substituted or unsubstituted C$_{3-10}$heteroaryl, substituted C$_{3-10}$cycloalkyl, substituted or unsubstituted C$_{3-10}$heterocycloalkyl, or substituted C$_{1-6}$alkyl.

In another embodiment, the Compounds of formula (II) are those wherein A is: phenyl substituted with halogen, C$_{1-6}$alkyl, C(O)C$_{1-6}$alkyl, CN, urea or pyrimidine; unsubstituted C$_{3-10}$heteroaryl; C$_{3-10}$heteroaryl substituted with NH$_2$, NO$_2$, OH, halogen, C$_{1-6}$alkyl, alkoxy, carbamate or hydrazino guanidine (e.g., —CH(CH$_3$)=N—NH—CH (=NH)—NH$_2$ (E/Z or cis/trans)); unsubstituted heterocycloalkyl; unsubstituted naphthyl; or naphthyl substituted with guanidine.

In another embodiment, the Compounds of formula (II) are those wherein A is substituted aryl, wherein the aryl group has 2-5 substituents (e.g., 2-5 substituents selected from substituents set forth herein).

In another embodiment, the Compounds of formula (II) are those wherein A is substituted or unsubstituted 1H-indole, substituted or unsubstituted 1H-indazole, substituted or unsubstituted benzofuran or substituted or unsubstituted benzo[d]thiazole.

In another embodiment, the Compounds of formula (II) are those wherein R$^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{3-6}$alkyl.

In another embodiment, the Compounds of formula (II) are those wherein R$^5$ is C$_{1-6}$alkyl.

In another embodiment, the Compounds of formula (II) are those wherein R$^5$ is H.

In another embodiment, the Compounds of formula (II) are those wherein A is substituted aryl.

In another embodiment, the Compounds of formula (II) are those wherein A is substituted or unsubstituted C$_{3-10}$heteroaryl.

In another embodiment, the Compounds of formula (II) are those wherein X is —N(R$^4$)—C(O)—N(R$^4$)—, wherein R$^4$ is as described above.

In another embodiment, the Compounds of formula (II) are those wherein X is —C(O)—N(R$^4$)— or —N(R$^4$)—C(O)—, wherein R$^4$ is as described above.

In another embodiment, the Compounds of formula (II) are those wherein R$^5$ is C$_{1-6}$alkyl and A is substituted aryl.

In another embodiment, the Compounds of formula (II) are those wherein A is aryl or C$_{3-10}$heteroaryl substituted with

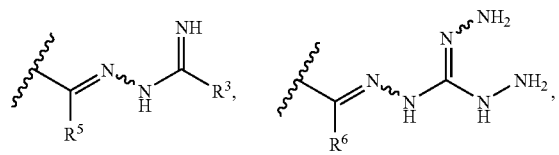

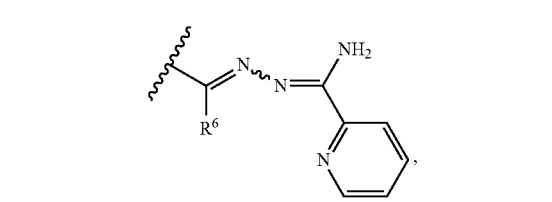

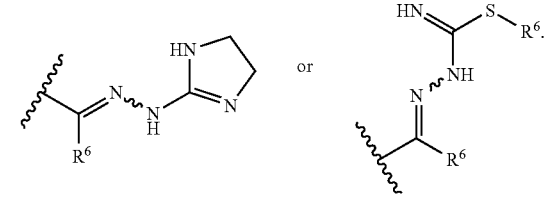

In a further embodiment, provided herein are Compounds of formula (III):

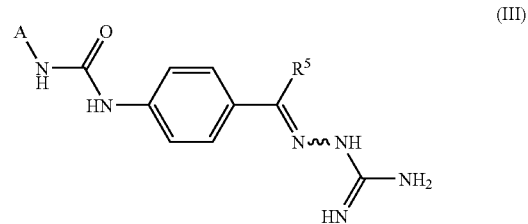

and pharmaceutically acceptable salts, solvates, hydrates and stereoisomers thereof, wherein:

A is substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl; and R$^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl.

In one embodiment, the Compounds of formula (III) are those wherein A is aryl substituted with one or more substituents other than $C_{1-6}$alkyl, halo or alkoxy, substituted or unsubstituted $C_{3-10}$heteroaryl, substituted $C_{3-10}$cycloalkyl, substituted or unsubstituted $C_{3-10}$heterocycloalkyl, or substituted $C_{1-6}$alkyl.

In another embodiment, the Compounds of formula (III) are those wherein A is: phenyl substituted with halogen, $C_{1-6}$alkyl, $C(O)C_{1-6}$alkyl, CN, urea or pyrimidine; unsubstituted $C_{3-10}$heteroaryl; $C_{3-10}$heteroaryl substituted with $NH_2$, $NO_2$, OH, halogen, $C_{1-6}$alkyl, alkoxy, carbamate or hydrazino guanidine (e.g., —CH(CH$_3$)=N—NH—CH(=NH)—NH$_2$ (E/Z or cis/trans)); unsubstituted heterocycloalkyl; unsubstituted naphthyl; or naphthyl substituted with guanidine.

In another embodiment, the Compounds of formula (III) are those wherein A is substituted aryl, wherein the aryl group has 2-5 substituents (e.g., 2-5 substituents selected from substituents set forth herein).

In another embodiment, the Compounds of formula (III) are those wherein A is substituted or unsubstituted 1H-indole, substituted or unsubstituted 1H-indazole, substituted or unsubstituted benzofuran or substituted or unsubstituted benzo[d]thiazole.

In another embodiment, the Compounds of formula (III) are those wherein $R^5$ is H, substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{3-6}$alkyl.

In another embodiment, the Compounds of formula (III) are those wherein $R^5$ is $C_{1-6}$alkyl.

In another embodiment, the Compounds of formula (III) are those wherein $R^5$ is H.

In another embodiment, the Compounds of formula (III) are those wherein A is substituted aryl.

In another embodiment, the Compounds of formula (III) are those wherein A is substituted or unsubstituted $C_{3-10}$heteroaryl.

In another embodiment, the Compounds of formula (III) are those wherein $R^5$ is $C_{1-6}$alkyl and A is substituted aryl.

In another embodiment, the Compounds of formula (III) are those wherein A is aryl or $C_{3-10}$heteroaryl substituted with

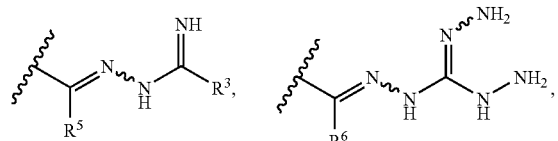

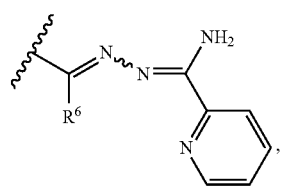

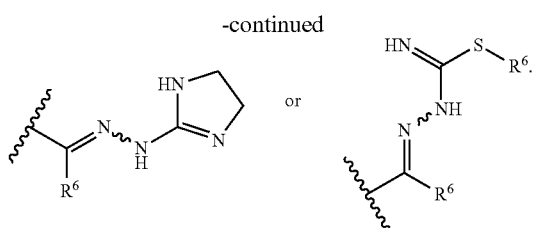

In another embodiment, the Compounds of formulas (I)-(III) do not include compounds wherein L is a direct bond, X is —N($R^4$)—C(O)—N($R^4$)—, $R^2$ is

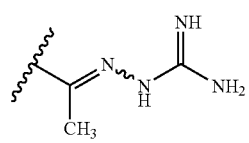 [SMILES: *C(C)=NNC(=N)N]

or

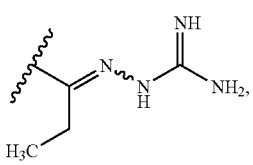

and A is phenyl monosubstituted in the para position with

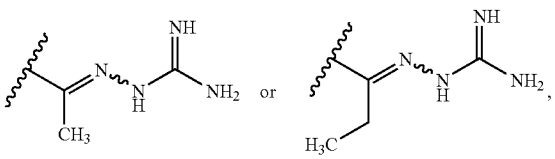

wherein $R^4$ is as described above.

In another embodiment, the Compounds of formulas (I)-(III) do not include compounds wherein L is a direct bond, X is —N($R^4$)—C(O)—N($R^4$)—, $R^2$ is

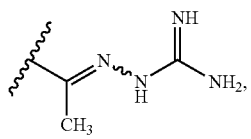

and A is phenyl disubstituted in the ortho and meta positions with

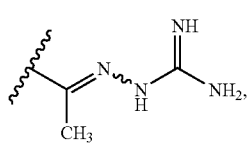

wherein $R^4$ is as described above.

In another embodiment, the Compounds of formulas (I)-(III) do not include compounds wherein L is a direct bond, X is —N(R⁴)—C(O)—N(R⁴)—, R² is

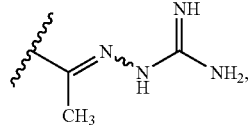

and A is phenyl monosubstituted in the meta position with

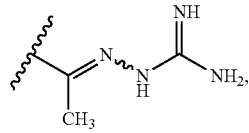

wherein R⁴ is as described above.

In another embodiment, the Compounds of formulas (I)-(III) do not include compounds wherein L is a direct bond, X is —N(R⁴)—C(O)—N(R⁴)—, R² is

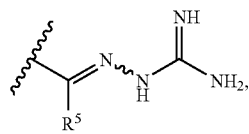

and A is phenyl substituted in the meta position with

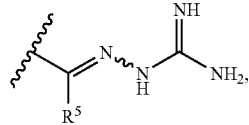

wherein R⁵ is as described above.

In another embodiment, the Compounds of formulas (I)-(III) do not include compounds wherein R² is

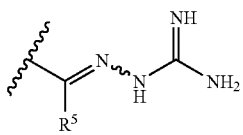

and A is phenyl substituted with

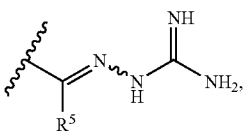

wherein R⁵ is as described above.

In another embodiment, the Compounds of formulas (I)-(III) do not include compounds wherein A is phenyl substituted with halogen, alkoxy, or $C_{1-6}$alkyl.

In another embodiment, the Compounds of formulas (I)-(III) do not include compounds wherein A is phenyl substituted with a secondary or tertiary amine.

In another embodiment, the Compounds of formulas (I)-(III) do not include compounds wherein A is phenyl substituted with —C(O)—NH—NH—C(=NH)NH₂.

In another embodiment, the Compounds of formulas (I)-(III) do not include compounds wherein A is phenyl substituted with —CH=N—NH—C(=NH)NH₂.

In another embodiment, the Compounds of formulas (I)-(III) do not include compounds wherein A is phenyl substituted with —CH=N—NH—C(S)—NH₂.

In another embodiment, the Compounds of formulas (I)-(III) do not include compounds wherein A is unsubstituted phenyl.

In another embodiment, the Compounds of formulas (I)-(III) do not include compounds wherein A is unsubstituted cyclohexyl.

In another embodiment, the Compounds of formulas (I)-(III) do not include compounds wherein A is acetyl.

In another embodiment, the Compounds of formulas (I)-(III) do not include compounds wherein A possesses a urea moiety.

In another embodiment, the Compounds of formulas (I)-(III) do not include:

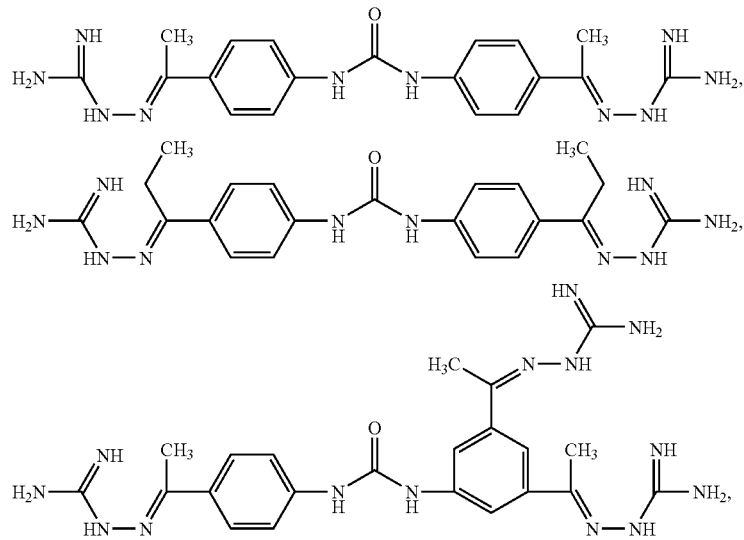

-continued
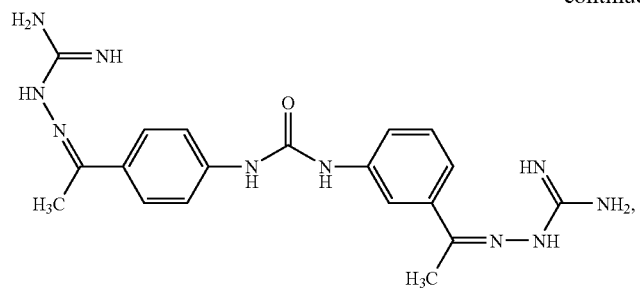
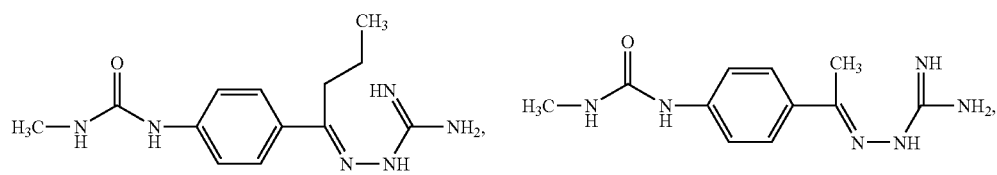
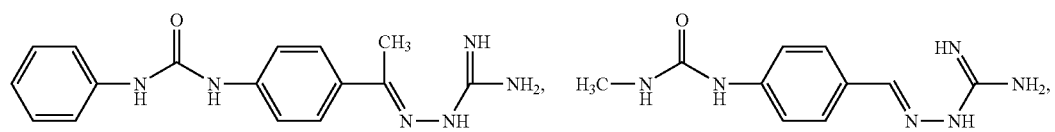
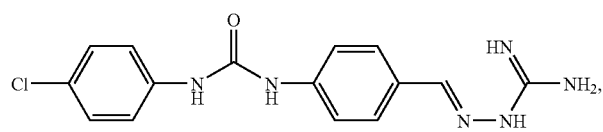
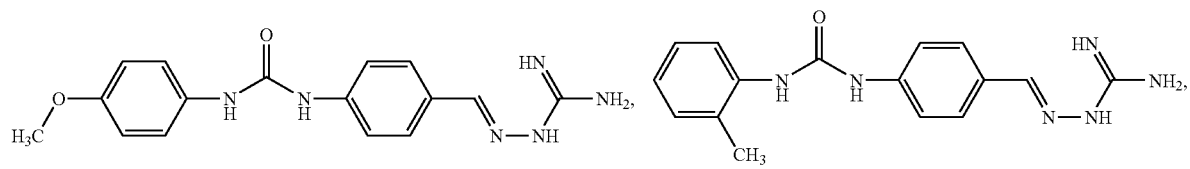
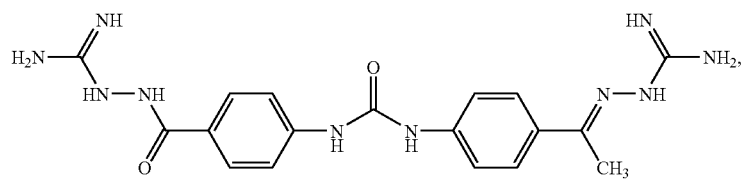
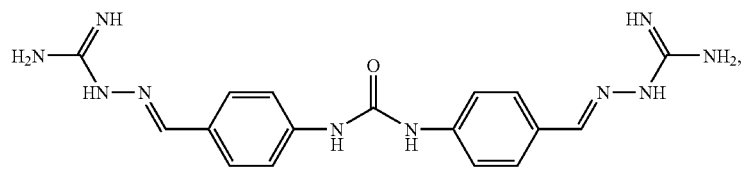
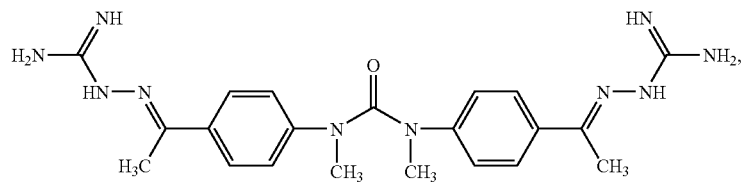

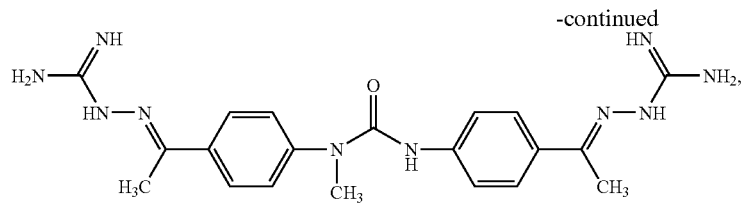
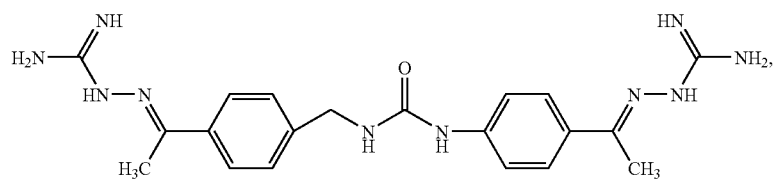
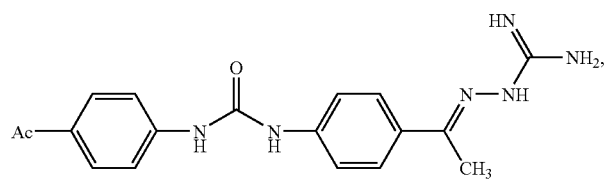
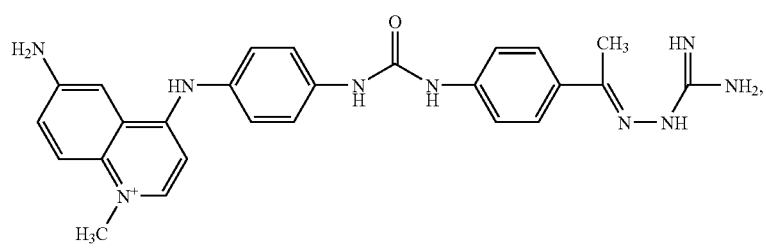
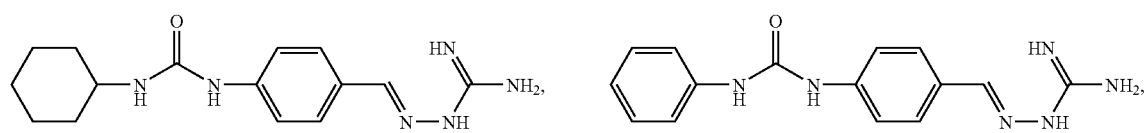
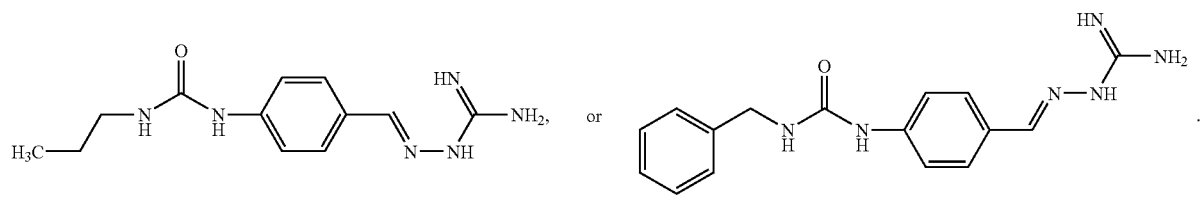
In a further embodiment, provided herein are Compounds of formula (IV):
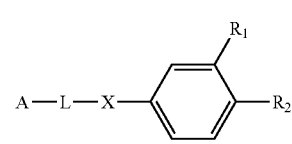
and pharmaceutically acceptable salts, solvates, hydrates and stereoisomers thereof, wherein:
$R^1$ is H;
$R^2$ is —C(O)H, —C(O)C$_{1-6}$alkyl or a group selected from:
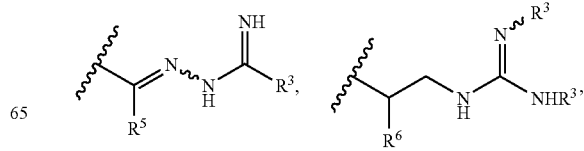

-continued

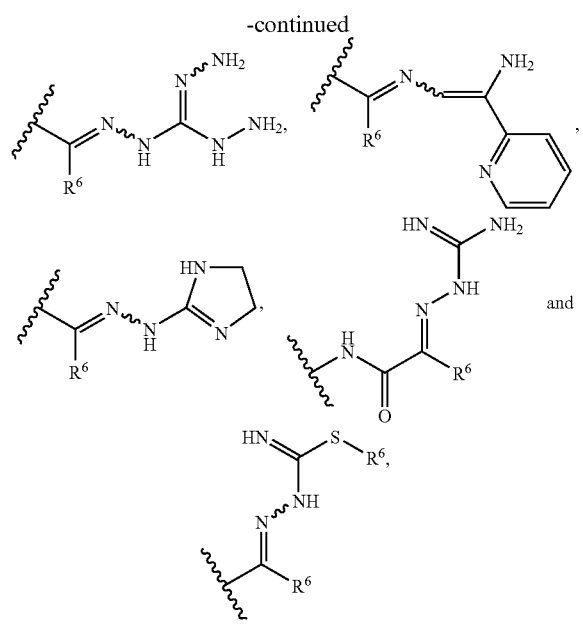

or $R^1$ and $R^2$ taken together with the atoms to which they are attached form a substituted or unsubstituted 5- or 6-membered cycloalkenyl ring;

X is —N($R^4$)—C(O)—N($R^4$)—, —C(O)—N($R^4$)—, —N($R^4$)—C(O)—, —N($R^4$)—N($R^4$)—C(O)—, —C(O)—N($R^4$)—N($R^4$)—, —C(O)—, —NH—SO$_2$—NH—, —NHSO$_2$— or —SO$_2$NH—;

L is a direct bond or $C_{1-6}$alkylene;

A is substituted or unsubstituted $C_{3-10}$heteroaryl;

$R^3$ is at each occurrence independently —NH$_2$, —NHOH, —NHR$^6$, —SH or —S—C$_{1-6}$alkyl; and $R^4$, $R^5$ and $R^6$ are at each occurrence independently H, substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{1-6}$alkyl, wherein either A is substituted with at least one of the following groups or $R^2$ is one of the following groups:

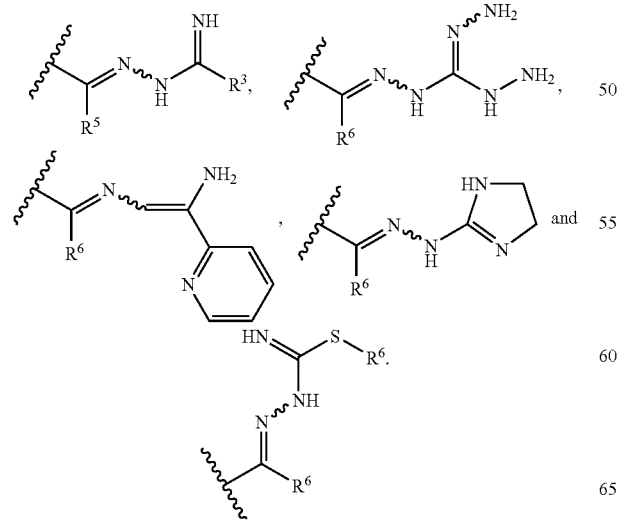

In a further embodiment, provided herein are Compounds of formula (V):

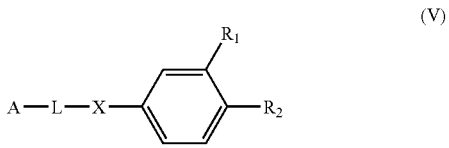

and pharmaceutically acceptable salts, solvates, hydrates and stereoisomers thereof, wherein:

$R^1$ and $R^2$ taken together with the atoms to which they are attached form a substituted or unsubstituted 5- or 6-membered cycloalkenyl ring;

X is —N($R^4$)—C(O)—N($R^4$)—, —C(O)—N($R^4$)—, —N($R^4$)—C(O)—, —N($R^4$)—N($R^4$)—C(O)—, —C(O)—N($R^4$)—N($R^4$)—, —C(O)—, —NH—SO$_2$—NH—, —NHSO$_2$— or —SO$_2$NH—;

L is a direct bond or $C_{1-6}$alkylene;

A is substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{1-6}$alkyl; and $R^4$ is H, substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{1-6}$alkyl, wherein A is substituted with at least one group selected from:

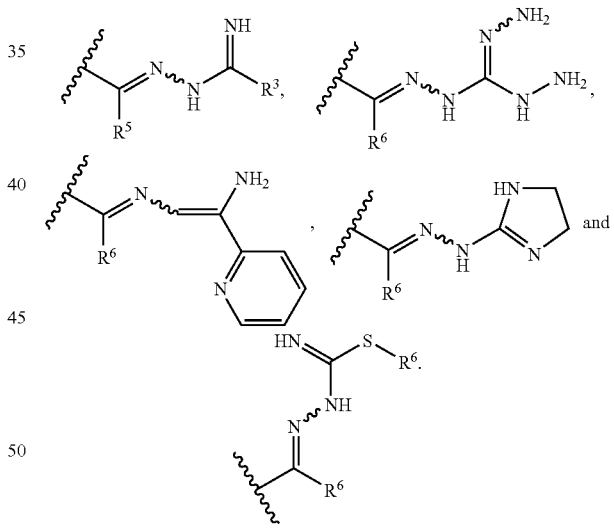

wherein:

$R^3$ is at each occurrence independently —NH$_2$, —NHOH, —NHR$^6$, —SH or —S—C$_{1-6}$alkyl; and $R^5$ and $R^6$ are at each occurrence independently H, substituted or unsubstituted aryl, substituted or unsubstituted $C_{3-10}$heteroaryl, substituted or unsubstituted $C_{3-10}$cycloalkyl, substituted or unsubstituted $C_{3-10}$heterocycloalkyl, or substituted or unsubstituted $C_{1-6}$alkyl.

In a particular embodiment, the Compounds of formula (V) are those wherein A is: phenyl substituted with halogen, $C_{1-6}$alkyl, C(O)$C_{1-6}$alkyl, CN, urea (e.g., —NH—C(=O)—NH—) or pyrimidine; unsubstituted $C_{3-10}$heteroaryl; $C_{3-10}$heteroaryl substituted with NH$_2$, NO$_2$, OH, halogen, C$_{1-6}$alkyl, alkoxy, carbamate or hydrazino guanidine (e.g., —CH(CH$_3$)=N—NH—CH(=NH)—NH$_2$); unsubstituted heterocycloalkyl; unsubstituted naphthyl; or naphthyl substituted with guanidine.

In another embodiment, the Compounds of formula (V) are those wherein A is substituted aryl, wherein the aryl group has 2-5 substituents (e.g., 2-5 substituents selected from substituents set forth herein).

In another embodiment, the Compounds of formula (V) are those wherein A is substituted or unsubstituted 1H-indole, substituted or unsubstituted 1H-indazole, substituted or unsubstituted benzofuran or substituted or unsubstituted benzo[d]thiazole.

In another embodiment, the Compounds of formula (V) are those wherein R$^1$ is H.

In another embodiment, the Compounds of formula (V) are those wherein R$^1$ and R$^2$ taken together with the atoms to which they are attached form substituted 5-membered cycloalkenyl ring.

In another embodiment, the Compounds of formula (V) are those wherein R$^1$ and R$^2$ taken together with the atoms to which they are attached form substituted 6-membered cycloalkenyl ring.

In another embodiment, the Compounds of formula (V) are those wherein X is —N(R$^4$)—C(O)—N(R$^4$)—, wherein R$^4$ is as described above.

In another embodiment, the Compounds of formula (V) are those wherein X is —C(O)—N(R$^4$)— or —N(R$^4$)—C(O)—, wherein R$^4$ is as described above.

In another embodiment, the Compounds of formula (V) are those wherein L is a direct bond.

In another embodiment, the Compounds of formula (V) are those wherein X is —N(R$^4$)—C(O)—N(R$^4$) and L is a direct bond, wherein R$^4$ is as described above.

In another embodiment, the Compounds of formula (V) are those wherein R$^4$ is H.

In another embodiment, the Compounds of formula (V) are those wherein A is substituted aryl.

In another embodiment, the Compounds of formula (V) are those wherein A is substituted or unsubstituted C$_{3-10}$heteroaryl.

In a further embodiment, provided herein are Compounds of formula (VI):

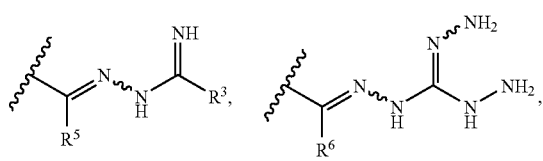

(VI)

and pharmaceutically acceptable salts, solvates, hydrates and stereoisomers thereof, wherein:

R$^2$ is —C(O)C$_{1-6}$alkyl or a group selected from:

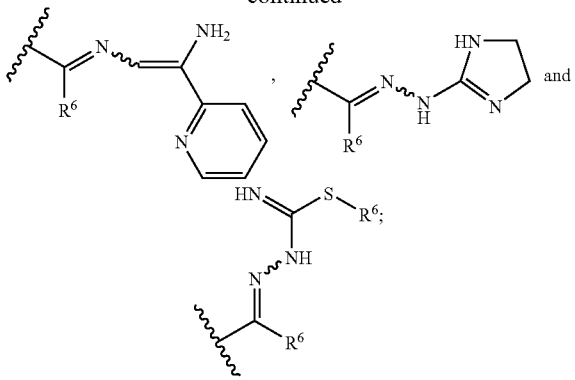

-continued

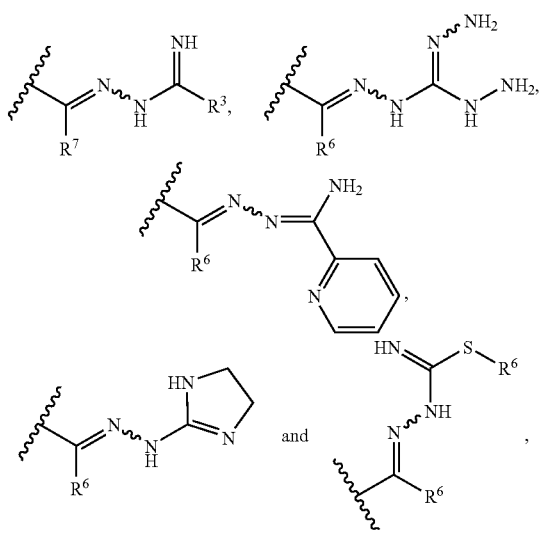

X is —N(R$^4$)—C(O)—N(R$^4$)—, —C(O)—N(R$^4$)—, —N(R$^4$)—C(O)—, —N(R$^4$)—N(R$^4$)—C(O)—, —C(O)—N(R$^4$)—N(R$^4$)—, —C(O)—, —NH—SO$_2$—NH—, —NHSO$_2$— or —SO$_2$NH—;

L is a direct bond or C$_{1-6}$alkylene;

A is substituted or unsubstituted C$_{3-10}$heteroaryl, aryl mono substituted with halogen, cyano, NH$_2$, NO$_2$, OH, C$_{1-6}$alkyl, alkoxy, —C(O)C$_{1-6}$alkyl, —N(R$^4$)—C(O)—N(R$^4$)— or a group selected from:

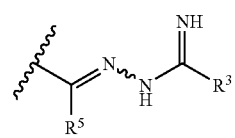

or aryl disubstituted with and C$_{1-6}$alkyl;

R$^3$ is at each occurrence independently —NH$_2$, —NHOH, —NHR$^6$, —SH or —S—C$_{1-6}$alkyl;

R$^4$, R$^5$ and R$^6$ are at each occurrence independently H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl; and R$^7$ is substituted or unsubstituted C$_{3-6}$alkyl, wherein either A is substituted with at least one of the following groups or R$^2$ is one of the following groups:

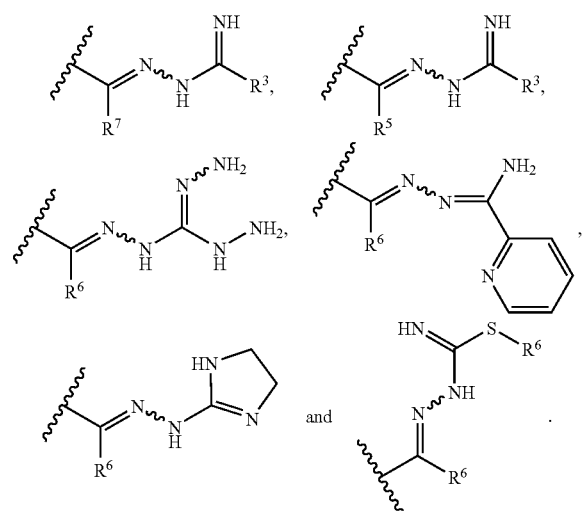

In a further embodiment, provided herein are Compounds of formula (VII):

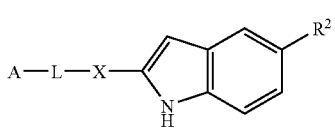

(VII)

and pharmaceutically acceptable salts, solvates, hydrates and stereoisomers thereof, wherein:

X is —N(R$^4$)—C(O)—N(R$^4$)—, —C(O)—N(R$^4$)—, —N(R$^4$)—C(O)—, —N(R$^4$)—N(R$^4$)—C(O)—, —C(O)—N(R$^4$)—N(R$^4$)—, —C(O)—, —NH—SO$_2$—NH—, —NHSO$_2$— or —SO$_2$NH—;

L is a direct bond or C$_{1-6}$alkylene;

A is substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl;

R$^2$ is

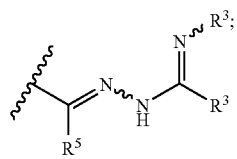

R$^3$ is at each occurrence independently H, —OH, —OC$_{1-6}$alkyl, —NH$_2$, —NHOH, —SH or —S—C$_{1-6}$alkyl; and R$^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl.

In one embodiment, the Compounds of formula (VII) are those wherein X is —C(O)—NH— and L is a direct bond.

In another embodiment, the Compounds of formula (VII) are those wherein R$^2$ is

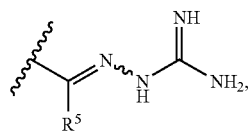

wherein R$^5$ is substituted or unsubstituted C$_{1-6}$alkyl.

In another embodiment, the Compounds of formula (VII) are those wherein R$^2$ is

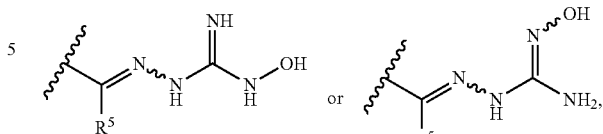

wherein R$^5$ is substituted or unsubstituted C$_{1-6}$alkyl.

In another embodiment, the Compounds of formula (VII) are those wherein A is substituted or unsubstituted aryl or substituted or unsubstituted heteroaryl.

In a further embodiment, provided herein are Compounds of formula (VIII):

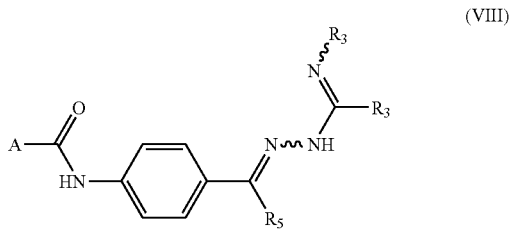

(VIII)

and pharmaceutically acceptable salts, solvates, hydrates and stereoisomers thereof, wherein:

A is substituted or unsubstituted C$_{3-10}$heteroaryl,

R$^3$ is at each occurrence independently H, —OH, —OC$_{1-6}$alkyl, —NH$_2$, —NHOH, —SH or —S—C$_{1-6}$alkyl; and R$^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl.

In one embodiment, the Compounds of formula (VIII) are those wherein R$_5$ is substituted or unsubstituted C$_{1-6}$alkyl, such as methyl.

In another embodiment, the Compounds of formula (VIII) are those wherein R$_3$ is NH$_2$ or OH.

In another embodiment, the Compounds of formula (VIII) are those wherein R$_3$ is NH$_2$ or H.

In another embodiment, the Compounds of formula (VIII) are those wherein R$_5$ is substituted or unsubstituted C$_{1-6}$alkyl, such as methyl, and R$_3$ is NH$_2$ or H.

In a further embodiment, provided herein are Compounds of formula (IX):

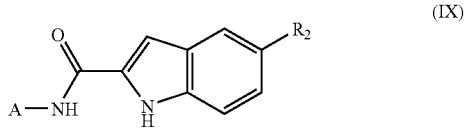

(IX)

and pharmaceutically acceptable salts, solvates, hydrates and stereoisomers thereof, wherein:

A is substituted or unsubstituted C$_{3-10}$heteroaryl,

R$^2$ is

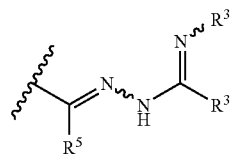

or —OC$_{1-6}$alkyl;

$R^3$ is at each occurrence independently H, —OH, —OC$_{1-6}$alkyl, —NH$_2$, —NHOH, —SH or —S—C$_{1-6}$alkyl; and $R^5$ is H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl.

In one embodiment, the Compounds of formula (IX) are those wherein $R_5$ is substituted or unsubstituted C$_{1-6}$alkyl, such as methyl.

In another embodiment, the Compounds of formula (IX) are those wherein $R_3$ is NH$_2$ or OH.

In another embodiment, the Compounds of formula (IX) are those wherein $R_3$ is NH$_2$ or H.

In another embodiment, the Compounds of formula (IX) are those wherein $R_5$ is substituted or unsubstituted C$_{1-6}$alkyl, such as methyl, and $R_3$ is NH$_2$ or H.

Representative Compounds are set forth in Table 1, below.

TABLE 1

| Compound | Chk2 EC$_{50}$ | RSK2 IC$_{50}$ |
|---|---|---|
| 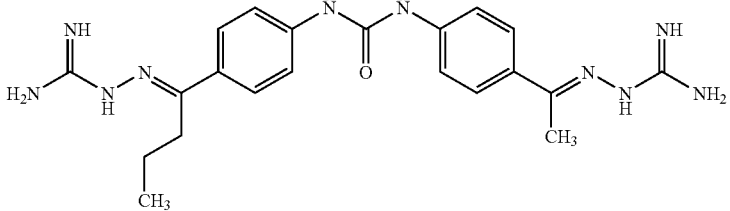 1 | A | |
| 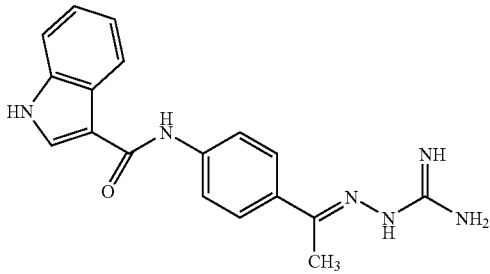 [SMILES: C/C(=N\NC(=N)N)c1ccc(NC(=O)c2c[nH]c3ccccc23)cc1] 2 | D | |
| 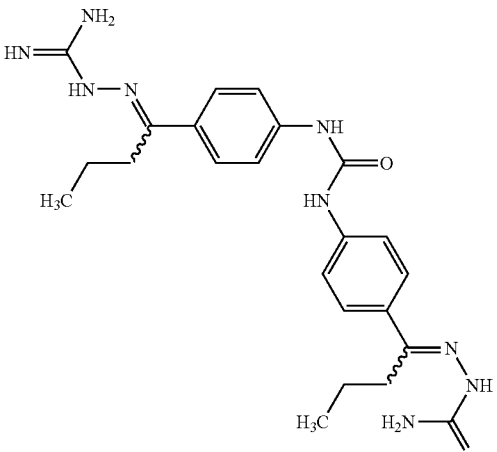 3 | A | |
| 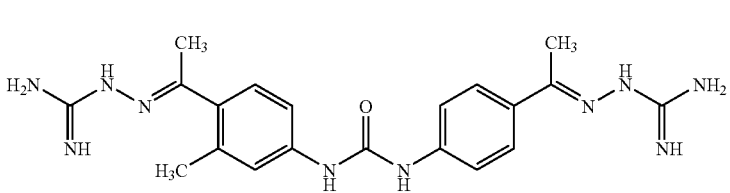 [SMILES: C/C(=N\NC(=N)N)c1ccc(NC(=O)Nc2ccc(/C(C)=N/NC(=N)N)c(C)c2)cc1] 4 | B | |

TABLE 1-continued

| Compound | Chk2 EC$_{50}$ | RSK2 IC$_{50}$ |
|---|---|---|
| 5 | C | |
| 6 | C | |
| 7 | C | |
| 8 | C | |
| 9 | B | |
| 10 | A | |

TABLE 1-continued
| Compound | Chk2 EC$_{50}$ | RSK2 IC$_{50}$ |
|---|---|---|
| 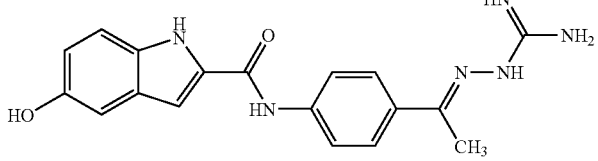 11 | C | |
| 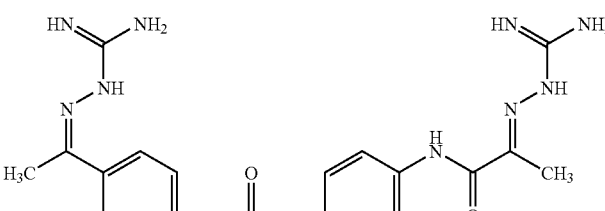 12 | C | |
| 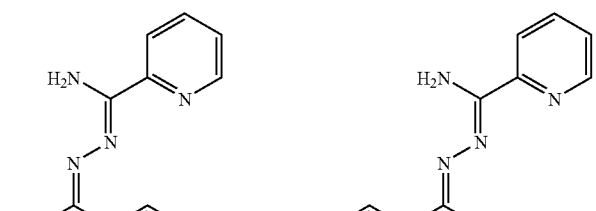 13 | C | |
|  14 | C | |
| 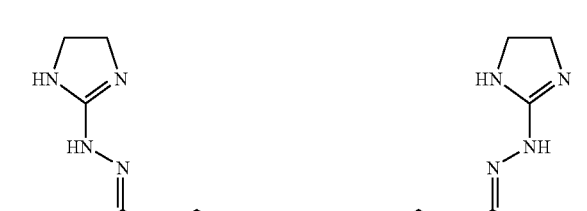 15 | A | |

TABLE 1-continued
| Compound | Chk2 EC$_{50}$ | RSK2 IC$_{50}$ |
|---|---|---|
| 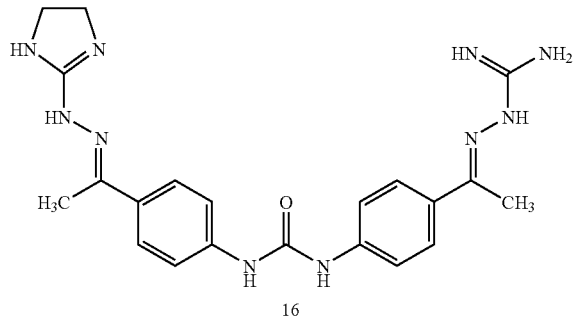<br>16 | A | |
| 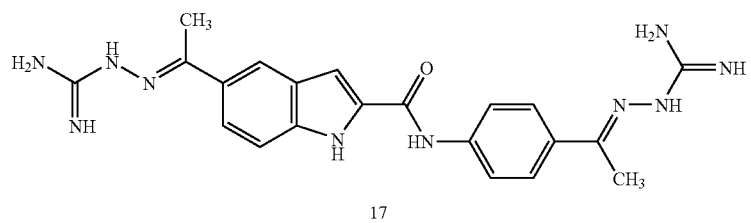<br>17 | A | |
| 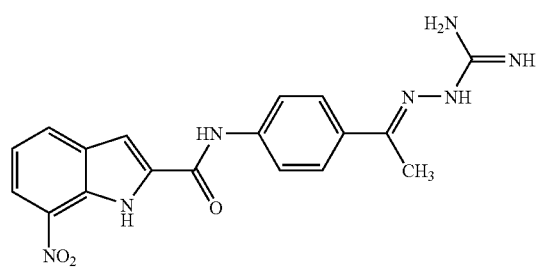 [SMILES: C/C(=N\NC(=N)N)c1ccc(NC(=O)c2cc3cccc([N+](=O)[O-])c3[nH]2)cc1]<br>18 | A | |
| 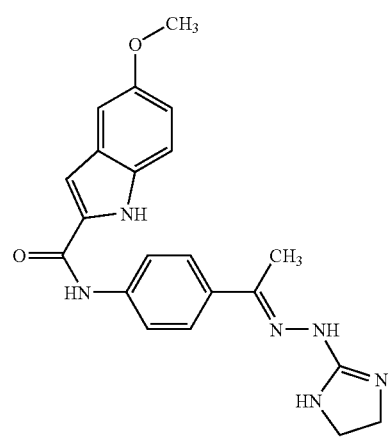 [SMILES: COc1ccc2[nH]c(C(=O)Nc3ccc(/C(C)=N/NC4=NCCN4)cc3)cc2c1]<br>19 | B | |

TABLE 1-continued
| Compound | Chk2 EC$_{50}$ | RSK2 IC$_{50}$ |
|---|---|---|
| 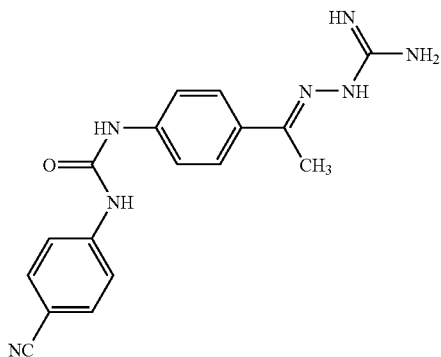 20 | A | |
| 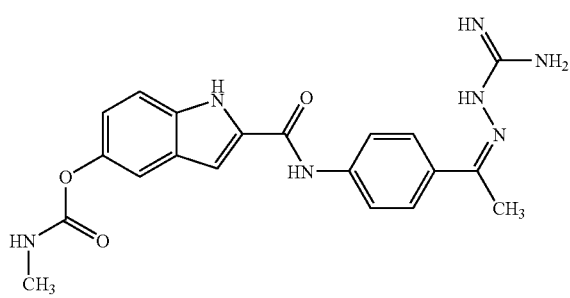 [SMILES: CNC(=O)Oc1ccc2[nH]c(C(=O)Nc3ccc(/C(C)=N\NC(=N)N)cc3)cc2c1] 21 | B | |
| 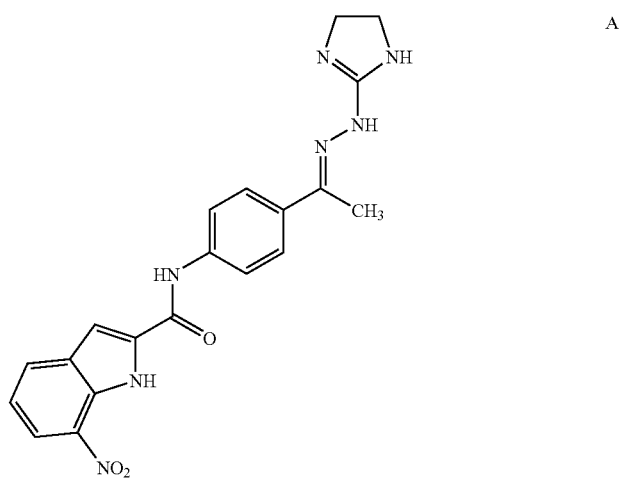 22 | A | |

TABLE 1-continued
| Compound | Chk2 EC$_{50}$ | RSK2 IC$_{50}$ |
|---|---|---|
| 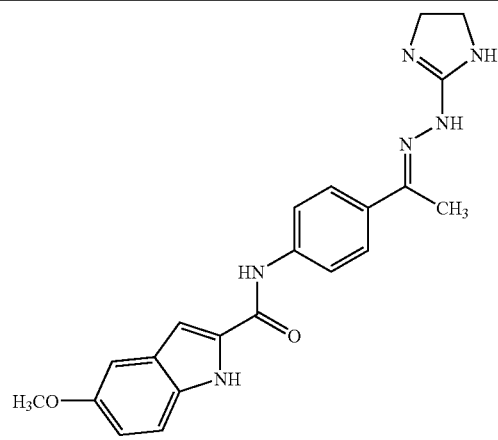 23 | A | |
| 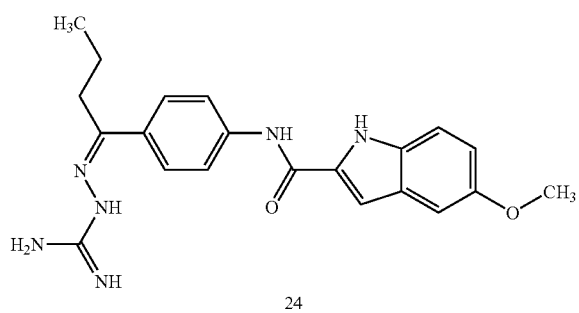 24 | A | |
| 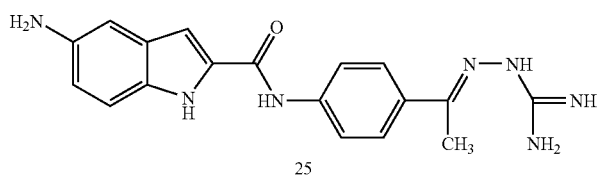 25 | C | |
| 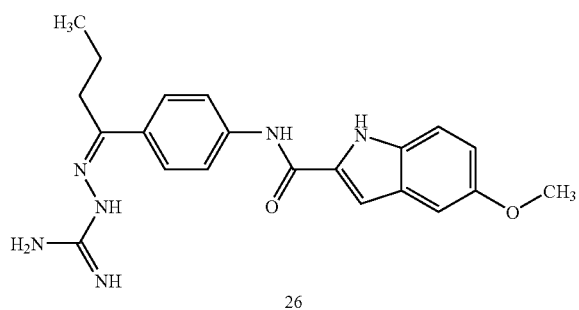 26 | C | |

TABLE 1-continued

| Compound | Chk2 EC$_{50}$ | RSK2 IC$_{50}$ |
|---|---|---|
| 27 | B | |
| 28 | A | |
| 29 | D | |
| 30 | C | |

TABLE 1-continued

| Compound | Chk2 EC$_{50}$ | RSK2 IC$_{50}$ |
|---|---|---|
| 31 | C | |
| 32 | D | |
| 33 | D | |
| 34 | D | |
| 35 | E | |

TABLE 1-continued
| Compound | Chk2 EC$_{50}$ | RSK2 IC$_{50}$ |
| --- | --- | --- |
| 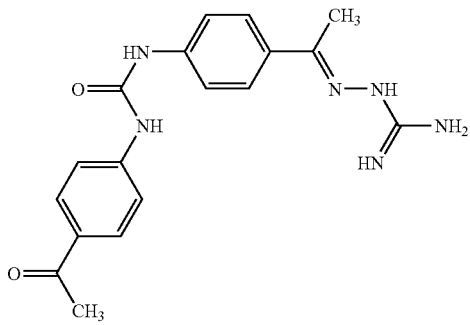 [SMILES: CC(=O)c1ccc(NC(=O)Nc2ccc(/C(C)=N/NC(=N)N)cc2)cc1] 36 | B | |
| 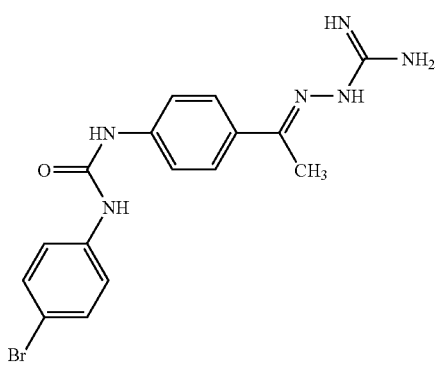 [SMILES: C/C(=N\NC(=N)N)c1ccc(NC(=O)Nc2ccc(Br)cc2)cc1] 37 | B | |
| 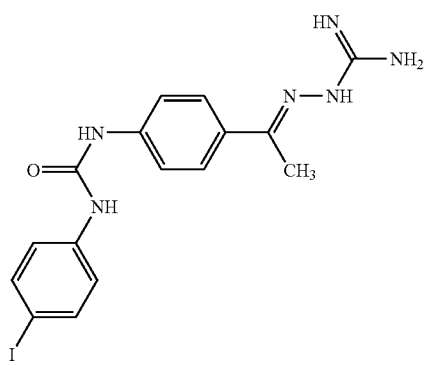 [SMILES: C/C(=N\NC(=N)N)c1ccc(NC(=O)Nc2ccc(I)cc2)cc1] 38 | C | |
| 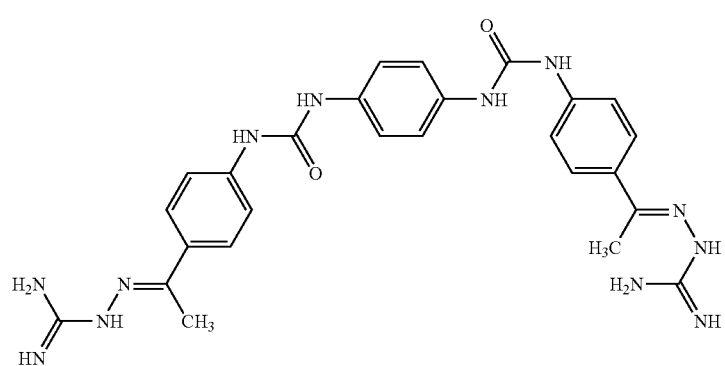 [SMILES: C/C(=N\NC(=N)N)c1ccc(NC(=O)Nc2ccc(NC(=O)Nc3ccc(/C(C)=N/NC(=N)N)cc3)cc2)cc1] 39 | A | |

TABLE 1-continued
| Compound | Chk2 EC$_{50}$ | RSK2 IC$_{50}$ |
|---|---|---|
| 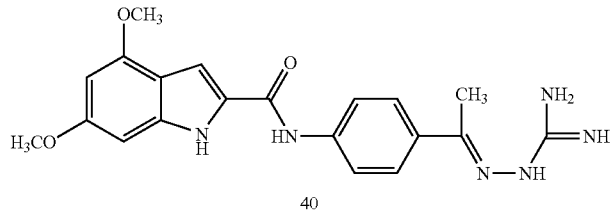 40 | D | |
| 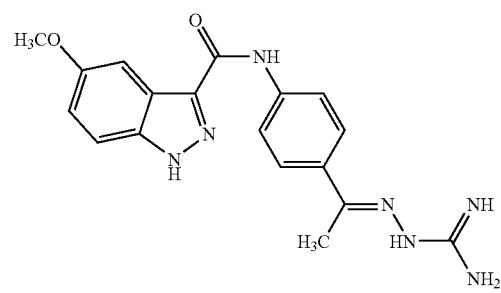 [SMILES: COc1ccc2[nH]nc(C(=O)Nc3ccc(/C(C)=N/NC(=N)N)cc3)c2c1] 41 | D | |
| 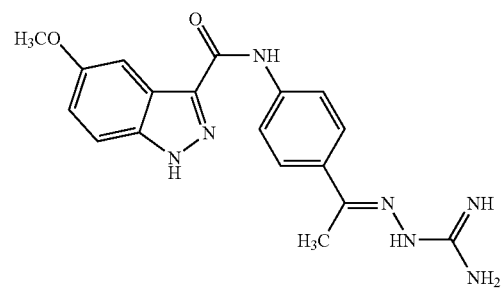 [SMILES: COc1ccc2[nH]nc(C(=O)Nc3ccc(/C(C)=N/NC(=N)N)cc3)c2c1] 42 | E | |
| 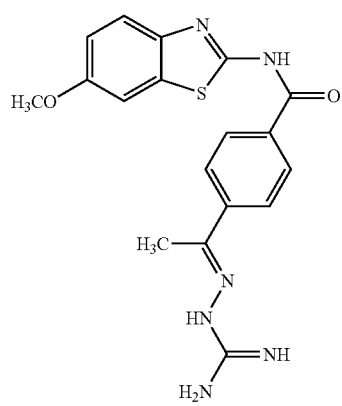 [SMILES: COc1ccc2nc(NC(=O)c3ccc(/C(C)=N/NC(=N)N)cc3)sc2c1] 43 | D | |

TABLE 1-continued
| Compound | Chk2 EC$_{50}$ | RSK2 IC$_{50}$ |
|---|---|---|
| 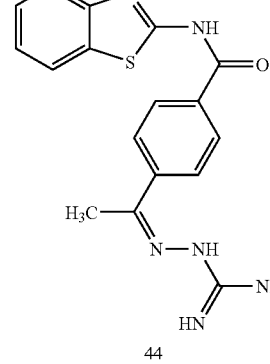 44 | | E |
| 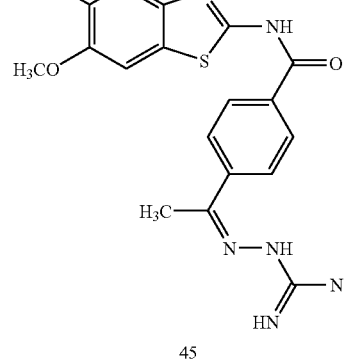 45 | | D |
| 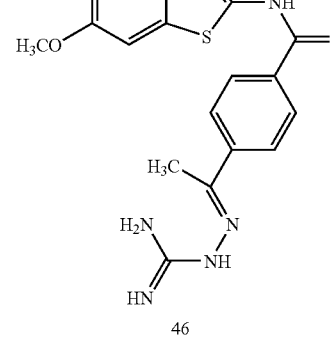 46 | | D |
| 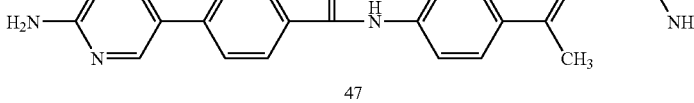 47 | | C |

TABLE 1-continued
| Compound | Chk2 EC$_{50}$ | RSK2 IC$_{50}$ |
|---|---|---|
| 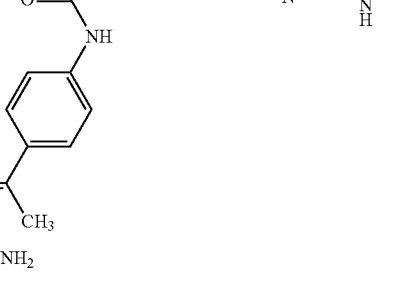 48 | E | |
| 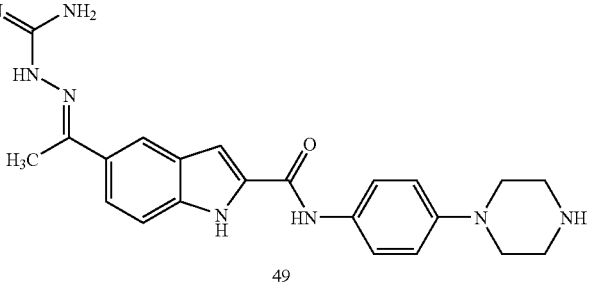 49 | B | |
| 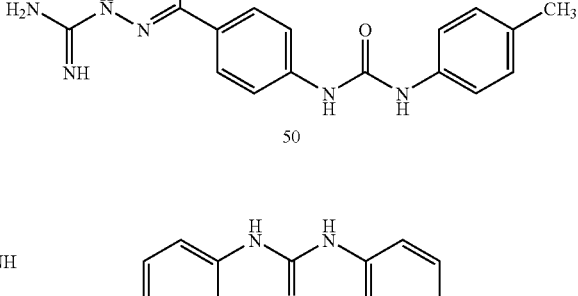 50 | D | |
| 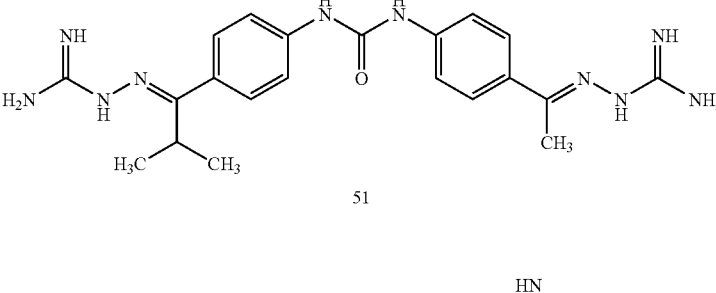 51 | D | |
| 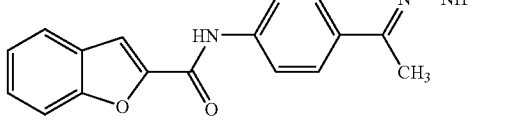 52 | D | |

TABLE 1-continued
| Compound | Chk2 EC$_{50}$ | RSK2 IC$_{50}$ |
|---|---|---|
| 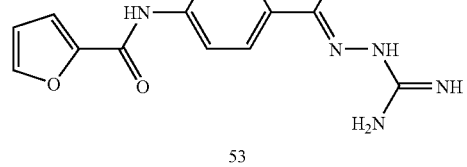<br>53 | D | |
| 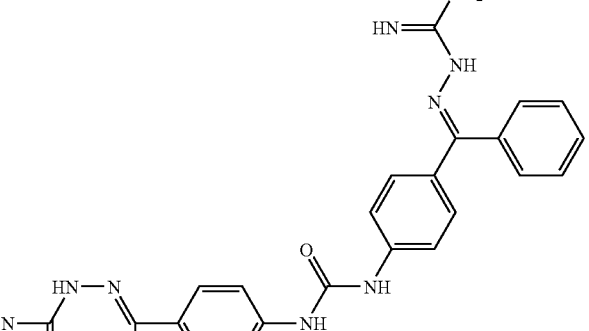<br>54 | D | |
| 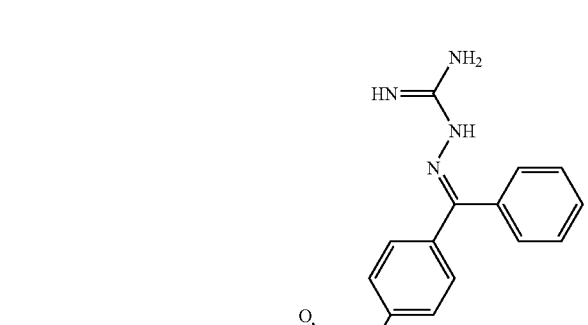<br>55 | E | |
| 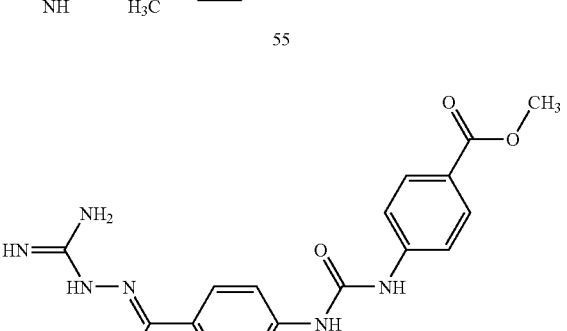<br>56 | D | |

TABLE 1-continued
| Compound | Chk2 EC$_{50}$ | RSK2 IC$_{50}$ |
|---|---|---|
| 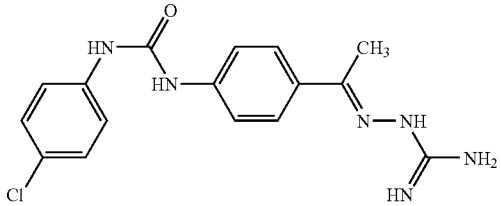 [SMILES: C/C(=N\NC(=N)N)c1ccc(NC(=O)Nc2ccc(Cl)cc2)cc1] 57 | D | |
| 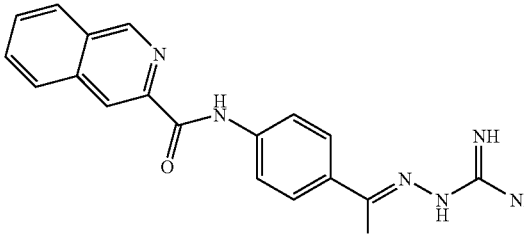 58 | D | |
| 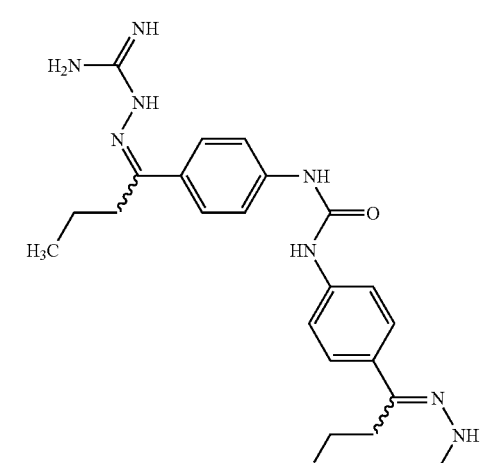 59 | C | |
| 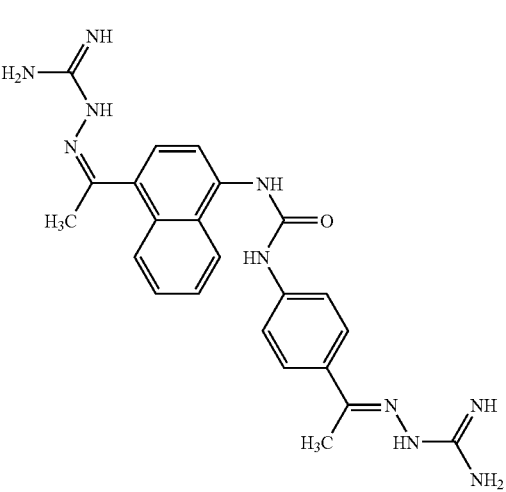 [SMILES: C/C(=N/NC(=N)N)c1ccc(NC(=O)Nc2ccc(/C(C)=N/NC(=N)N)cc2)c2ccccc12] 60 | D | |

TABLE 1-continued

| Compound | Chk2 EC$_{50}$ | RSK2 IC$_{50}$ |
|---|---|---|
| 61 | | E |
| 62 | | E |
| 63 | | D |
| 64 | | E |
| 65 | | B |

TABLE 1-continued
| Compound | Chk2 EC$_{50}$ | RSK2 IC$_{50}$ |
|---|---|---|
| 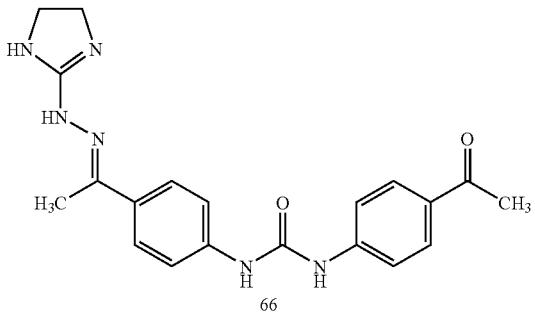 66 | | B |
| 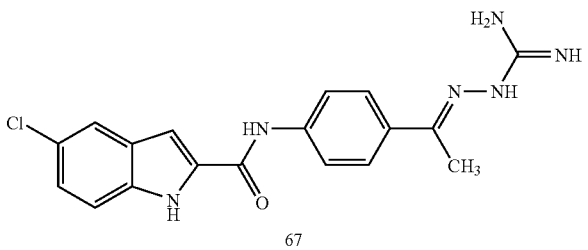 67 | | D |
| 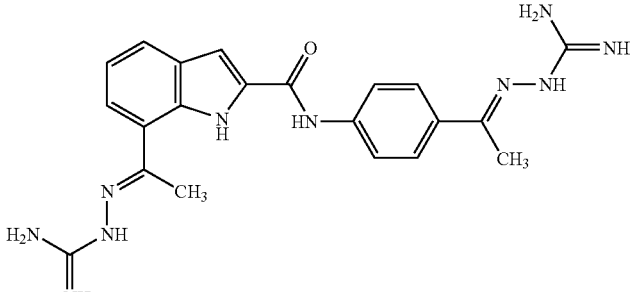 68 | | D |
| 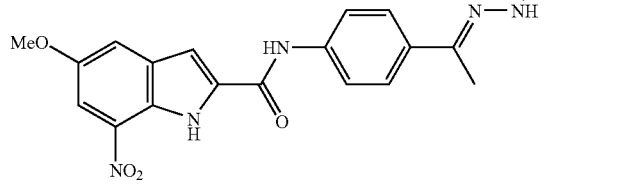 69 | | A |
| 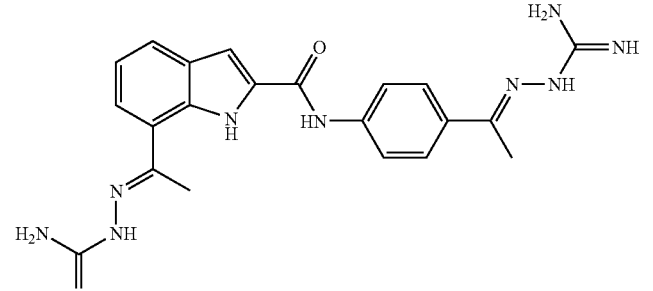 70 | | D |

TABLE 1-continued

| Compound | Chk2 EC$_{50}$ | RSK2 IC$_{50}$ |
|---|---|---|
| 71 | A | |
| 72 | C | |
| 73 | C | |
| 74 | C | |
| 75 | D | |
| 76 | C | |

TABLE 1-continued

| Compound | Chk2 EC$_{50}$ | RSK2 IC$_{50}$ |
|---|---|---|
| 77 | D | |
| 78 | B | |
| 79 | D | |
| 80 | C | |
| 81 | C | |

TABLE 1-continued

| Compound | Chk2 EC$_{50}$ | RSK2 IC$_{50}$ |
|---|---|---|
| 82 | D | |
| 83 | D | |
| 84 | D | |
| 85 | E | |
| 86 | A | |
| 87 | D | |
| 88 | C | |

TABLE 1-continued

| Compound | Chk2 EC$_{50}$ | RSK2 IC$_{50}$ |
|---|---|---|
| 89 | C | |
| 90 | D | C |
| 91 | C | C |
| 92 | C | |
| 93 | C | |
| 94 | C | B |
| 95 | D | |

TABLE 1-continued

| Compound | Chk2 EC$_{50}$ | RSK2 IC$_{50}$ |
|---|---|---|
| 96 | D | B |
| 97 | D | |
| 98 | D | |
| 99 | C | |
| 100 | E | |
| 101 | A | B |

TABLE 1-continued

| Compound | Chk2 EC$_{50}$ | RSK2 IC$_{50}$ |
|---|---|---|
| 102 | D | B |
| 103 | D | B |
| 104 | E | B |
| 105 | C | B |
| 106 | D | |
| 107 | D | B |

TABLE 1-continued
| Compound | Chk2 EC$_{50}$ | RSK2 IC$_{50}$ |
|---|---|---|
| 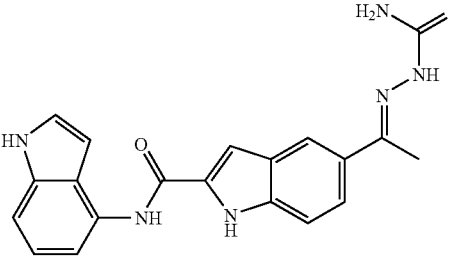 108 | D | B |
| 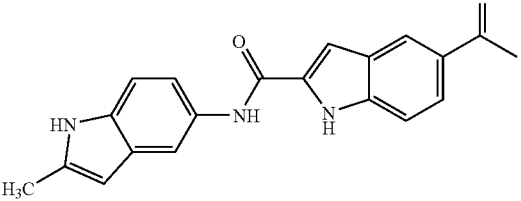 109 | C | |
| 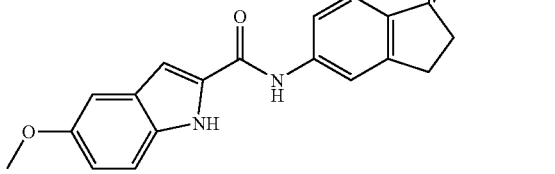 110 | E | B |
| 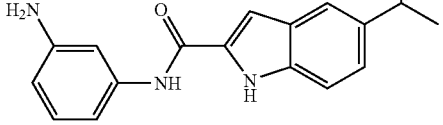 111 | C | B |
| 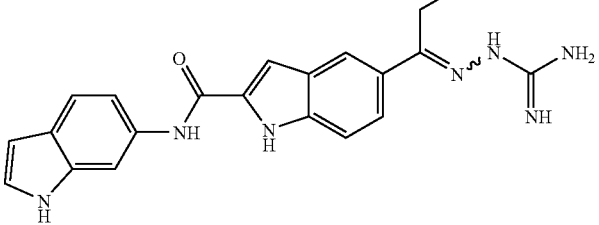 112 | A | B |

TABLE 1-continued
| Compound | Chk2 EC$_{50}$ | RSK2 IC$_{50}$ |
|---|---|---|
| 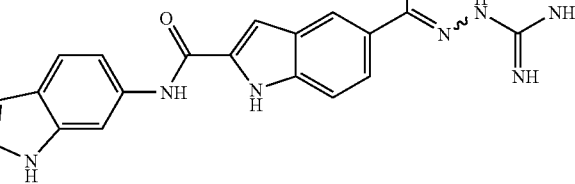 113 | C | C |
|  114 | D | |
| 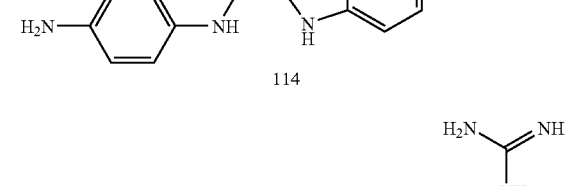 115 | B | C |
| 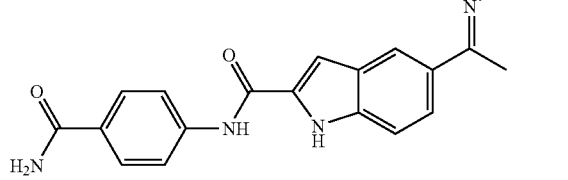 116 | A | |
|  117 | A | B |

TABLE 1-continued
| Compound | Chk2 EC$_{50}$ | RSK2 IC$_{50}$ |
|---|---|---|
| 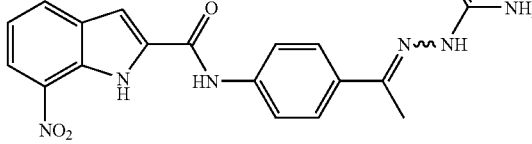 118 | A | B |
|  119 | | |
| 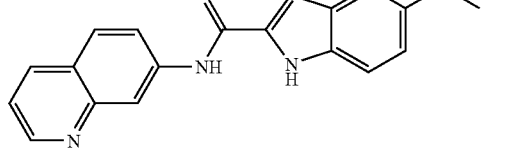 120 | | |
|  121 | A | B |
| 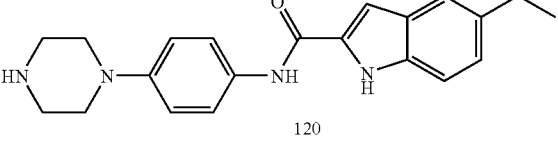 122 | E | B |

TABLE 1-continued
| Compound | Chk2 EC$_{50}$ | RSK2 IC$_{50}$ |
|---|---|---|
| 123 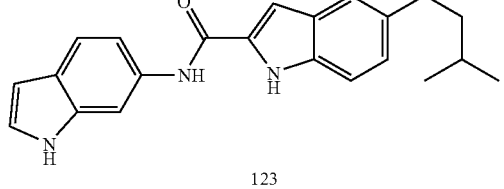 | A | B |
| 124 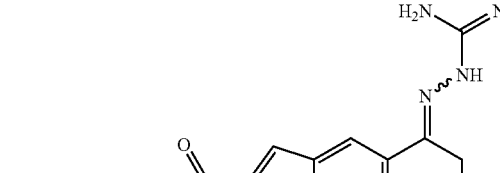 | D | B |
| 125 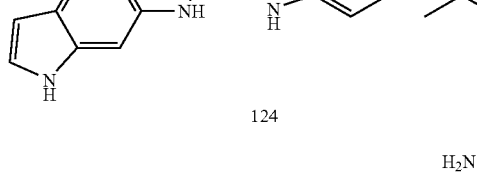 | B | B |
| 126 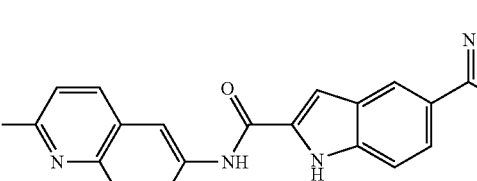 | A | A |
| 127 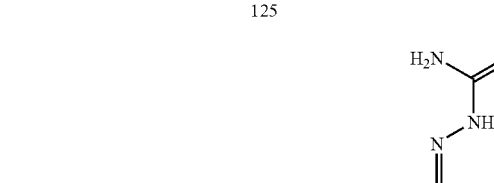 | B | B |

TABLE 1-continued

| Compound | Chk2 EC$_{50}$ | RSK2 IC$_{50}$ |
|---|---|---|
| 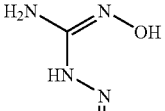 128 | B | C |
| 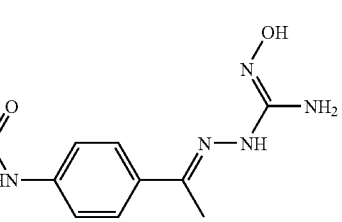 129 | C | A |
| 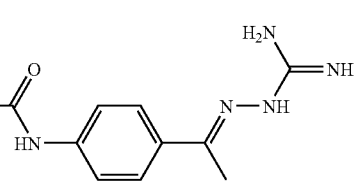 130 | A | C |

Compounds set forth in Table 1 were tested in the Chk2 inhibitor IMAP assay described herein in Example 6.84. Certain Compounds were found to have activity as Chk2 inhibitors. EC$_{50}$ values obtained using the Chk2 inhibitor IMAP assay are set forth in Table 1. The letters given for the Chk2 EC$_{50}$ values in Table 1 represent the following ranges: A=<100 nM; B=100-300 nM; C=300-1000 nM; D=1-10 µM; and E>10 µM.

Compounds set forth in Table 1 were tested in the RSK2 assay described herein in Example 6.86. Certain Compounds were found to have activity as RSK2 inhibitors. IC$_{50}$ values obtained using the RSK2 assay are set forth in Table 1. The letters given for the IC$_{50}$ values in Table 1 represent the following ranges: A=<1 µM; B=1-10 µM; and C=10-20 µM.

In one embodiment, Compounds target two or more of the following: kinases from the Chk kinase family, kinases from the MEK kinase family, kinases from the src kinase family, kinases from the RSK kinase family, kinases from the CDK family, kinases from the MAPK kinase family, and tyrosine kinases such as Fes, Lyn, and Syk kinases. Compounds may target two or more kinases of the same family, or may target kinases representing two or more kinase families or classes. Compounds may also target kinases with differing potencies.

In one embodiment, the Compound is selective for Chk2 over Chk1 (i.e., modulates or inhibits Chk2 activity without significantly modulating or inhibiting Chk1 activity). Without being limited by theory, it is thought that compounds selective for targeting Chk2 over Chk1 are particularly useful as therapeutic agents because the Chk2 pathway is activated first and transiently following DNA damage whereas the Chk1 pathway is activated secondarily and in a more sustained manner. In addition, Chk2 is also endogenously activated in a large fraction of tumors, and therefore might be critical for tumor growth. In a particular embodiment, a Compounds inhibits Chk2 activity two times, three times, four times, ten times, 20 times, 25 times or more than it inhibits Chk1 activity. Inhibition can be determined using Chk2 and Chk1 activity assays known in the art or set forth herein.

5.4 Methods for Making Compounds

The Compounds can be made using conventional organic syntheses. By way of example and not limitation, a Compound can be prepared as outlined in Schemes 1-3 shown below as well as in Examples 6.1 to 6.83.

Scheme 1:

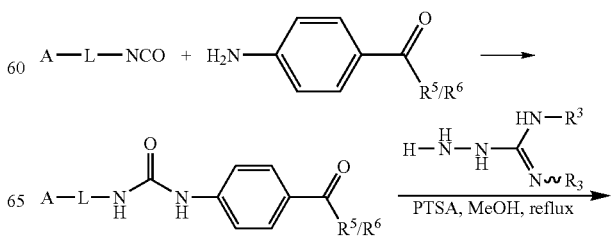

83
-continued
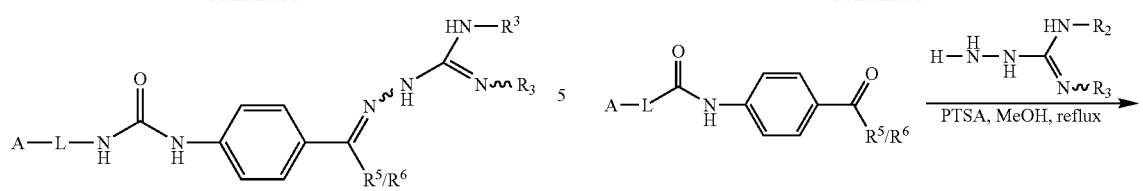
Scheme 2:
84
-continued
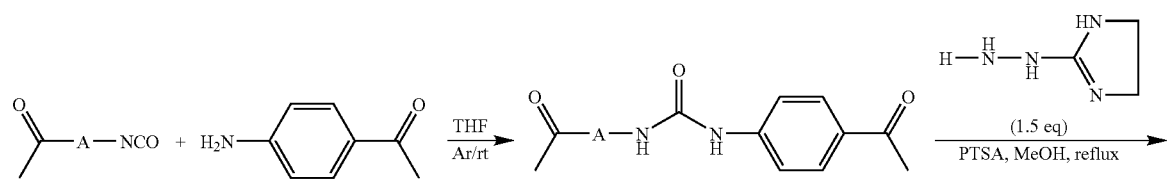
Scheme 3:
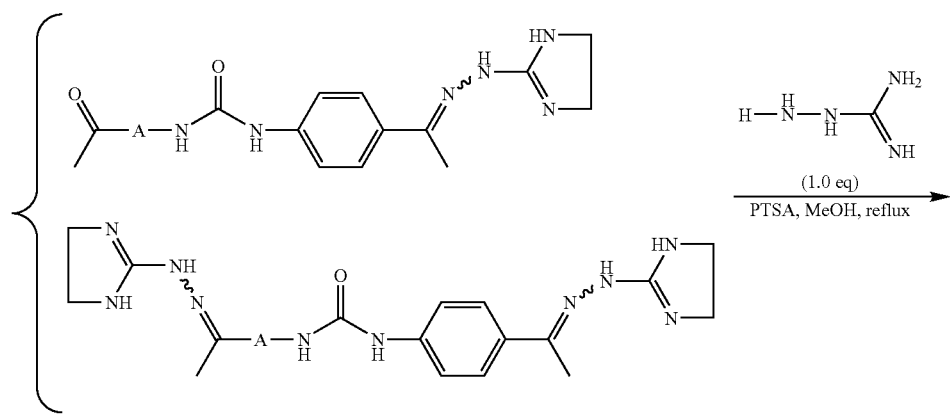
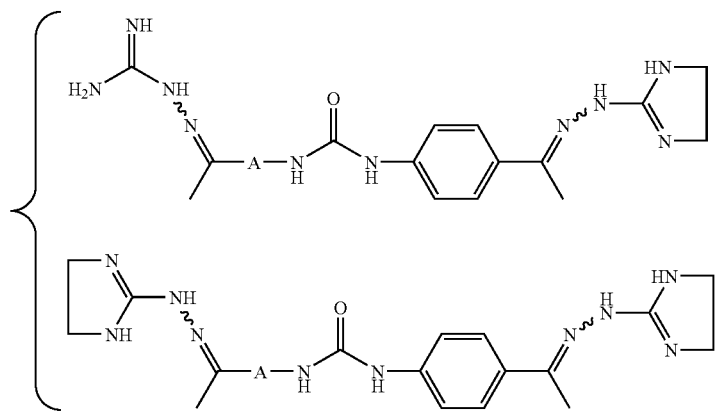

5.5 Methods of Use

The Compounds have utility as pharmaceuticals to treat or prevent disease in animals and/or humans. Further, the Compounds are active against protein kinases, such as Chk2, including those involved in cancer, hypoxia, diabetes, stroke, and autoimmune disease. Accordingly, provided herein are many uses of the Compounds, including the treatment or prevention of those diseases set forth below. The methods provided herein comprise the administration of a Compound to a patient in need thereof.

Representative autoimmune conditions that Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Grave's disease and diabetes (e.g., Type I diabetes).

Particular representative diabetic conditions that Compounds are useful for treating or preventing include, but are not limited to Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., imparied glucose metabolism), cystic fibrosis related diabetes, hemochromatosis and ketosis-resistant diabetes.

In a particular embodiment, provided herein are methods for the treatment or prevention of hypoxia comprising administering a Compound to a patient.

In a particular embodiment, provided herein are methods for the treatment or prevention of stroke comprising administering a Compound to a patient.

In a particular embodiment, provided herein are methods for the treatment or prevention of Coffin-Lowry syndrome comprising administering a Compound to a patient. In one embodiment, the Compound is of formula (VIII) or (IX).

Representative cancers that the Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

Cancers within the scope of the methods provided herein include those associated with one or more kinases from the Chk kinase family, kinases from the MEK kinase family, kinases from the src kinase family, kinases from the RSK kinase family, kinases from the CDK family, kinases from the MAPK kinase family, and tyrosine kinases such as Fes, Lyn, and Syk kinases, and mutants or isoforms thereof.

In a particular embodiment, provided herein are methods for the treatment or prevention of a disease or disorder associated with the modulation, for example inhibition, of a kinase, including, but are not limited to, Chk2 kinase, RSK2, tyrosine-protein kinase (SYK), tyrosine-protein kinase (ZAP-70), protein tyrosine kinase 2 beta (PYK2), focal adhesion kinase 1 (FAK), B lymphocyte kinase (BLK), hemopoietic cell kinase (HCK), v-yes-1 Yamaguchi sarcoma viral related oncogene homolog (LYN), T cell-specific protein-tyrosine kinase (LCK), proto-oncogene tyrosine-protein kinase (YES), proto-oncogene tyrosine-protein kinase (SRC), proto-oncogene tyrosine-protein kinase (FYN), proto-oncogene tyrosine-protein kinase (FGR), proto-oncogene tyrosine-protein kinase (FER), proto-oncogene tyrosine-protein kinase (FES), C-SRC kinase, protein-tyrosine kinase (CYL), tyrosine protein kinase (CSK), megakaryocyte-associated tyrosine-protein kinase (CTK), tyrosine-protein kinase receptor (EPH), Ephrin type-A receptor 1, Ephrin type-A receptor 4 (EPHA4), Ephrin type-B receptor 3 (EPHB3), Ephrin type-A receptor 8 (EPHA8), neurotrophic tyrosine kinase receptor, type 1 (NTRK1), protein-tyrosine kinase (PTK2), syk-related tyrosine kinase (SRK), protein tyrosine kinase (CTK), tyro3 protein tyrosine kinase (TYRO3), bruton agammaglobulinemia tyrosine kinase (BTK), leukocyte tyrosine kinase (LTK), protein-tyrosine kinase (SYK), protein-tyrosine kinase (STY), tek tyrosine kinase (TEK), elk-related tyrosine kinase (ERK), tyrosine kinase with immunoglobulin and egf factor homology domains (TIE), protein tyrosine kinase (TKF), neurotrophic tyrosine kinase, receptor, type 3 (NTRK3), mixed-lineage protein kinase-3 (MLK3), protein kinase, mitogen-activated 4 (PRKM4), protein kinase, mitogen-activated 1 (PRKM1), protein tyrosine kinase (PTK7), protein tyrosine kinase (EEK), minibrain (drosophila) homolog (MNBH), bone marrow kinase, x-linked (BMX), eph-like tyrosine kinase 1 (ETK1), macrophage stimulating 1 receptor (MST1R), btk-associated protein, 135 kd, lymphocyte-specific protein tyrosine kinase (LCK), fibroblast growth factor receptor-2 (FGFR2), protein tyrosine kinase-3 (TYK3), protein tyrosine kinase (TXK), tee protein tyrosine kinase (TEC), protein tyrosine kinase-2 (TYK2), eph-related receptor tyrosine kinase ligand 1 (EPLG1), t-cell tyrosine kinase (EMT), eph tyrosine kinase 1 (EPHT1), zona pellucida receptor tyrosine kinase, 95 kd (ZRK), protein kinase, mitogen-activated, kinase 1 (PRKMK1), eph tyrosine kinase 3 (EPHT3), growth arrest-specific gene-6 (GAS6), kinase insert domain receptor (KDR), axl receptor tyrosine kinase (AXL), fibroblast growth factor receptor-1 (FGFR1), v-erb-b2 avian erythroblastic leukemia viral oncogene homolog 2 (ERBB2), fms-like tyrosine kinase-3 (FLT3), neuroepithelial tyrosine kinase (NEP), neurotrophic tyrosine kinase receptor-related 3 (NTRKR3), eph-related receptor tyrosine kinase ligand 5 (EPLG5), neurotrophic tyrosine kinase, receptor, type 2 (NTRK2), receptor-like tyrosine kinase (RYK), tyrosine kinase, b-lymphocyte specific (BLK), eph tyrosine kinase 2 (EPHT2), eph-related receptor tyrosine kinase ligand 2 (EPLG2), glycogen storage disease VIII, eph-related receptor tyrosine kinase ligand 7 (EPLG7), janus kinase 1 (JAK1), fms-related tyrosine kinase-1 (FLT1), protein kinase, camp-dependent, regulatory, type I, alpha (PRKAR1A), wee-1 tyrosine kinase (WEE1), eph-like tyrosine kinase 2 (ETK2), receptor tyrosine kinase musk, insulin receptor (INSR), janus kinase 3 (JAK3), fms-related tyrosine kinase-3 ligand protein kinase c, beta 1 (PRKCB1), tyrosine kinase-type cell surface receptor (HER3), janus kinase 2 (JAK2), lim domain kinase 1 (LIMK1), dual specificity phosphatase 1 (DUSP1), hemopoietic cell kinase (HCK), tyrosine 3-monooxygenase/tryptophan 5-monooxygenase activation protein, eta polypeptide (YWHAH), ret proto-oncogene (RET), tyrosine 3-monooxygenase/tryptophan 5-monooxygenase activation protein, zeta polypeptide (YWHAZ), tyrosine 3-monooxygenase/tryptophan 5-monooxygenase activation protein, beta polypeptide (YWHAB), hepatoma transmembrane kinase (HTK), map kinase kinase 6, phosphatidylinositol 3-kinase, catalytic, alpha polypeptide (PIK3CA), cyclin-dependent kinase inhibitor 3 (CDKN3), diacylglycerol kinase, delta, 130 kd, protein-tyrosine phosphatase, nonreceptor type, 13 (PTPN13), abelson murine leukemia viral oncogene homolog 1 (ABL1), diacylglycerol kinase, alpha (DAGK1), focal adhesion kinase 2, epithelial discoidin domain receptor 1 (EDDR1), anaplastic lymphoma kinase (ALK), phosphatidylinositol 3-kinase, catalytic, gamma polypeptide (PIK3 CG), phosphatidylinositol 3-kinase regulatory subunit, (PIK3R1), eph homology kinase-1 (EHK1), v-kit hardy-zuckerman 4 feline sarcoma viral oncogene homolog (KIT), fibroblast growth factor receptor-3 (FGFR3), vascular endothelial growth factor c (VEGFC), epidermal growth factor receptor (EGFR), oncogene (TRK), growth factor receptor-bound protein-7 (GRB7), ras p21 protein activator (RASA2), met proto-oncogene (MET), src-like adapter (SLA), vascular endothelial growth factor (VEGF), vascular endothelial growth factor receptor (VEGFR), nerve growth factor receptor (NGFR), platelet derived growth factor receptor (PDGFR), platelet derived growth factor receptor beta (PDGFRB), dual-specificity tyrosine-(Y)-phosphorylation regulated kinase 2 (DYRK2), dual-specificity tyrosine-(Y)-phosphorylation regulated kinase 3 (DYRK3), dual-specificity tyrosine-(Y)-phosphorylation regulated kinase 4 (DYRK4), dual-specificity tyrosine-(Y)-phosphorylation regulated kinase 1A (DYRK1A), dual-specificity tyrosine-(Y)-phosphorylation regulated kinase 1B (DYRK1B), CDC-like kinase 1 (CLK1), protein tyrosine kinase STY, CDC-like kinase 4 (CLK4), CDC-like kinase 2 (CLK2) or CDC-like kinase 3 (CLK3).

In another embodiment, provided herein are methods for the treatment or prevention of a disease or disorder associated with the modulation, for example inhibition, of serine/threonine kinases or related molecules, including, but not limited to, cyclin-dependent kinase 7 (CDK7), rac serine/threonine protein kinase, serine-threonine protein kinase n (PKN), serine/threonine protein kinase 2 (STK2), zipper protein kinase (ZPK), protein-tyrosine kinase (STY), bruton agammaglobulinemia tyrosine kinase (BTK), mkn28 kinase, protein kinase, x-linked (PRKX), elk-related tyrosine kinase (ERK), ribosomal protein s6 kinase, 90 kd, polypeptide 3 (RPS6KA3), glycogen storage disease VIII, death-associated protein kinase 1 (DAPK1), pctaire protein kinase 1 (PCTK1), protein kinase, interferon-inducible double-stranded ma (PRKR), activin a receptor, type II-like kinase 1 (ACVRLK1), protein kinase, camp-dependent, catalytic, alpha (PRKACA), protein kinase, y-linked (PRKY), G protein-coupled receptor kinase 2 (GPRK21), protein kinase c, theta form (PRKCQ), lim domain kinase 1 (LIMK1), phosphoglycerate kinase 1 PGK1), lim domain kinase 2 (LIMK2), c-jun kinase, activin a receptor, type II-like kinase 2 (ACVRLK2), janus kinase 1 (JAK1), elk1 motif kinase (EMK1), male germ cell-associated kinase (MAK), casein kinase 2, alpha-prime subunit (CSNK2A2), casein kinase 2, beta polypeptide (CSNK2B), casein kinase 2, alpha 1 polypeptide (CSNK2A1), ret proto-oncogene (RET), hematopoietic progenitor kinase 1, conserved helix-loop-helix ubiquitous kinase (CHUK), casein kinase 1, delta (CSNKID), casein kinase 1, epsilon (CSNK1E), v-akt murine thymoma viral oncogene homolog 1 (AKT1), tumor protein p53 (TP53), protein phosphatase 1, regulatory (inhibitor) subunit 2 (PPP1R2), oncogene pim-1 (PIM 1), transforming growth factor-beta receptor, type II (TGFBR2), transforming growth factor-beta receptor, type I (TGFBR1), v-raf murine sarcoma viral oncogene homolog b1 (BRAF), bone morphogenetic receptor type II (BMPR2), v-raf murine sarcoma 3611 viral oncogene homolog 1 (ARAF1), v-raf murine sarcoma 3611 viral oncogene homolog 2 (ARAF2), protein kinase C (PKC), v-kit hardy-zuckerman 4 feline sarcoma viral oncogene homolog (KIT) or c-KIT receptor (KITR).

In another embodiment, provided herein are methods for the treatment or prevention of a disease or disorder associated with the modulation, for example inhibition, of a MAP kinase, including, but not limited to, mitogen-activated protein kinase 3 (MAPK3), p44erk1, p44mapk, mitogen-activated protein kinase 3 (MAP kinase 3; p44), ERK1, PRKM3, P44ERK1, P44MAPK, mitogen-activated protein kinase 1 (MAPK1), mitogen-activated protein kinase 1 (MEK1), MAP2K1protein tyrosine kinase ERK2, mitogen-activated protein kinase 2, extracellular signal-regulated kinase 2, protein tyrosine kinase ERK2, mitogen-activated protein kinase 2, extracellular signal-regulated kinase 2, ERK, p38, p40, p41, ERK2, ERT1, MAPK2, PRKM1, PRKM2, P42MAPK, p41mapk, mitogen-activated protein kinase 7 (MAPK7), BMK1 kinase, extracellular-signal-regulated kinase 5, BMK1, ERK4, ERK5, PRKM7, nemo-like kinase (NLK), likely ortholog of mouse nemo like kinase, mitogen-activated protein kinase 8 (MAPK8), protein kinase JNK1, JNK1 beta protein kinase, JNK1 alpha protein kinase, c-Jun N-terminal kinase 1, stress-activated protein kinase JNK1, JNK, JNK1, PRKM8, SAPK1, JNK1A2, JNK21B1/2, mitogen-activated protein kinase 10 (MAPK10), c-Jun kinase 3, JNK3 alpha protein kinase, c-Jun N-terminal kinase 3, stress activated protein kinase JNK3, stress activated protein kinase beta, mitogen-activated protein kinase 9 (MAPK9), MAP kinase 9, c-Jun kinase 2, c-Jun N-terminal kinase 2, stress-activated protein kinase JNK2, JNK2, JNK2A, JNK2B, PRKM9, JNK-55, JNK2BETA, p54aSAPK, JNK2ALPHA, mitogen-activated protein kinase 14 (MAPK14), p38 MAP kinase, MAP kinase Mxi2, Csaids binding protein, MAX-interacting protein 2, stress-activated protein kinase 2A, p38 mitogen activated protein kinase, cytokine suppressive anti-inflammatory drug binding protein, RK, p38, EXIP, Mxi2, CSBP1, CSBP2, CSPB1, PRKM14, PRKM15, SAPK2A, p38ALPHA, mitogen-activated protein kinase 11 (MAPK11), stress-activated protein kinase-2, stress-activated protein kinase-2b, mitogen-activated protein kinase p38-2, mitogen-activated protein kinase p38beta, P38B, SAPK2, p38-2, PRKM11, SAPK2B, p38Beta, P38BETA2, mitogen-activated protein kinase 13 (MAPK13), stress-activated protein kinase 4, mitogen-activated protein kinase p38 delta, SAPK4, PRKM13, p38delta, mitogen-activated protein kinase 12 (MAPK12), p38gamma, stress-activated protein kinase 3, mitogen-activated protein kinase 3, ERK3, ERK6, SAPK3, PRKM12, SAPK-3, P38GAMMA, mitogen-activated protein kinase 6 (MAPK6), MAP kinase isoform p97, mitogen-activated 5 protein kinase, mitogen-activated 6 protein kinase, extracellular signal-regulated kinase 3, extracellular signal-regulated kinase, p97, ERK3, PRKM6, p97MAPK, mitogen-activated protein kinase 4 (MAPK4), Erk3-related protein kinase, mitogen-activated 4 protein kinase (MAP kinase 4; p63), PRKM4, p63MAPK, ERK3-RELATED or Extracellular signal-regulated kinase 8 (ERK7).

More particularly, cancers and related disorders that can be treated or prevented by methods and compositions provided herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease;

multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and precancerous lesions such as familial adenomatous polyposis, and myclodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In another embodiment, the methods and compositions provided herein are also useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiences, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of myeloproliferative disorders or myelodysplastic syndromes, comprising administering to a patient in need thereof an effective amount of a Compound or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or agnogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of a Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of a Compound or a composition thereof.

In one embodiment, provided herein are methods for treating or preventing a disease or disorder treatable or preventable by inhibiting Chk2 or the ATM-Chk2 pathway, comprising administering an effective amount of a Compound to a patient in need of the treating or preventing. Particular diseases which are treatable or preventable by inhibiting Chk2 or the ATM-Chk2 pathway include, but are not limited to, cancer, hypoxia, diabetes, stroke, autoimmune disease, and other specific diseases and conditions disclosed herein.

In one embodiment, provided herein are methods for treating or preventing a disease or disorder treatable or preventable by inhibiting RSK2 or the RSK2 pathway, comprising administering an effective amount of a Compound to a patient in need of the treating or preventing. In one embodiment, the Compound is of formula (VIII) or (IX). Particular diseases which are treatable or preventable by inhibiting RSK2 or the RSK2 pathway include, but are not limited to, breast cancer, prostate cancer, osteosarcoma and Coffin-Lowry syndrome.

Further provided herein are methods for treating or preventing precancerous lesions, comprising administering an effective amount of a Compound to a patient having a precancerous lesion.

In another embodiment, provided herein are methods for the treatment or prevention of chemotherapy induced hair loss, comprising administering to a patient in need thereof (such as a patient who has undergone, is undergoing, or is scheduled to undergo chemotherapy) an effective amount of a Compound or a composition thereof. Without being limited by theory, it is thought that chemotherapy stimulates apoptosis in hair follicles, which results in hair loss. p53 is thought to be essential to this process (see, e.g., Botchkarev et al, 2000, *Cancer Res.* 60(18):5002-5006).

Further provided herein are methods for identifying a patient in need of administration (e.g., for treatment or prevention of a disease or disorder) of a Compound by determining the level of a marker (e.g., the expression level or activity of Chk2, RSK2, p53, E2F1, PML, a Cd25 phosphatase, Brca1 or a kinase disclosed herein) and administering an effective amount of a Compound to the patient.

Further provided herein are methods for inhibiting Chk2 or the ATM-Chk2 pathway in a cell expressing Chk2 comprising contacting said cell with a Compound.

Further provided herein are methods for inhibiting RSK2 or the RSK2 pathway in a cell expressing RSK2 comprising contacting said cell with a Compound.

Further provided herein are methods for inhibiting Chk2 or the ATM-Chk2 pathway in tissue comprising contacting said tissue with a Compound.

Further provided herein are methods for inhibiting RSK2 or the RSK2 pathway in tissue comprising contacting said tissue with a Compound.

Further provided herein are methods for protecting normal tissue (e.g., non-cancerous tissue) in a patient, comprising identifying a patient having tissue in need of such protection and administering to the patient an amount of a Compound effective to protect normal tissue. In a particular embodiment, the tissue is protected from becoming cancerous or metastases are reduced or avoided.

Further provided herein are methods for preventing or reducing apopstosis in a normal cell (e.g., non-cancerous cell) in a patient, comprising identifying a patient having one or more cells in need of such prevention or reduction and administering to the patient an amount of a Compound effective to prevent or reduce apoptosis in a normal cell.

Further provided herein a methods for sensitizing a tumor, a cancer cell or cancerous tissue to an anticancer agent, anticancer treatment (e.g., radiation therapy) or a DNA targeted agent (e.g., a chemotherapeutic), comprising administering a patient who has cancer or a tumor an amount of a Compound effective to sensitize the cancer or tumor to an anticancer agent, anticancer treatment or a DNA targeted agent. In one embodiment, the Compounds and the anticancer agent, anticancer treatment or a DNA targeted agent are administered in combination (e.g., simultaneously or sequentially). In a particular embodiment, the Compounds and the anticancer agent, anticancer treatment or a DNA targeted agent provide a synergistic effect when administered to a patient.

Chemotherapeutic agents that Compounds are useful in combination with include, but are not limited to, toposimoerase inhibitors, antiangiogenesis agents, selective estrogen-receptor modulators (SERMs), aromatase inhibitors and DNA-targeted agents. Specific chemotherapeutic agents that Compounds are useful in combination with include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; Erbitux™; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; ImiDs™; interleukin II (including recombinant interleukin II, or rIL2), interferon-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; SelCid™; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; temozolomide; temodar; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrapholide; angiogenesis inhibitors; antagonist D; antagonist G; antarelix; anti-dorsalizing morphogenetic protein-1; antiandrogen, prostatic carcinoma; antiestrogen; antineoplaston; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); cell-cycle inhibitors (e.g., flavopiridol A, tryprostatin B, p19ink4D); cyclin-dependent kinase inhibitors (e.g., roscovitine, olomucine and purine analogs); MAP kinase inhibitors (CNI-1493); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclizimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed;

ramosetron; retinoic acid (e.g., 9-cis RA); histone deacetylase inhibitors (e.g., sodium butyrate, suberoylanilide hydroxamic acid); TRAIL; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonennin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Further provided herein are methods for modulating (e.g., inhibiting) a substrate (e.g., p53, E2F1, or PML) in a normal cell (e.g., non-cancerous cell) in a patient, comprising identifying a patient having one or more cells in need of such modulation and administering to the patient an amount of a Compound effective to modulate the substrate in a normal cell.

Further provided herein are methods for modulating (e.g., inhibiting) a protein (e.g., a Cdc25 phosphatase) in a patient, comprising identifying a patient in need of such modulation and administering to the patient an amount of a Compound effective to modulate the protein.

Further provided herein are methods for modulating (e.g., inhibiting) Chk2 phosphorylation in a patient, comprising identifying a patient in need of such modulation and administering to the patient an amount of a Compound effective to modulate Chk2 phosphorylation. In a particular embodiment, Chk2 phosphorylation is inhibited or down-regulated.

5.6 Pharmaceutical Compositions and Routes of Administration

The Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Compounds in the pharmaceutical composition may be at a level that will exercise the desired effect; for example, about 0.005 mg/kg of a patient's body weight to about 10 mg/kg of a patient's body weight in unit dosage for both oral and parenteral administration. In one embodiment, a pharmaceutical composition is a composition suitable for administration to a patient, such as a human.

The dose of a Compound to be administered to a patient is rather widely variable and can be subject to the judgment of a health-care practitioner. In general, the Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Compound administered will depend on such factors as the solubility of the active component, the formulation used and the route of administration.

In another embodiment, provided herein are methods for the treatment or prevention of a disease or disorder disclosed herein comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Compound to a patient in need thereof.

In another embodiment, provided herein are methods for the treatment or prevention of a disease or disorder disclosed herein comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Compound to a patient in need thereof. In a particular embodiment, the methods disclosed herein comprise the administration of 400 mg/day, 600 mg/day or 800 mg/day of a Compound to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Compound.

In a particular embodiment, provided herein are unit dosage formulation comprising about 100 mg or 400 mg of a Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Compound.

A Compound can be administered once, twice, three, four or more times daily. In a particular embodiment, doses of 600 mg or less are administered as a a once daily dose and doses of more than 600 mg are administered twice daily in an amount equal to one half of the total daily dose.

A Compound can be administered orally for reasons of convenience. In one embodiment, when administered orally, a Compound is administered with a meal and water. In another embodiment, the Compound is dispersed in water or juice (e.g., apple juice or orange juice) and administered orally as a suspension.

The Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Compound without an additional carrier, excipient or vehicle.

In another embodiment, provided herein are compositions comprising an effective amount of a Phenyl and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

The effect of the Compound can be delayed or prolonged by proper formulation. For example, a slowly soluble pellet of the Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Compound in oily or emulsified vehicles that allow it to disperse slowly in the serum.

6. EXAMPLES

The following Examples are presented by way of illustration, not limitation.

General Procedures

All chemicals were purchased from Sigma-Aldrich Chemicals, Co. or Fisher Scientific and directly used without further purification. $^1$H and $^{13}$C NMR spectra were acquired on Varian 300 spectrometer at 25° C., and chemical shifts ($\delta$ in ppm) are given relative to that of Me$_4$Si (TMS, $\delta$ 0.00 ppm) or with the solvent reference relative to TMS employed as the internal standard (CDCl$_3$ $\delta$ 7.26; D$_6$-DMSO $\delta$ 2.50 ppm). Data are reported as follow: chemical shift (multiplicity [singlet (s), doublet (d), triplet (t), quartet (q), multiplet (m) broad (b)], coupling constants [Hz], integration. HPLC was performed on Rainin SD-300 or Varian ProStar equipped with a single wavelength UV detector at 214 nm and linear gradients. Analytical HPLC was performed on a Varian C$_{18}$ column (microsorb 60-8, 4.6×250 mm) at a flow rate of 1 mL/min. Semi-preparative HPLC was performed on a Varian C$_{18}$ column (microsorb 60-8, 10.0×250 mm) at a flow rate of 5 mL/min. Preparative HPLC was routinely performed on a Varian C$_{18}$ column (microsorb 60-8, 21.4×250 mm) at a flow rate of 20 mL/min. The solvent system used on linear gradients was water with 0.075% TFA (solvent A) vs Acetonitrile with 0.075% TFA (solvent B). Silica gel used in flash column chromatography was obtained from Sorbent Technologies (Atlanta, Ga.). Analytical thin-layer chromatography (TLC) was carried out using Silica Gel 60 F254 precoated plates G/UV254 plates (Merck, 0.25 mm thickness). TLC R$_f$ values are reported. Visulization was accomplished by irradiation with a UV lamp and/or staining with Ceric ammonium molybdate (CAM) solution. LC-MS spectra were taken on Thermo Finnigan Navigator LC/MS-ESI or APCI.

$^{13}$C NMR can be used to determine E/Z stereochemistry of Compounds. An established method for the discrimination of isomeric hydrazones is based on the γ-effect: carbon atoms being in γ-position (α to C═N) in a syn configuration with the N-2 hydrazone atom suffer an upfield shift compared to the γ-atoms in the anti position, due to steric compression.

Reports in the literature demonstrate that the chemical shift of E and Z α-methyl carbons in a guanidinyl hydrazone are more than 10 ppm apart (Györgydeák, Z.; Holzer, W.; Mereiter, K. *Monatsh. Chem.* 1999, 130, 899-913; Göβnitzer, E.; Feierl, G.; Wagner, U. *Eur. J. Pharm. Sci.* 2002, 15, 49-61).

Method A (Urea Linkers)

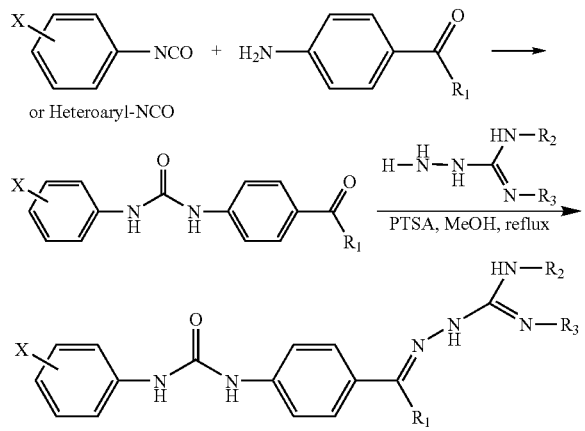

$R_1$ = Me, Et, nPr
$R_2 = R_3$ = H, or $R_2$, $R_3$ = —$CH_2CH_2$—
X = 4-halogen, 4-CN, 4-COMe, 4-COOMe Method B (Amide Linkers)

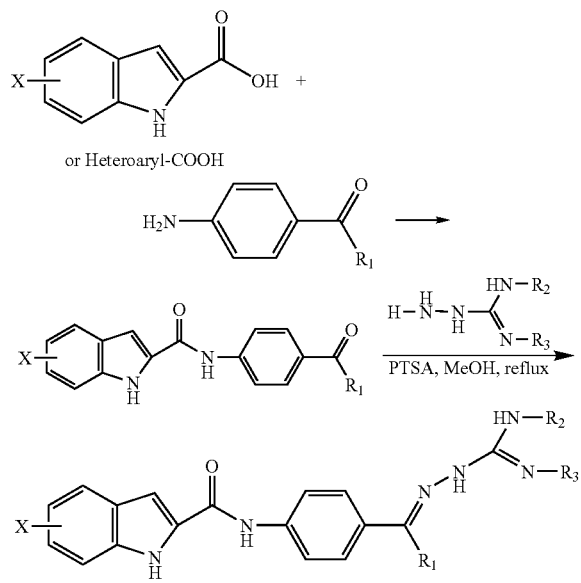

$R_1$ = Me, Et, nPr
$R_2 = R_3$ = H, or $R_2$, $R_3$ = —$CH_2CH_2$—
X = 5-Me, 5-halogen, 5-CN, 5-OMe, 5-$CONH_2$, 5-$NH_2$, 7-$NO_2$, Illustrative Compounds were synthesized and characterized as described below. Compound numbers refer to the numbering in Table 1, above.

Example 6.1

Synthesis of Compound 1

Step (i):
4-acetylphenyl isocyanate (98.8 mg, 0.613 mmol, 1.0 eq) was added to the solution of 1-(4-aminophenyl)-1-butanone (100.0 mg, 0.613 mmol, 1.0 eq) in one portion in anhydrous THF (3 mL) at room temperature under Ar. The reaction mixture was stirred overnight at rt. After concentration, the residue solid was washed with diethyl ether for 3 times and dried on the vacuum over 2 hour to obtain the crude urea 155.3 mg in 78% yield, which was directly used in the next step without further purification.

Step (ii):
The solution of crude urea (155 mg, 0.479 mmol, 1.0 eq)) from (i) above was combined with aminoguanidine hydrochloride (212 mg, 1.92 mmol, 4.0 eq) and p-toluenesulphonic acid monohydrate (328 mg, 3.60 mmol, 4.4 eq) in anhydrous MeOH (5 ml), refluxed for 10 min at 90° C. and then stirred for another hour at room temperature. The crude product was purified by reverse phase HPLC. $t_R$ 12.2 min (20-60% $CH_3CN$ in $H_2O$, 15 min); MS (m/z) 218 ($M^+/2$), 437 ($MH^+$).

Following the procedure of Method A, using the appropriate isocyanates as starting materials, the following guanadinylhydrazones were prepared:

Example 6.2

Synthesis of Compound 3

1-(4-isocyanato-phenyl)-1-butanone was prepared by treatment of 1-(4-aminophenyl)-1-butanone and triphosgene. The isocyanate was combined with 1-(4-aminophenyl)-1-butanone according to Method A to obtain after purification by reverse phase HPLC the product. $t_R$ 22.9 min (10-50% $CH_3CN$ in $H_2O$, 30 min); MS (m/z) 232 ($M^+/2$), 465 ($MH^+$).

Example 6.3

Synthesis of Compound 4

4-Acetylphenyl isocyanate and 4-amino-2-methylacetophenone were combined according to Method A, to obtain after purification by reverse phase HPLC the product. $t_R$ 10.5 min (20-30% $CH_3CN$ in $H_2O$, 15 min); MS (m/z) 211 ($M^+/2$), 422 ($M^+$).

Example 6.4

Synthesis of Compound 5

4-Acetylphenyl isocyanate and 6-amino-2-methyl-3,4-dihydro-2H-naphthalenone were combined according to Method A, to obtain after purification by reverse phase HPLC the product $t_R$ 17.4 min (10-90% $CH_3CN$ in $H_2O$, 20 min); MS (m/z) 224 ($M^+/2$), 449 ($MH^+$).

Example 6.5

Synthesis of Compound 6

4-Acetylphenyl isocyanate and 5-amino-indanone were combined according to Method A, to obtain after purification by reverse phase HPLC the product $t_R$ 10.6 min (prep. 20-60% $CH_3CN$ in $H_2O$, 20 min); MS (m/z) 210 ($M^+/2$), 420 ($M^+$).

Example 6.6

Synthesis of Compounds 13 and 14

The urea intermediate was prepared from 4-acetylphenyl isocyanate and 4'-amino acetophenone by following Method A step (i). To a solution of the urea in anhydrous MeOH (5 mL) was added 2-pyridylhydrazidine (1.5 eq) and para toluenesulphonic acid monhydrate (5 eq). The reaction was refluxed for 6-7 min, then rapidly cooled to room temperature. The MS showed the mono-substituent (m/z 414) and disubstituent (m/z 533). Then aminoguanidine hydrochloride (1.0 eq) was added to the reaction mixture and the solution refluxed for another 6-7 min at 90° C. The crude products were purified and isolated by reverse phase HPLC. Both symmetric disubstituted compound (13) and asymmetric disubstituted compound (14) were obtained in this one-pot reaction. 13 $t_R$ 18.1 min (20-60% $CH_3CN$ in $H_2O$, 25 min); MS (m/z) 266 ($M^+/2$), 533 ($MH^+$). 14 $t_R$ 16.2 min (20-60% $CH_3CN$ in $H_2O$, 25 min); MS (m/z) 235 ($M^+/2$), 471 ($MH^+$).

Example 6.7

Synthesis of Compounds 15 and 16

The urea intermediate was prepared from 4-acetylphenyl isocyanate and 4'-amino acetophenone by following Method A step (i). To a solution of the urea in anhydrous MeOH (5 mL) was added 2-hydrazino-2-imidazoline hydrobromide (1.5 eq) and para toluenesulphonic acid monhydrate (5 eq). The reaction was first refluxed for 10 min, then aminoguanidine hydrochloride (1.0 eq) was added to the reaction mixture and refluxed for another 6-7 min at 90° C. The crude products were purified and isolated by reverse phase HPLC. Both symmetric disubstituted compound (15) and asymmetric disubstituted compound (16) were obtained from this one-pot reaction. 15 $t_R$ 17.2 min (20-60%, $CH_3CN$, 20 min); MS (m/z) 461 ($MH^+$). 16 $t_R$ 14.5 min (20-60% $CH_3CN$ in $H_2O$, 20 min); MS (m/z) 435 ($MH^+$).

Example 6.8

Synthesis of Compound 20

4-Cyanophenyl isocyanate and 4-amino-2-methylacetophenone were combined according to Method A, to obtain after purification by reverse phase HPLC the product. $t_R$ 22.2 min (prep. 15-50% $CH_3CN$ in $H_2O$, 40 min); MS (m/z) 335 ($M^+$).

Example 6.9

Synthesis of Compound 2

Step (i):
To a solution of 1H-indole-3-carboxlic acid (250 mg, 1.551 mmol, 1.0 eq) and 4'-aminoacetophenone (210 mg, 1.551 mmol, 1.0 eq) in anhydrous DMF (5 mL) was added HBTU (676 mg, 1.783 mmol, 1.15 eq), followed by DIPEA (0.675 mL, 1.783 mmol, 2.5 eq) at room temperature. The reaction mixture was stirred overnight at room temperature. After concentration, the residue was washed with diethyl ether and dried on the vacuum overnight to obtain the crude amide (85 mg), which was directly used in the next step without further purification.

Step (ii):
A solution of crude amide (85 mg, 0.306 mmol, 1.0 eq)) from (i) above, aminoguanidine hydrochloride (52 mg, 0.459 mmol, 1.5 eq) and para toluenesulphonic acid (88 mg, 0.462 mmol, 1.5 eq) in anhydrous MeOH (3 ml) was refluxed for 6-7 min at 90° C., and then stirred for another hour at room temperature. After concentration under vacuum the crude product was purified by reverse phase HPLC $t_R$=12.3 min (15-35% $CH_3CN$ in $H_2O$, 15 min); MS-ESI (m/z) 334 ($M^+$).

Following the procedure of Method B, using the appropriate indole analogs as starting materials and if required alternative coupling reagents (e.g. HATU; BOP or pyBOP), the following guanidinylhydrazones were prepared:

Example 6.10

Synthesis of Compound 7

1H-Indole-2-carboxlic acid and 4'-aminoacetophenone were combined according to Method B (steps (i) and (ii)), to obtain after purification by reverse phase HPLC the product, $t_R$ 14.8 min (20-60% $CH_3CN$ in $H_2O$, 15 min); MS (m/z) 334 ($M^+$).

Example 6.11

Synthesis of Compound 8

Benzofuran-2-carboxlic acid and 4'-aminoacetophenone were combined according to Method B (steps (i) and (ii)), to obtain the product. $t_R$ 12.7 min (10-90% $CH_3CN$ in $H_2O$, 15 min); MS (m/z) 335 ($M^+$).

Example 6.12

Synthesis of Compound 9

5-Methyl-1H-indole-2-carboxlic acid and 4'-aminoacetophenone were combined according to Method B (steps (i) and (ii)), to obtain the product. $t_R$ 20.0 min (20-60% $CH_3CN$ in $H_2O$, 30 min); MS (m/z) 349 ($MH^+$).

Example 6.13

Synthesis of Compound 10

5-Methoxy-1H-indole-2-carboxlic acid and 4'-aminoacetophenone were combined according to Method B (steps (i) and (ii)), to obtain the product. $t_R$ 14.5 min (20-60% $CH_3CN$ in $H_2O$, 20 min); MS (m/z) 365 ($MH^+$).

Example 6.14

Synthesis of Compound 11

5-Hydroxy-1H-indole-2-carboxlic acid and 4'-aminoacetophenone were combined according to Method B (steps (i) and (ii)), to obtain the product. $t_R$ 11.9 min (20-40% $CH_3CN$ in $H_2O$, 20 min); MS (m/z) 351 ($MH^+$).

Example 6.15

Synthesis of Compound 17

5-Acetyl-1H-indole-2-carboxlic acid and 4'-aminoacetophenone were combined according to Method B (steps (i) and (ii)). The guanadinylation reaction was carried out utilizing aminoguanidine (2 eq) and para toluensulphonic acid monohydrate (3 eq) in methanol at reflux. After concentration under vacuum the crude product was purified by reverse phase HPLC to obtain the product, $t_R$ 15.0 min (10-60% $CH_3CN$ in $H_2O$, 20 min); MS (m/z) 433 ($MH^+$).

Example 6.16

Synthesis of Compound 18

5-Nitro-1H-indole-2-carboxlic acid and 4'-aminoacetophenone were combined according to Method B (steps (i) and (ii)), to obtain the product. $t_R$ 18.8 min (20-70%, $CH_3CN$, 25 min); MS (m/z) 397 ($M^+$).

Example 6.17

Synthesis of Compound 19

5-Methoxy-1H-indole-2-carboxlic acid and 4'-aminoacetophenone were combined according to Method B (steps (i) and (ii)), to obtain the product. $t_R$ 28.0 min (15-45% $CH_3CN$ in $H_2O$, 35 min); MS (m/z) 390 ($M^+$).

Example 6.18

Synthesis of Compound 21

5-hydroxy-1H-indole-2-carboxlic acid and 4'-aminoacetophenone were combined according to Method B (step (i)), to afford the intermediate carboxamide. This material was treated with excess methyl isocyanate to form the Indole 5-hydroxycarbamate, which was then reacted with aminoguanidine (Method B, step (ii)), to obtain the product. $t_R$ 14.0 min (20-40% $CH_3CN$ in $H_2O$, 20 min); MS (m/z) 408 ($MH^+$).

Example 6.19

Synthesis of Compound 22

7-nitro-1H-indole-2-carboxlic acid and 4'-aminoacetophenone were combined according to Method B (steps (i) and (ii)), to obtain the product, $t_R$ 16.0 min (20-80% $CH_3CN$ in $H_2O$, 20 min); MS (m/z) 405 ($M^+$).

Example 6.20

Synthesis of Compound 23

Start from 5-methoxy-1H-indole-2-carboxlic acid and 4'-aminoacetophenone were combined according to Method B (steps (i) and (ii)), to obtain the product. $t_R$ 15.0 min (20-80% $CH_3CN$ in $H_2O$, 20 min); MS (m/z) 390 ($M^+$).

Example 6.21

Synthesis of Compounds 24 and 26

5-Methoxy-1H-indole-2-carboxlic acid and 1-(4-aminophenyl)-1-butanone were combined according to Method B (steps (i) and (ii)), to obtain two products (E/Z geometric isomers, hydrazone double bond); 24, $t_R$ 16.4 min (25-60%, $CH_3CN$, 20 min); MS (m/z) 393 ($MH^+$); and 26, $t_R$ 17.7 min (25-60% $CH_3CN$ in $H_2O$, 20 min); MS (m/z) 393 ($MH^+$).

Example 6.22

Synthesis of Compound 25

5-Amino-1H-indole-2-carboxlic acid and 4'-aminoacetophenone following were combined according to Method B (steps (i) and (ii)), to obtain the product. $t_R$ 19.8 min (5-30% $CH_3CN$ in $H_2O$, 30 min); MS (m/z) 350 ($MH^+$).

Example 6.23

Synthesis of Compound 27

5-Carbamoyl-1H-indole-2-carboxylic acid and 4'-aminoacetophenone were combined according to Method B (steps (i) and (ii)), to obtain the product. $t_R$ 12.6 min (10-60% $CH_3CN$ in $H_2O$, 20 min); MS (m/z) 378 ($MH^+$).

Example 6.24

Synthesis of Compound 28

5-Acetyl-1H-indole-2-carboxylic acid and 4'-aminoacetophenone were combined according to Method B (steps (i) and (ii)), to obtain the product. $t_R$ 15.5 min (10-90% $CH_3CN$ in $H_2O$, 20 min); MS (m/z) 410 ($MH^+$).

Example 6.25

Synthesis of Compound 68

7-Acetyl-1H-indole-2-carboxylic acid and 4-amino acetophenone were combined according to Method B (steps (i) and (ii)) to obtain the pure product after HPLC purification. $t_R$ 16.97 min (10-50% $CH_3CN$ in $H_2O$, 20 min); MS (m/z) 433 ($MH^+$).

Example 6.26

Synthesis of Compound 71

5-(2-Methyl-[1,3]dithian-2-yl)-1H-indole-2-carboxylic acid prepared as described in the literature (Vijay Kumar and Sukh, Dev. Tetrahedron Letters, 1983, 24(12), 1289-1292) and 4'-aminoacetophenone were combined according to Method B (steps (i) and (ii)). After 1,3-dithiane deprotection by the DMP oxidation procedure (Langille, N. F.; Dakin, L. A.; Panek, J. S. Org. Lett. 2003; 5(4); 575-578), the pure monohydrozone was obtained by HPLC purification. $t_R$ 22.03 min (15-45% $CH_3CN$ in $H_2O$, 40 min, semiprep); MS (m/z) 377 ($MH^+$).

Example 6.27

Synthesis of Compound 73

5,6-Dimethoxy-1H-indole-2-carboxylic acid and 4'-aminoacetophenone were combined according to Method B (steps (i) and (ii)), to obtain the product after HPLC purification. $t_R$ 14.38 min (20-50% $CH_3CN$ in $H_2O$, 20 min); MS (m/z) 395 ($MH^+$).

Example 6.28

Synthesis of Compound 74

6-Methoxy-1H-indole-2-carboxylic acid and 4'-aminoacetophenone were combined according to Method B (steps (i) and (ii)), to obtain the product after HPLC purification. $t_R$ 16.66 min (20-60% $CH_3CN$ in $H_2O$, 25 min); MS (m/z) 365 ($MH^+$).

Example 6.29

Synthesis of Compound 76

7-Acetylamino-1H-indole-2-carboxylic acid and 4'-aminoacetophenone were combined according to Method B (steps (i) and (ii)), to obtain the product after HPLC purification. $t_R$ 15.11 min (10-60% $CH_3CN$ in $H_2O$, 20 min); MS (m/z) 392 (MH$^+$).

Example 6.30

Synthesis of Compound 78

5-Methoxy-benzofuran-2-carboxylic acid and 4'-aminoacetophenone were combined according to Method B (steps (i) and (ii)), to obtain the product after HPLC purification. $t_R$ 18.50 min (10-60% $CH_3CN$ in $H_2O$, 20 min); MS (m/z) 366 (MH$^+$).

Example 6.31

Synthesis of Compound 86

7-Nitro-1H-indole-2-carboxylic acid and 6-Amino-3,4-dihydro-2H-naphthalen-1-one were combined according to Method B (steps (i) and (ii)), to obtain the product after HPLC purification. $t_R$ 15.71 min (20-70% $CH_3CN$ in $H_2O$, 20 min); MS (m/z) 406 (MH$^+$).

Example 6.32

Synthesis of Compound 88

6-Acetylamino-1H-indole-2-carboxylic acid and 4'-aminoacetophenone were combined according to Method B (steps (i) and (ii)), to obtain the product after HPLC purification. $t_R$ 14.55 min (10-60% $CH_3CN$ in $H_2O$, 20 min); MS (m/z) 392 (MH$^+$).

Example 6.33

Synthesis of Compound 89

6-Methanesulfonyl-1H-indole-2-carboxylic acid and 4'-aminoacetophenone were combined according to Method B (steps (i) and (ii)), to obtain the product after HPLC purification. $t_R$ 15.29 min (10-60% $CH_3CN$ in $H_2O$, 20 min); MS (m/z) 392 (MH$^+$).

Example 6.34

Synthesis of Compound 91

6-Methylsulfanyl-1H-indole-2-carboxylic acid and 4'-aminoacetophenone were combined according to Method B (steps (i) and (ii)), to obtain the product after HPLC purification. $t_R$ 14.99 min (10-90% $CH_3CN$ in $H_2O$, 20 min); MS (m/z) 381 (MH$^+$).

Example 6.35

Synthesis of Compound 92

6-Ethylamino-1H-indole-2-carboxylic acid and 4'-aminoacetophenone were combined according to Method B (steps (i) and (ii)), to obtain the product after HPLC purification. $t_R$ 16.82 min (10-35%, $CH_3CN$ in $H_2O$, 20 min); MS (m/z) 378 (MH$^+$).

Example 6.36

Synthesis of Compound 93

6-Methyl-1H-indole-2-carboxylic acid and 4'-aminoacetophenone were combined according to Method B (steps (i) and (ii)), to obtain the product after HPLC purification. $t_R$ 14.93 min (10-90% $CH_3CN$ in $H_2O$, 20 min); MS (m/z) 349 (MH$^+$).

Example 6.37

Synthesis of Compound 94

6-Chloro-1H-indole-2-carboxylic acid and 4'-aminoacetophenone were combined according to Method B (steps (i) and (ii)), to obtain the product after HPLC purification. $t_R$ 14.78 min (10-90% $CH_3CN$ in $H_2O$, 20 min); MS (m/z) 369 (MH$^+$).

Example 6.38

Synthesis of Compound 99

6-Amino-5-methoxy-1H-indole-2-carboxylic acid and 4'-aminoacetophenone were combined according to Method B (steps (i) and (ii)), to obtain the product after HPLC purification. $t_R$ 14.37 min (10-40% $CH_3CN$ in $H_2O$, 20 min); MS (m/z) 380 (MH$^+$).

Example 6.39

Synthesis of Compound 105

5-Methoxy-1H-indole-2-carboxylic acid and 6-Amino-3,4-dihydro-2H-naphthalen-1-one were combined according to Method B (steps (i) and (ii)), to obtain the product after HPLC purification. $t_R$ 14.40 min (10-90% $CH_3CN$ in $H_2O$, 20 min); MS (m/z) 391 (MH$^+$)

Example 6.40

Synthesis of Compound 110

5-Methoxy-1H-indole-2-carboxylic acid and 5-Amino-indan-1-one were combined according to Method B (steps (i) and (ii)), to obtain the product after HPLC purification. $t_R$ 17.72 min (25-45% $CH_3CN$ in $H_2O$, 20 min); MS (m/z) 377 (MH$^+$).

Example 6.41

Synthesis of Compound 72

5-Acetyl-1H-indole-2-carboxylic acid and 4-(2-Methyl-[1,3]dithian-2-yl)-phenylamine prepared as described the literature (Vijay Kumar and Sukh, *Dev. Tetrahedron Letters*, 1983; 24(12), 1289-1292) were combined according to Method B (steps (i) and (ii)). After 1,3-dithiane deprotection by the DMP oxidation procedure (Langille, N. F.; Dakin, L. A.; Panek, J. S. *Org. Lett.* 2003; 5(4); 575-578), the pure monohydrozone was obtained by HPLC purification. $t_R$ 18.31 min (15-50% $CH_3CN$ in $H_2O$, 25 min); MS (m/z) 377 (MH$^+$).

Example 6.42

Synthesis of Compound 80

5-Acetyl-1H-indole-2-carboxylic acid and 5-amino-1H-indole were combined according to Method B (steps (i) and (ii)) to obtain the pure product after HPLC purification. $t_R$ 17.06 min (15-50% $CH_3CN$ in $H_2O$, 20 min); MS (m/z) 374 (MH$^+$).

Example 6.43

Synthesis of Compound 81

5-Acetyl-1H-indole-2-carboxylic acid and 6-amino-1H-indole were combined according to Method B (steps (i) and (ii)) to obtain the pure product after HPLC purification. $t_R$ 16.36 min (20-50% $CH_3CN$ in $H_2O$, 20 min); MS (m/z) 374 (MH$^+$).

Example 6.44

Synthesis of Compound 101

5-Acetyl-1H-indole-2-carboxylic acid and 6-amino-quinoline were combined according to Method B (steps (i) and (ii)) to obtain the pure product after HPLC purification. $t_R$ 13.77 min (10-50% $CH_3CN$ in $H_2O$, 20 min); MS (m/z) 386 (MH$^+$)

Example 6.45

Synthesis of Compound 102

5-Acetyl-1H-indole-2-carboxylic acid and 2-amino-4-methylpyridine were combined according to Method B (steps (i) and (ii)) to obtain the pure product after HPLC purification. $t_R$ 14.92 min (10-40% $CH_3CN$ in $H_2O$, 20 min); MS (m/z) 350 (MH$^+$).

Example 6.46

Synthesis of Compound 103

5-Acetyl-1H-indole-2-carboxylic acid and 2-amino-5-methylpyridine were combined according to Method B (steps (i) and (ii)) to obtain the pure product after HPLC purification. $t_R$ 15.17 min (10-40% $CH_3CN$ in $H_2O$, 20 min); MS (m/z) 350 (MH$^+$).

Example 6.47

Synthesis of Compound 104

5-Acetyl-1H-indole-2-carboxylic acid and 2-amino-pyridine were combined according to Method B (steps (i) and (ii)) to obtain the pure product after HPLC purification. $t_R$ 15.37 min (15-25% $CH_3CN$ in $H_2O$, 20 min); MS (m/z) 336 (MH$^+$).

Example 6.48

Synthesis of Compound 108

5-Acetyl-1H-indole-2-carboxylic acid and 4-amino-indole were combined according to Method B (steps (i) and (ii)) to obtain the pure product after HPLC purification. $t_R$ 15.57 min (10-60% $CH_3CN$ in $H_2O$, 20 min); MS (m/z) 374 (MH$^+$).

Example 6.49

Synthesis of Compound 109

5-Acetyl-1H-indole-2-carboxylic acid and 5-amino-2-methyl-1H-indole were combined according to Method B (steps (i) and (ii)) to obtain the pure product after HPLC purification. $t_R$ 15.57 min (10-60% $CH_3CN$ in $H_2O$, 20 min); MS (m/z) 388 (MH$^+$).

Example 6.50

Synthesis of Compound 111

5-Acetyl-1H-indole-2-carboxylic acid and 3-amino-aniline were combined according to Method B (steps (i) and (ii)) to obtain the pure product after HPLC purification. $t_R$ 11.95 min (10-60% $CH_3CN$ in $H_2O$, 20 min); MS (m/z) 350 (MH$^+$).

Example 6.51

Synthesis of Compounds 112 and 113

5-Butyryl-1H-indole-2-carboxylic acid and 6-amino-1H-indole were combined according to g Method B (steps (i) and (ii)) to obtained two pure isomers after HPLC purification. 112: $t_R$ 14.40 min, MS (m/z) 406 (MH$^+$) and 113: $t_R$ 16.73 min (30-50% $CH_3CN$ in $H_2O$, 20 min); MS (m/z) 406 (MH$^+$).

Example 6.52

Synthesis of Compound 114

5-Acetyl-1H-indole-2-carboxylic acid and 4-amino-aniline were combined according to Method B (steps (i) and (ii)) to obtain the pure product after HPLC purification. $t_R$ 12.47 min (10-40% $CH_3CN$ in $H_2O$, 20 min); MS (m/z) 350 (MH$^+$).

Example 6.53

Synthesis of Compound 115

5-Acetyl-1H-indole-2-carboxylic acid and 4-Amino-benzamide were combined according to Method B (steps (i) and (ii)) to obtain the pure product after HPLC purification. $t_R$ 16.99 min (10-40% $CH_3CN$ in $H_2O$, 20 min); MS (m/z) 378 (MH$^+$).

Example 6.54

Synthesis of Compound 119

5-Acetyl-1H-indole-2-carboxylic acid and 7-amino-quinoline were combined according to Method B (steps (i) and (ii)) to obtain the pure product after HPLC purification. $t_R$ 12.83 min (10-60% $CH_3CN$ in $H_2O$, 20 min); MS (m/z) 386 (MH$^+$).

Example 6.55

Synthesis of Compound 120

5-Acetyl-1H-indole-2-carboxylic acid and 4-(4-Aminophenyl)-piperazine-1-carboxylic acid tert-butyl ester were combined according to Method B (steps (i) and (ii)). After Boc deprotection with 20% TFA in DCM (30 min, rt) the pure product was obtained as TFA salt after HPLC purification. $t_R$ 13.37 min (10-40% $CH_3CN$ in $H_2O$, 20 min); MS (m/z) 419 ($MH^+$).

Example 6.56

Synthesis of Compound 121

5-Acetyl-1H-indole-2-carboxylic acid and 5-amino-benzoimidazole were combined according to Method B (steps (i) and (ii)) to obtain the pure product after HPLC purification. $t_R$ 14.71 min (10-40% $CH_3CN$ in $H_2O$, 20 min); MS (m/z) 375 ($MH^+$).

Example 6.57

Synthesis of Compound 122

5-Acetyl-1H-indole-2-carboxylic acid and [1,6]naphthyridin-2-ylamine were combined according to Method B (steps (i) and (ii)) to obtain the pure product after HPLC purification. $t_R$ 15.37 min (10-40% $CH_3CN$ in $H_2O$, 20 min); MS (m/z) 387 ($MH^+$).

Example 6.58

Synthesis of Compounds 123 and 124

A. Preparation of 5-(3-Methyl-butyryl)-1H-indole-2-carboxylic acid (Froshauer, S. A.; Goldstein, S. W.; Stirtan, W. G. U.S. Pat. No. 5,981,762): 3-Bromo-1H-indole-2-carboxylic acid ethyl ester (536 mg, 2.0 mmol), prepared as previously described (Elliott, J. D.; Leber, J. D.; Thompson, S. K.; Halbert, S. M. U.S. Pat. No. 5,684,032) was dissolved in nitromethane (10 mL) and cooled to 0° C. $AlCl_3$ was added to the flask. Then a solution of isovaleryl chloride (0.295 mL, 2.4 mmol) in nitromethane (2 mL) was added dropwise to the flask. The mixture was allowed to come to room temperature and stirred for 18 hours. The mixture was then cooled to 0° C. 20 mL ice-water was added and extracted with $CH_2Cl_2$ (4×20 mL). The combined organic phase was washed with saturated brine (20 mL), 1N $NaHCO_3$ (20 mL) and saturated brine (2×20 mL), Dried over anhydrous $Na_2SO_4$, filtered, and concentrated under vacuum to give yellow solid. It was then purified by flash column chromatography eluted with hexane:ethyl acetate (6:1) to give 3-Bromo-5-(3-methyl-butyryl)-1H-indole-2-carboxylic acid ethyl ester (468 mg, 67%) as light yellow solid.
$^1$HNMR (300 MHz, DMSO-$d_6$) δ12.60 (brs, 1H); 8.20 (d, J=1.2 Hz, 1H), 7.97 (dd, J=8.7, 1.8 Hz, 1H), 7.57 (d, J=8.7 Hz, 1H), 4.41 (q, J=6.9 Hz, 2H), 2.98 (d, J=6.9 Hz, 2H), 2.20 (m, 1H), 1.39 (t, J=6.9 Hz, 3H), 0.97 (d, J=6.9 Hz, 6H). EIMS m/z 352.0 ($M^++H$).

B. To the mixture of 3-Bromo-5-(3-methyl-butyryl)-1H-indole-2-carboxylic acid ethyl ester (408 mg, 1.1 mmol), ammonium formate (10 mg, 1.7 mmol), and 10% Pd/C (200 mg) was added DMF (5 mL) and water (0.625 mL). The mixture was slightly shaked at room temperature for 70 minutes and then filtered through celite. The solvent was evaporated under vacuum to give 5-(3-Methyl-butyryl)-1H-indole-2-carboxylic acid ethyl ester as light yellow liquid as crude product with the purity of 90%; E1-MS m/z 274.1 ($M^++H$). The crude ethyl ester was dissolved in dioxane (10 mL), Then a solution of $LiOH.H_2O$ (195 mg, 4.6 mmol) in water (5 mL) was added to the flask. The mixture was stirred at room temperature for 2 days. Dioxane was stripped under vacuum. 10 mL water was added and extracted with $CH_2Cl_2$. Then the aqueous phase was acidified with 6N HCl and extracted with $CH_2Cl_2$. The $CH_2Cl_2$ phase was then washed with saturated brine and dried over anhydrous $Na_2SO_4$. Solvent was removed under vacuum to give 5-(3-Methyl-butyryl)-1H-indole-2-carboxylic acid (250 mg, 88% for two steps) as white solid. EIMS m/z 246.1 ($M^++H$) (lab-ref: YS-053-141).

C. 5-(3-Methyl-butyryl)-1H-indole-2-carboxylic acid and 6-amino-1H-indole were combined according to Method B (steps (i) and (ii)) to obtained two isomers after HPLC purification. 123: $t_R$ 14.85 min (20-80% $CH_3CN$ in $H_2O$, 20 min); MS (m/z) 416 ($MH^+$); 124: $t_R$ 16.23 min (20-80% $CH_3CN$ in $H_2O$, 20 min); MS (m/z) 416 ($MH^+$).

Example 6.59

Synthesis of Compound 125

5-Acetyl-1H-indole-2-carboxylic acid and 6-amino-2-methyl-quinoline were combined according to Method B (steps (i) and (ii)) to obtain the pure product after HPLC purification. $t_R$ 12.63 min (10-60% $CH_3CN$ in $H_2O$, 20 min); MS (m/z) 400 ($MH^+$).

Example 6.60

Synthesis of Compound 116

1,3-Bis-(4-acetyl-phenyl)-urea, made from 4-acetyl phenylisocyanate and 4-acetyl phenylamine, and N-hydroxy-N'-aminoguanidine PTSA salt, prepared as described in the literature (A. W. Tai, E. J Lien, E. C. Moore, Y. Chun, and J Roberts *J. Med. Chem.* 1983, 26, 1326-1329.) were combined according to Method A, to obtain after purification by reverse phase HPLC the product $t_R$ 15.0 min (20-60% $CH_3CN$ in $H_2O$, 25 min); MS (m/z) 220 ($M^+/2$), 440 ($M^+$).

Example 6.61

Synthesis of Compound 117

5-Methoxy-1H-indole-2-carboxylic acid (4-acetyl-phenyl)-amide, made from 5-Methoxy-1H-indole-2-carboxylic acid and 4-acetyl phenylamine, and N-hydroxy-N'-aminoguanidine PTSA salt, prepared as described in the literature (A. W. Tai, E. J Lien, E. C. Moore, Y. Chun, and J Roberts *J. Med. Chem.* 1983, 26, 1326-1329) were combined according to Method B, to obtain the pure product after purification by reverse phase HPLC: $t_R$ 20.5 min (20-60% $CH_3CN$ in $H_2O$, 25 min); MS (m/z) 381 ($MH^+$).

Example 6.62

Synthesis of Compound 118

7-Nitro-1H-indole-2-carboxylic acid (4-acetyl-phenyl)-amide, made from 7-nitro-1H-indole-2-carboxylic acid and 4-acetyl phenylamine by following the standard procedures and N-hydroxy-N'-aminoguanidine PTSA salt, prepared as described in the literature (A. W. Tai, E. J. Lien, E. C. Moore, Y. Chun, and J. Roberts *J. Med. Chem.* 1983, 26, 1326-1329) were combined according to Method B, to obtain the pure product after HPLC purification: $t_R$ 22.2 min (20-60% $CH_3CN$ in $H_2O$, 25 min); MS (m/z) 396 ($MH^+$).

Example 6.63

Synthesis of Compound 75

7-Methoxy-1H-indole-2-carboxylic acid and 4-amino acetophenone were combined according to Method B (steps (i) and (ii)) to obtain the pure product after HPLC purification. $t_R$ 17.30 min (20-60% $CH_3CN$ in $H_2O$, 25 min); MS (m/z) 365 ($MH^+$).

Example 6.64

Synthesis of Compound 77

7-Amino-1H-indole-2-carboxylic acid and 4-amino acetophenone were combined according to Method B (steps (i) and (ii)) to obtain the pure product after HPLC purification. $t_R$ 11.61 min (10-60% $CH_3CN$ in $H_2O$, 20 min); MS (m/z) 350 ($MH^+$).

Example 6.65

Synthesis of Compound 79

5-Oxo-5,6,7,8-tetrahydro-naphthalene-2-carboxylic acid and 4-amino acetophenone were combined according to Method B (steps (i) and (ii)) to obtain the pure product after HPLC purification: $t_R$ 17.61 min (10-40% $CH_3CN$ in $H_2O$, 20 min); MS (m/z) 420 ($MH^+$).

Example 6.66

Synthesis of Compound 82

6-Methoxy-benzothiazole-2-carboxylic acid and 4-amino acetophenone were combined according to Method B (steps (i) and (ii)) to obtain the pure product after HPLC purification: $t_R$ 16.51 min (10-80% $CH_3CN$ in $H_2O$, 20 min); MS (m/z) 383 ($MH^+$).

Example 6.67

Synthesis of Compound 83

6-Amino-1H-indole-2-carboxylic acid and 4-amino acetophenone were combined according to Method B (steps (i) and (ii)) to obtain the pure product after HPLC purification: $t_R$ 10.50 min (10-60% $CH_3CN$ in $H_2O$, 20 min); MS (m/z) 350 ($MH^+$).

Example 6.68

Synthesis of Compound 84

7-Nitro-1H-indole-2-carboxylic acid and 4-amino-2-methylacetophenone were combined according to Method B (steps (i) and (ii)) to obtain the pure product after HPLC purification: $t_R$ 15.97 min (15-70% $CH_3CN$ in $H_2O$, 20 min); MS (m/z) 394 ($MH^+$).

Example 6.69

Synthesis of Compound 85

7-Trifluoromethyl-1H-indole-2-carboxylic acid and 4-aminoacetophenione were combined according to Method B (steps (i) and (ii)) to obtain the pure product after HPLC purification: $t_R$ 13.43 min (20-80% $CH_3CN$ in $H_2O$, 15 min); MS (m/z) 403 ($MH^+$).

Example 6.70

Synthesis of Compound 87

5-Fluoro-1H-indole-2-carboxylic acid and 4-aminoacetophenone were combined according to Method B (steps (i) and (ii)) to obtain the pure product after HPLC purification: $t_R$ 13.49 min (20-65% $CH_3CN$ in $H_2O$, 15 min); MS (m/z) 353 ($MH^+$).

Example 6.71

Synthesis of Compound 90

6-Propoxy-1H-indole-2-carboxylic acid and 4-aminoacetophenone were combined according to Method B (steps (i) and (ii)) to obtain the pure product after HPLC purification: $t_R$ 16.05 min (10-90% $CH_3CN$ in $H_2O$, 20 min); MS (m/z) 393 ($MH^+$).

Example 6.72

Synthesis of Compound 95

7-Propoxy-1H-indole-2-carboxylic acid and 4-aminoacetophenone were combined according to Method B (steps (i) and (ii)) to obtain the pure product after HPLC purification: $t_R$ 17.42 min (30-70% $CH_3CN$ in $H_2O$, 20 min); MS (m/z) 428 ($MH^+$).

Example 6.73

Synthesis of Compound 96

7-Nitro-1H-indole-2-carboxylic acid and 5-Amino-indanone were combined according to Method B (steps (i) and (ii)) to obtain the pure product after HPLC purification: $t_R$ 18.62 min (10-65% $CH_3CN$ in $H_2O$, 20 min); MS (m/z) 392 ($MH^+$).

Example 6.74

Synthesis of Compound 98

6-Acetylamino-5-methoxy-1H-indole-2-carboxylic acid and 4-aminoacetophenone were combined according to Method B (steps (i) and (ii)) to obtain the pure product after HPLC purification: $t_R$ 13.17 min (10-80% $CH_3CN$ in $H_2O$, 20 min); MS (m/z) 422 ($MH^+$).

Example 6.75

Synthesis of Compound 97

4-Methyl-1H-indole-2-carboxylic acid and 4-aminoacetophenone were combined according to Method B (steps (i) and (ii)) to obtain the pure product after HPLC purification: $t_R$ 16.12 min (10-80% $CH_3CN$ in $H_2O$, 20 min); MS (m/z) 422 ($MH^+$).

Example 6.76

Synthesis of Compound 100

1H-Benzoimidazole-2-carboxylic acid and 4-aminoacetophenone were combined according to Method B (steps (i)

and (ii)) to obtain the pure product after HPLC purification: $t_R$ 13.27 min (10-80% $CH_3CN$ in $H_2O$, 20 min); MS (m/z) 336 (MH$^+$).

Example 6.77

Synthesis of Compound 106

Imidazo[1,2-a]pyridine-2-carboxylic acid and 4-aminoacetophenone were combined according to Method B (steps (i) and (ii)) to obtain the pure product after HPLC purification: $t_R$ 15.99 min (10-30% $CH_3CN$ in $H_2O$, 20 min); MS (m/z) 336 (MH$^+$).

Example 6.78

Synthesis of Compound 107

3H-Benzo[e]indole-2-carboxylic acid and 4-aminoacetophenone were combined according to Method B (steps (i) and (ii)) to obtain the pure product after HPLC purification: $t_R$ 15.75 min (20-80% $CH_3CN$ in $H_2O$, 20 min); MS (m/z) 385 (MH$^+$).

Example 6.79

Synthesis of Compound 126

5-Acetyl-1H-indole-2-carboxylic acid and 6-amino isoquinoline were combined according to Method B (steps (i) and (ii)) to obtained the pure product after HPLC purification. $t_R$ 16.67 min (10-40% $CH_3CN$ in $H_2O$, 20 min); MS (m/z) 386 (MH$^+$).

Example 6.80

Synthesis of Compound 127

5-Acetyl-1H-indole-2-carboxylic acid and 4-imidazol-1-yl-phenylamine were combined according to Method B (steps (i) and (ii)) to obtained the pure product after HPLC purification. $t_R$ 15.78 min (10-40% $CH_3CN$ in $H_2O$, 20 min); MS (m/z) 401 (MH$^+$).

Example 6.81

Synthesis of Compound 128

5-Acetyl-1H-indole-2-carboxylic acid and 4-piperidin-1-yl-phenylamine were combined according to Method B (steps (i) and (ii)) to obtained the pure product after HPLC purification. $t_R$ 12.34 min (10-60% $CH_3CN$ in $H_2O$, 20 min); MS (m/z) 434 (MH$^+$).

Example 6.82

Synthesis of Compound 129

5-Carbamoyl-1H-indole-2-carboxylic acid and 1-(4-aminophenyl)-ethanone were combined according to Method B (steps (i) and (ii)) to obtained the pure product after HPLC purification. $t_R$ 16.00 min (10-40% $CH_3CN$ in $H_2O$, 20 min); MS (m/z) 394 (MH$^+$).

Example 6.83

Synthesis of Compound 130

5-(3-Methyl-butyryl)-1H-indole-2-carboxylic acid and 1-(4-aminophenyl)-ethanone were combined according to Method B (steps (i) and (ii)) to obtained the pure product after HPLC purification. $t_R$ 16.25 min (10-60% $CH_3CN$ in $H_2O$, 20 min); MS (m/z) 475 (MH$^+$).

Compounds can be assayed for their activity according to the following procedures.

Example 6.84

High-Throughput Chk2 Screening Assay

Compounds can be screened for Chk2 inhibitory activity using a high-throughput screening assay based in the immobilized metal ion affinity-based fluorescence polarization (IMAP) assay developed by Molecular Devices. This assay is based on the high affinity binding of phosphate by immobilized metal (MIII) coordination complexes on nanoparticles. A fluorescein-labeled peptide substrate is used as the substrate for the kinase activity of Chk2 in the assay. The IMAP binding reagent stops the kinase reaction. The binding of the binding reagent results in a change in the rate of molecular motion of the peptide and causes an increase in the fluorescence polarization value observed for the fluorescein label attached to the end of the peptide. Thus, inhibition of Chk2 would result in a decrease in fluorescence polarization compared to control.

A specific protocol for screening Compounds for Chk2 inhibitory activity follows.

6×His-Chk2 can be expressed and purified using the following protocol.

Day 1: Add 1 µl of purified Chk2 plasmid to one vial of BL21 Star cells (Invitrogen); leave on ice for 15-30 minutes; heatshock at 42° C. for 30 seconds; return to ice for 2-3 minutes; add 250 µl SOC and shake at 37° C. for one hour; divide the bacterial suspension among four LB plates with 50 µg/ml ampicillin (if there are pools of media on the plates, place them, uncovered, in tissue culture hood for about 15 minutes to dry); incubate plates overnight at 37° C.

Day 2: Pour 200 ml LB into a 2 L flask and add ampicillin to 100 µg/ml (400 µl of 50 mg/ml stock ampicillin); scrap cells from all four plates and add to 200 ml culture; shake culture at 37° C. for about two hours; prepare 4 baffled flasks with 1 L LB plus 100 µg/ml ampicillin (2 ml/L) and prewarm at 37° C. for about one hour; dilute 50 ml of starter culture into each flask; shake at 37° C. for about 2 hours or until OD600=0.6-0.8; add 0.5 ml of IPTG (stock=1M) to each flask; lower temp to ~20° C. and shake for 2.5 hours; pour cultures into 1 L centrifuge bottles; spin at 6500×g for 10 minutes; prepare 4 (50 ml) centrifuge tubes with 10 ml Buffer A (20 mM Tris, pH 8.0; 500 mM NaCl; 0.1% Tween 20) and one tablet mini-Complete Protease inhibitors (Roche); place in ice bucket; decant supernatants into culture flasks and add ~100 ml bleach to each flask; pour 10 ml of Buffer A into each centrifuge bottle and pipette/stir/vortex until entire pellet is suspended; transfer bacterial suspension back to prechilled 50 ml centrifuge tube; add a few grains of lysozyme (~50 mg); vortex well; and leave on ice for ~10 min; freeze bacterial suspensions at −80° C.

Day 3: Place one tube of frozen cell suspension in 37° C. water bath to thaw; shake frequently and minimize warming of sample; place thawed tube of lysate in water:ice bath; sonicate 6× for 30 sec; allow the sample to cool on ice for at least one minute between pulses (more if needed); add imidazole to 10 mM (100 µl for 20 ml of lysate); centrifuge at 50,000×g for 30 minutes at 4° C.; place clean 50 ml centrifuge tube on ice to chill; if crude column is not used, attach 0.45 µm SFCA filter to 30 ml syringe from which plunger has been removed, gently decant supernatant from centrifuge tube into syringe barrel, and carefully push lysate through filter into pre-chilled centrifuge tube, changing filters as necessary; place centrifuge tube in holder on FPLC and insert sample line S1; run protocol (Equilibrate 1 ml HisTrap FF column with 5 volumes 1% Buffer B (20 mM Tris, pH 8.0; 500 mM NaCl; 1 M imidazole, pH 8.0; 0.1% Tween 20), load sample, wash with 5 volumes of 1% Buffer B, wash with 10 volumes of 6% Buffer B, and elute with 10 vol gradient to 100% B); pool peaks of protein (usually about 3 ml per run); prepare 500 ml of Buffer C (20 mM Tris, pH 8.0; 50 mM NaCl; 0.25 mM EDTA, pH 8.0; 0.01% Tween 20) and 500 ml of Buffer D (20 mM Tris, pH 8.0; 50 mM NaCl; 0.25 mM EDTA, pH 8.0; 0.01% Tween 20; 1 mM DTT; 50% glycerol) and chill at 4° C.; prewet slide-a-lyzer cassette; use syringe to inject protein into pre-wet slide-a-lyzer cassette; dialyze against Buffer C for 2-3 hours at 4° C.; dialyze against Buffer D overnight at 4° C.

Day 4: Harvest sample and store at −20° C. and quantify using Biorad assay standardized with IgG.

A Compound is supplied at 1 mM in 0.5 µl DMSO on 384 well plates (such as Greiner or Corning). After thawing, 5 µl DMSO is added to the drug plate. The drug plate is then incubated for 10 minutes to solubilize the Compound. An additional 19.5 µl of reaction buffer (10× stock prepared using 100 mM Tris-HCl, 100 mM $MgCl_2$, 1% BSA, pH 7.2, stored at 4° C.)+1 mM DDT is added to bring the Compound to 4× final concentration. A positive control is also prepared at 4× final concentration. The following control wells are used: less enzyme control (all reagents except enzyme; 5 µl/well), less Compound control (all reagents except Compound; 5 µl/well), positive control (all reagents plus staurosporine at a final concentration of 5 µM; 5 µl/well).

Reagents are then added in the following order to give the following final concentration: 2.5 µl ATP/Chk2tide (Molecular Devices) (10 µM/100 nM final concentration), 1.25 µl Compound (5 µM final concentration inf 5.5% DMSO), and 1.25 µl Chk2 (1:500, 2.4 µg/mL final concentration).

Plates are covered and incubated at room temperature for 60 minutes.

IMAP binding reagent (Molecular Devices) is diluted 1:400 into binding buffer (Molecular Devices). 15 µl of this solution is then added to all wells and the plates are covered and incubated for 30 minutes.

Plates are read using a Tecan Ultra under the fluorescence polarization mode. Gain is set to the less enzyme and less Compound wells for each plate. Excitation 485 nm, emmission 535 nm, Z position 12519 and flashes 5 are used as settings. Raw data from the Tecan reader is imported into an access database for analysis.

Example 6.85

In Vitro Chk2 Kinase Assay

This assay is based on using $\gamma^{32}$P-labeled ATP to mediate phosphorylation of the target substrate and autophosphorylation of Chk2. Reactions are performed at 30° C. for appropriate times, then the samples have 2×SDS loading buffer added to quench the reaction. Samples are boiled for about 5 minutes and then subjected to SDS-PAGE.

Staurosporine is used as a positive control to confirm Chk2 inhibition.

Example 6.86

RSK2 Assay

Kinase activity was assayed using recombinant RSK2 enzyme, which was prepared as previously described (Clark et al., 2001, *EMBO J.* 20:3484-349). Fluoroscein-labeled peptide substrate for RSK2 and IMAP™ beads for capturing phosphorylated product were purchased from Molecular Devices. These reagents were combined in assay buffer containing 10 µM ATP and test Compounds in 384-well Greiner (Matrical) black plates (20 µL final volume). Phosphorylated substrate was detected by fluorescence polarization spectroscopy after binding to IMAP™ beads. Half-maximal inhibitory concentrations ($IC_{50}$) were read from concentration-response curves by linear interpolation.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A compound of the formula:

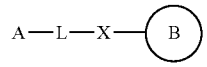

or a pharmaceutically acceptable salt or stereoisomer thereof, wherein:

ring B is

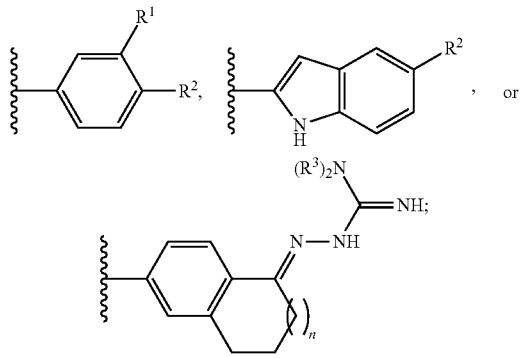

n is an integer selected from 0 and 1;

$R^1$ is H;

$R^2$ is —C(O)H, —C(O)$C_{1-6}$alkyl, —O$C_{1-6}$alkyl or a group selected from:

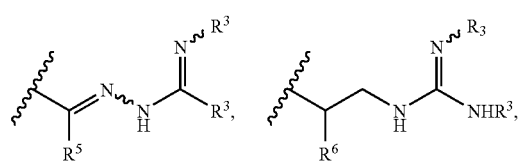

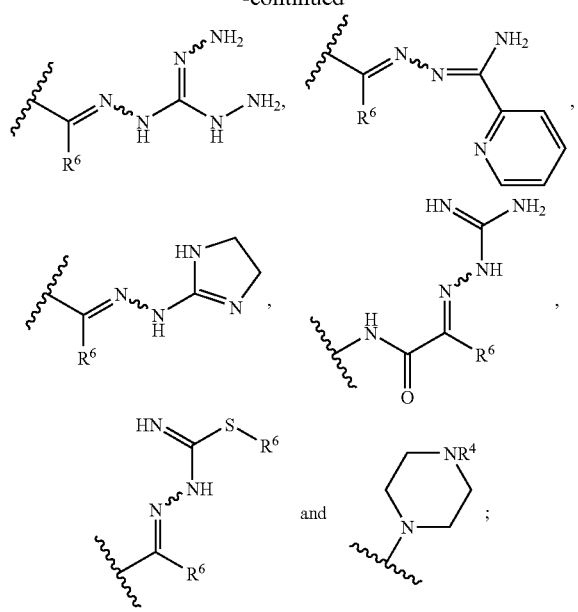

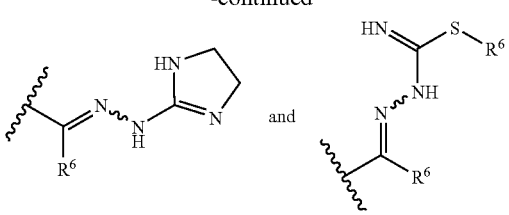

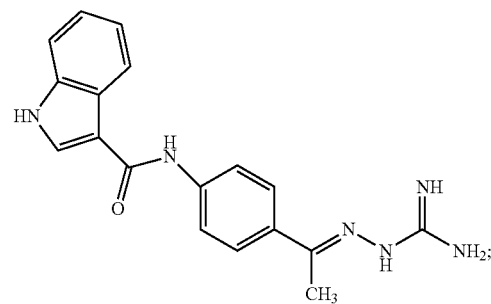

or R¹ and R² taken together with the atoms to which they are attached form a substituted or unsubstituted 5- or 6-membered cycloalkenyl ring; or R¹ and either R⁵ or R⁶ taken together with the atoms to which they are attached form a substituted or unsubstituted 5- or 6-membered cycloalkenyl ring;

X is —C(O)—N(R⁴)—, —N(R⁴)—C(O)—, —N(R⁴)—N(R⁴)—C(O)—, or —C(O)—N(R⁴)—N(R⁴);

L is a direct bond or C$_{1-6}$alkylene;

A is substituted or unsubstituted benzofuranyl, substituted or unsubstituted 1H-indole, substituted or unsubstituted 1H-indazole, or substituted or unsubstituted benzo[d]thiazolyl;

R³ is at each occurrence independently H, —OH, —OC$_{1-6}$alkyl, —NH₂, —NHOH, —NHR⁶, —SH or —S—C$_{1-6}$alkyl; and R⁴, R⁵ and R⁶ are at each occurrence independently H, substituted or unsubstituted aryl, substituted or unsubstituted C$_{3-10}$heteroaryl, substituted or unsubstituted C$_{3-10}$cycloalkyl, substituted or unsubstituted C$_{3-10}$heterocycloalkyl, or substituted or unsubstituted C$_{1-6}$alkyl, wherein either A is substituted with at least one of the following groups or R² is one of the following groups:

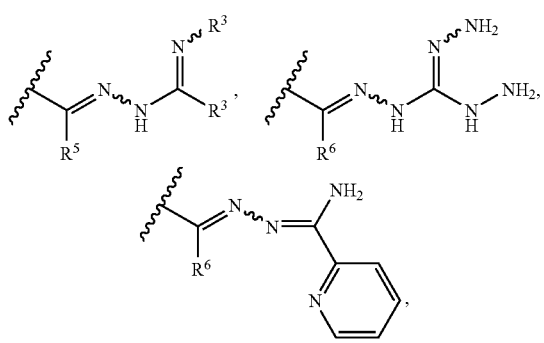

2. A compound of the formula:

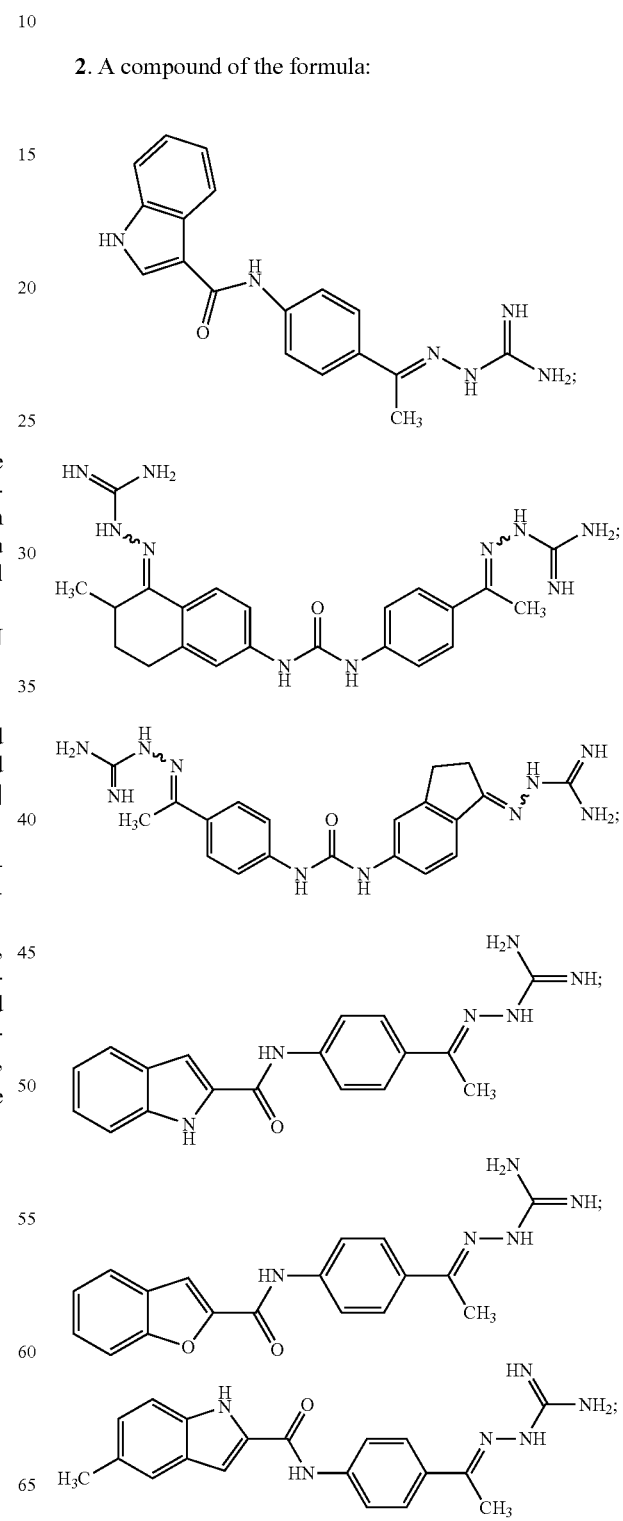

119
-continued
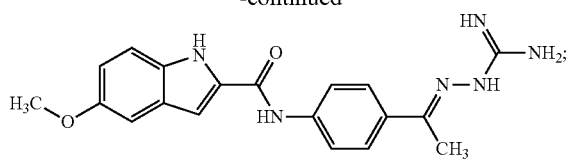
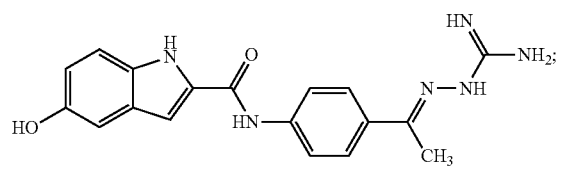
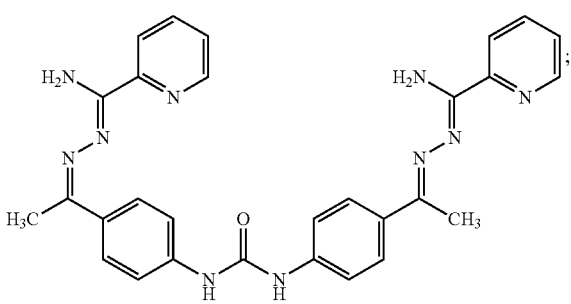
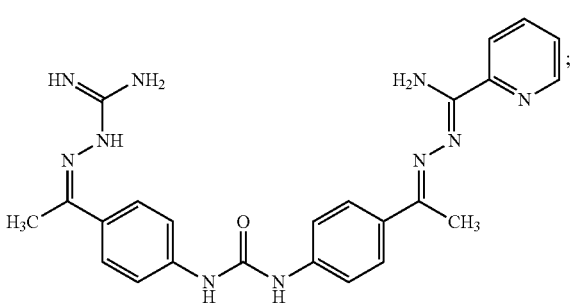
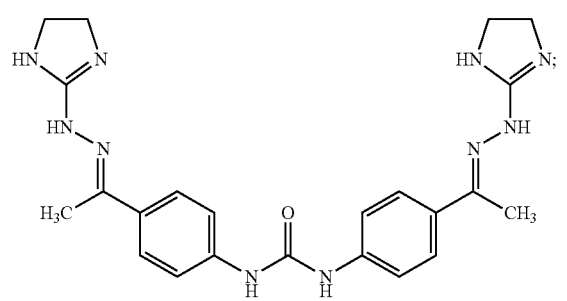
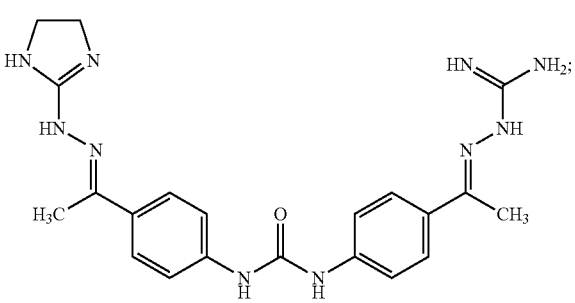
120
-continued
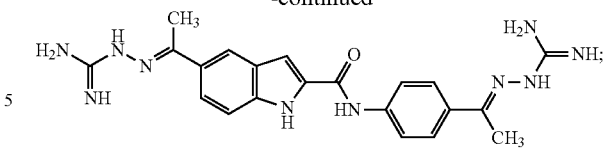
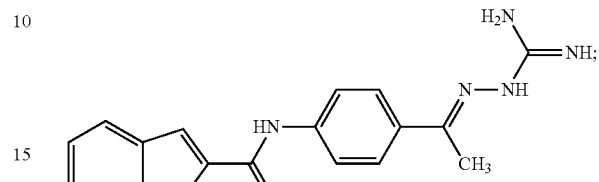
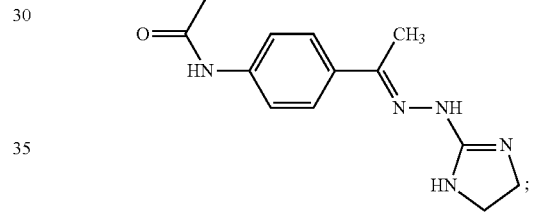
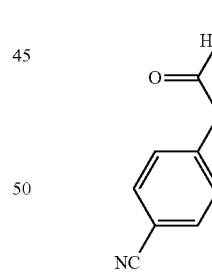
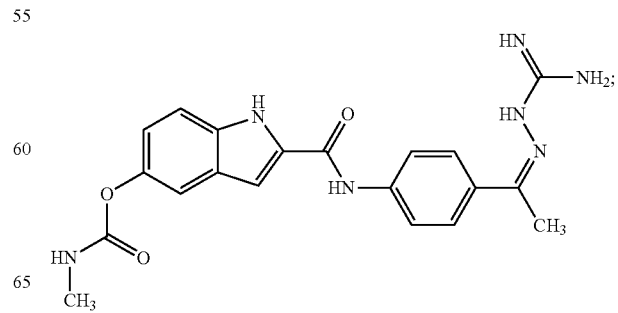

121
-continued
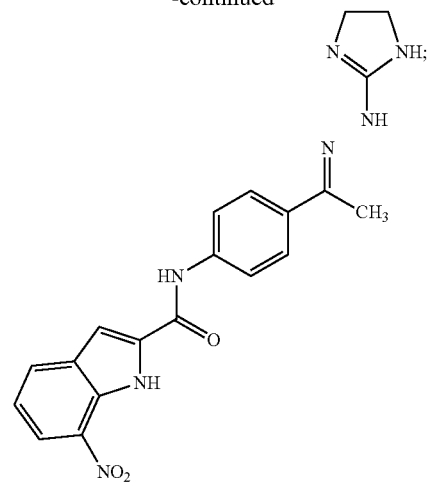
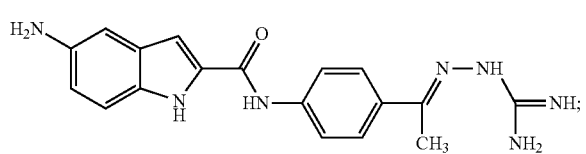
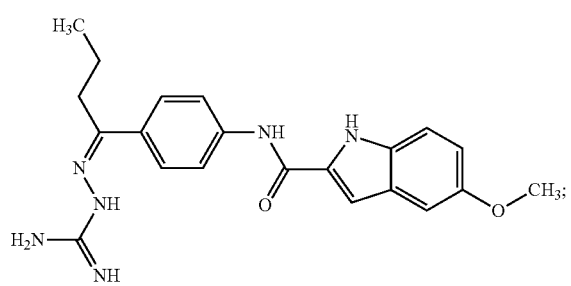
122
-continued
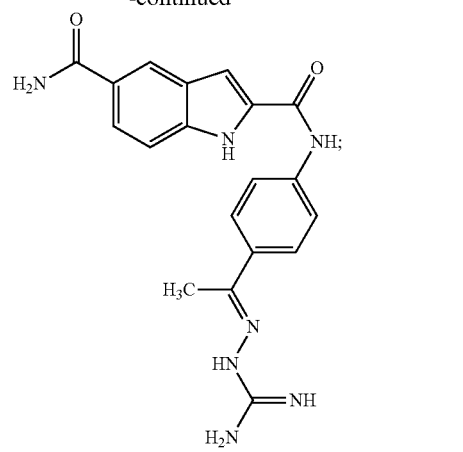
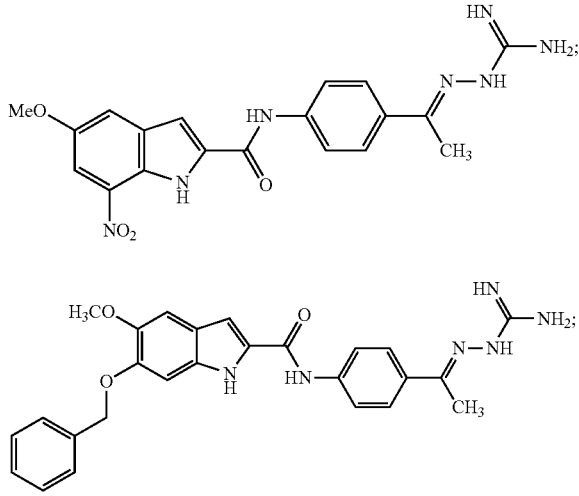
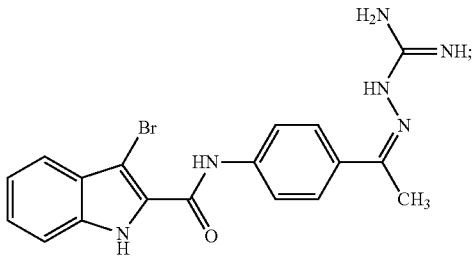
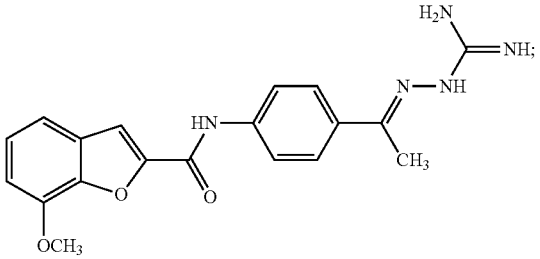
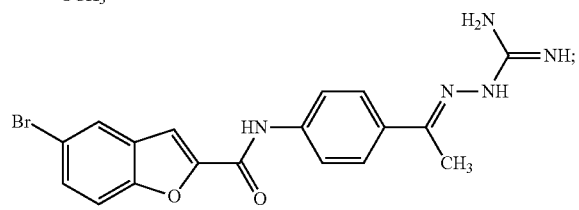

-continued
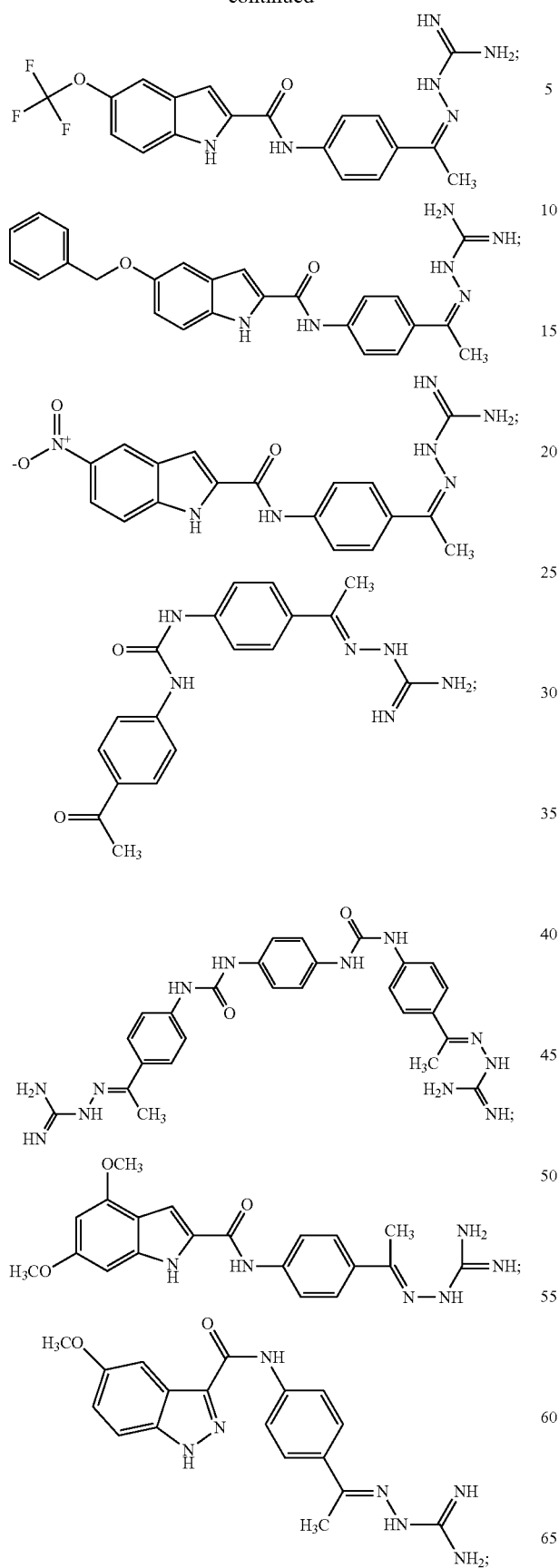
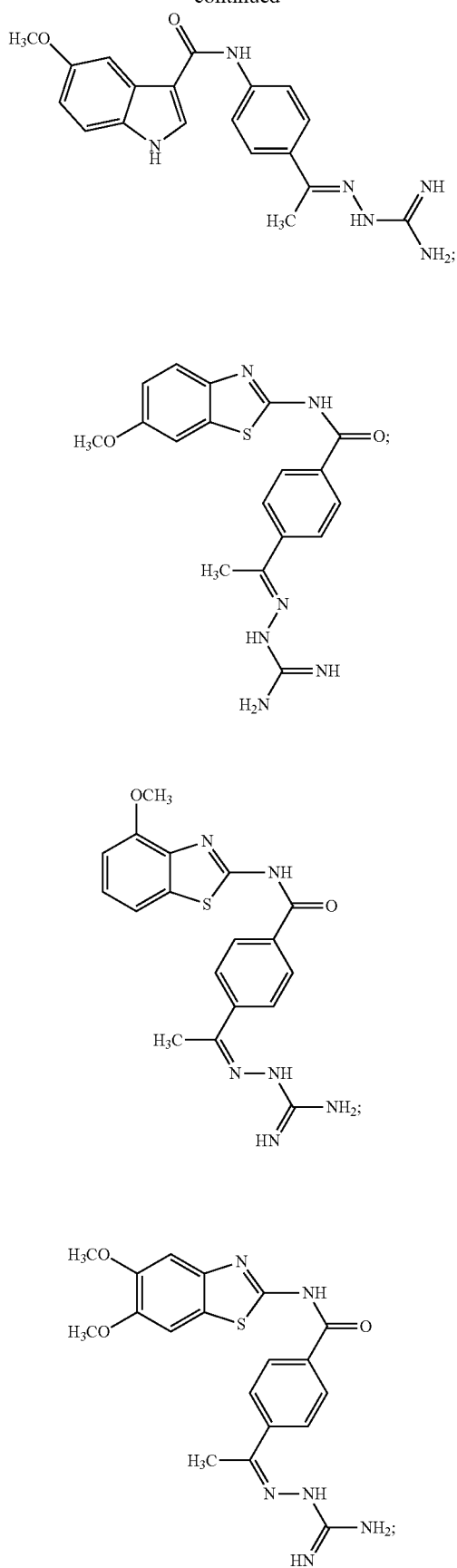

125
-continued
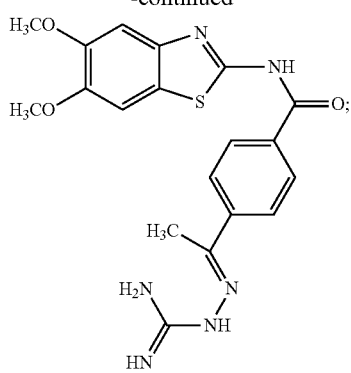
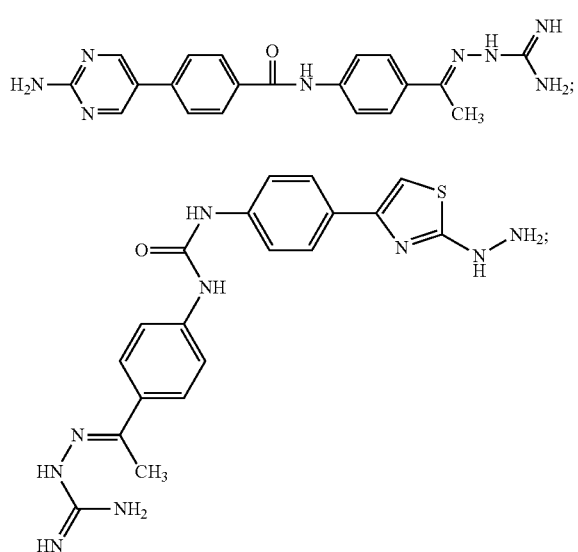
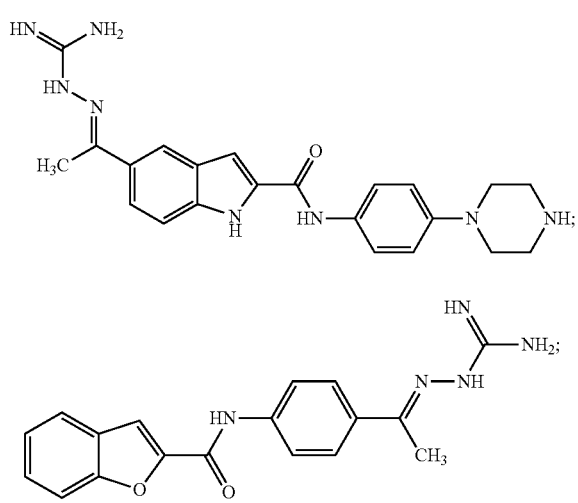
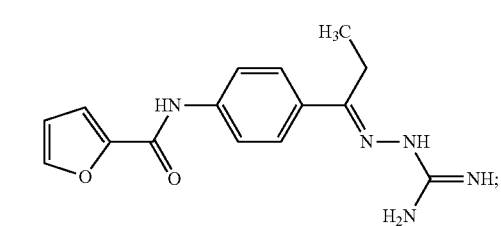
126
-continued
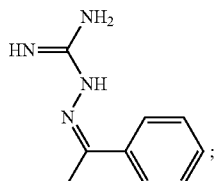
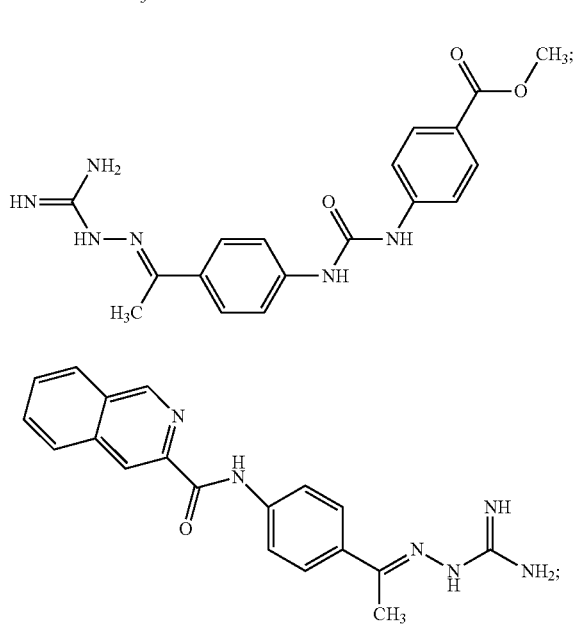
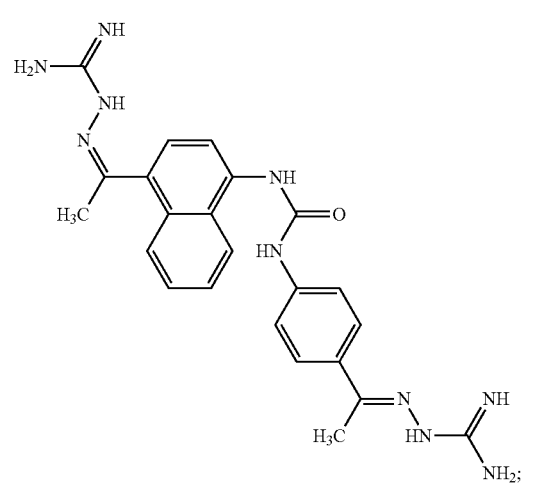
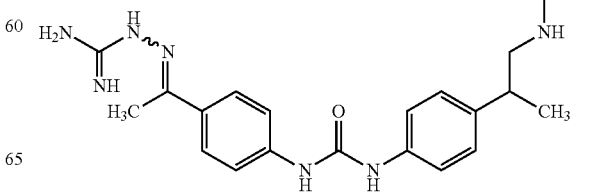

127
-continued
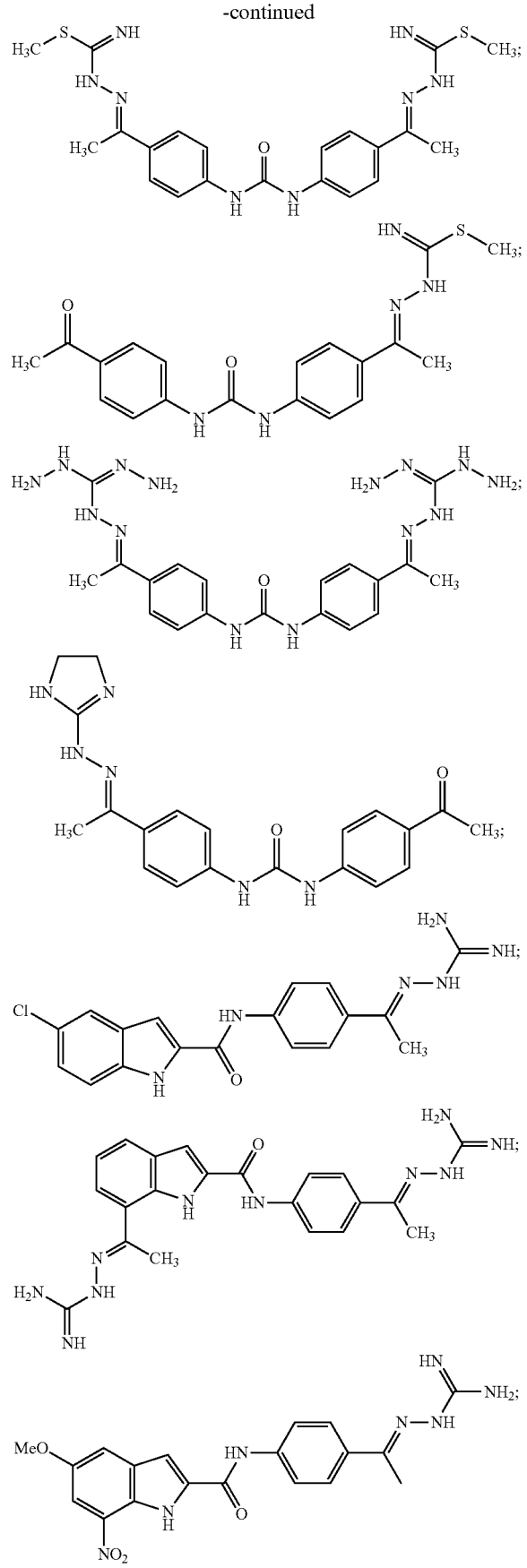
128
-continued
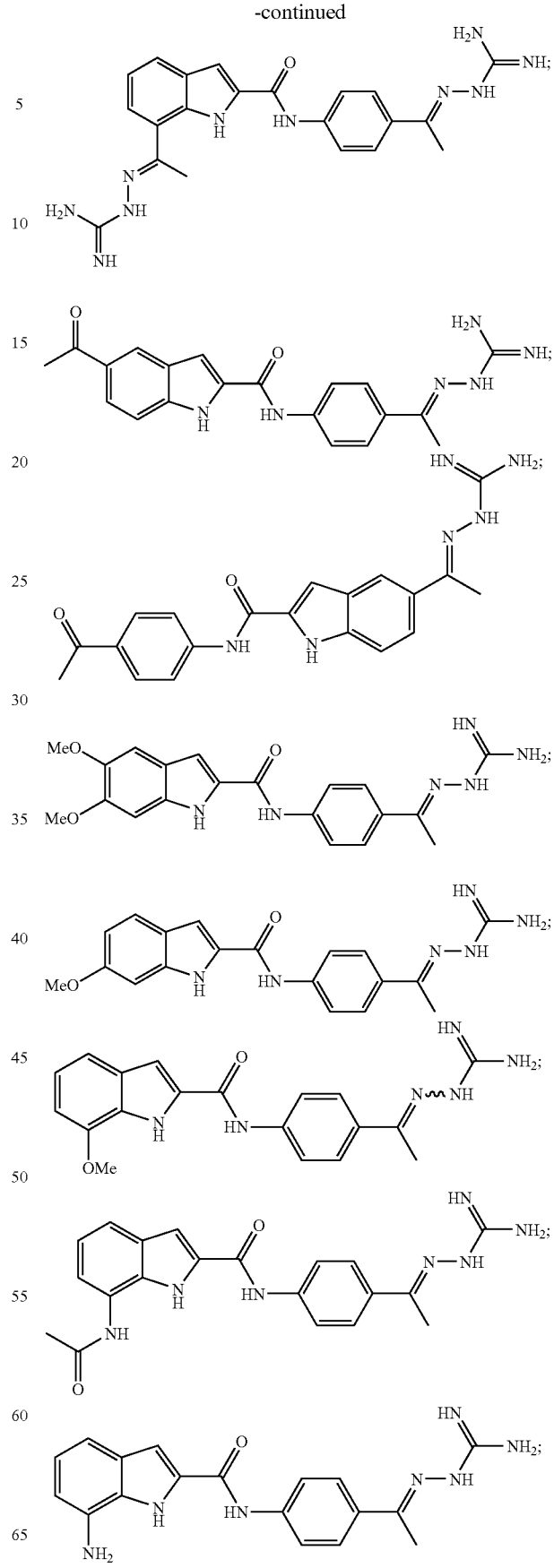

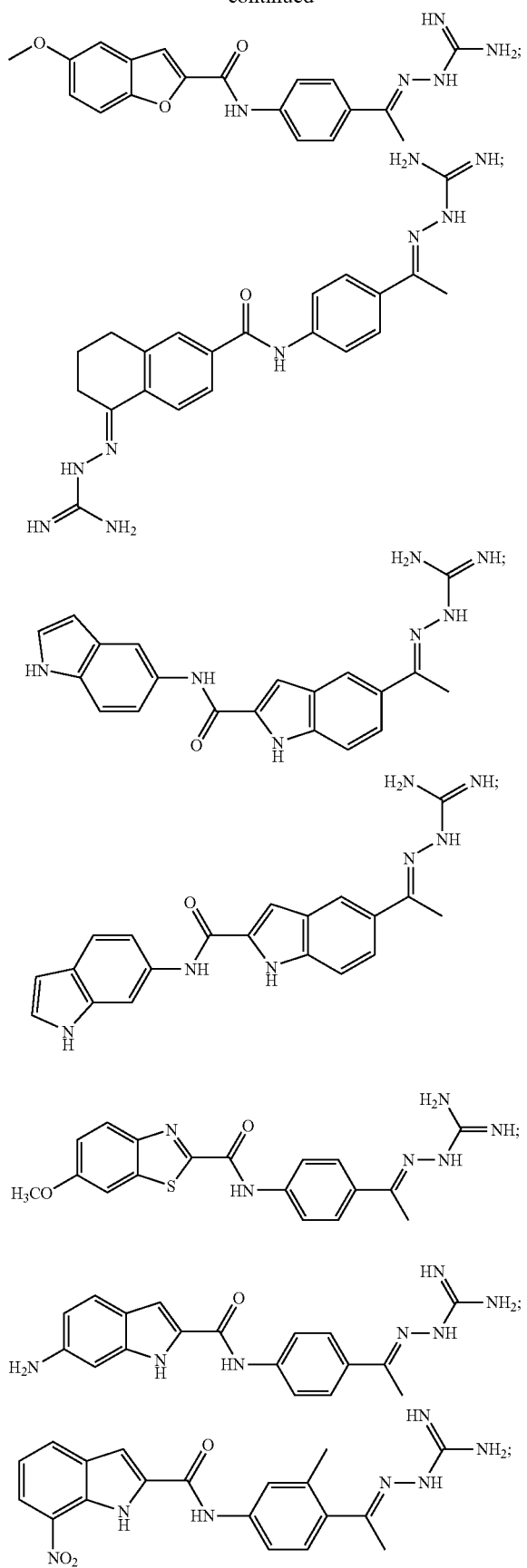
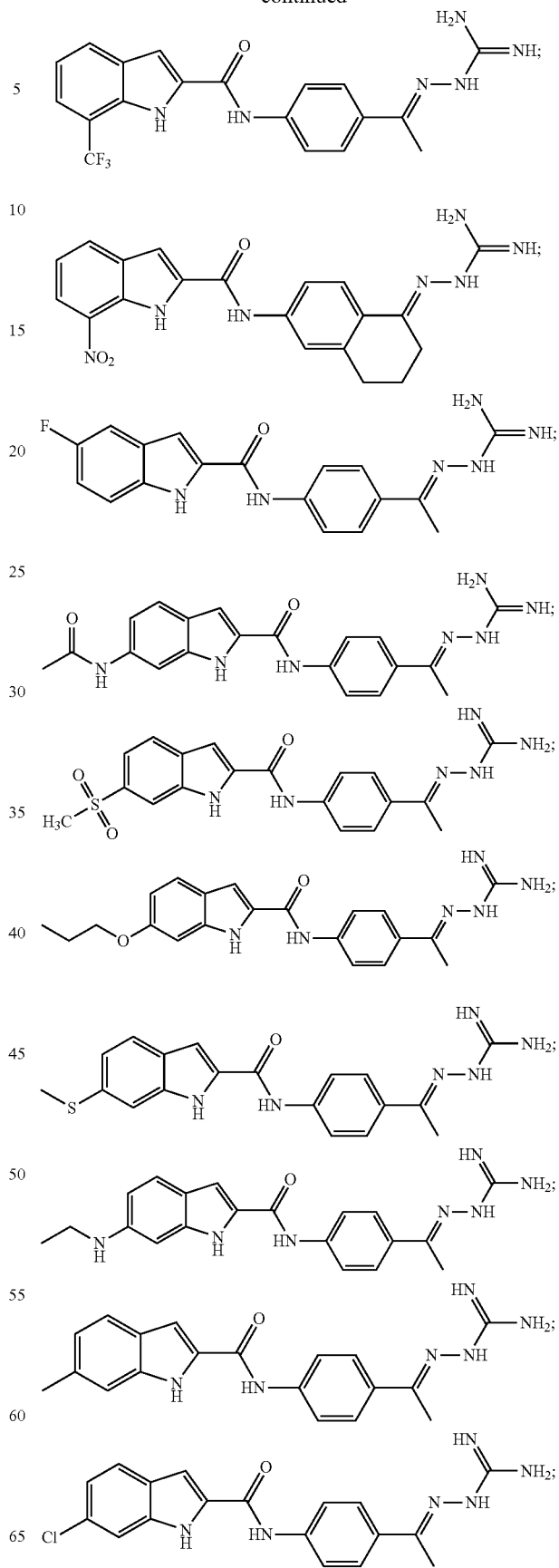

131
-continued

132
-continued

133
-continued
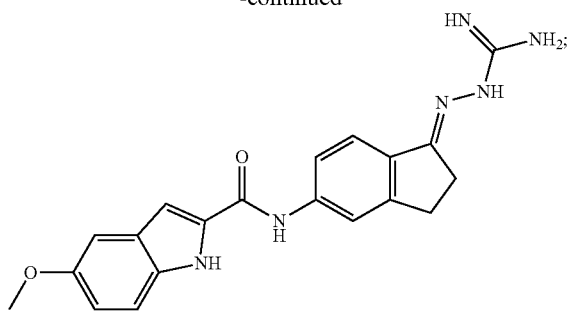
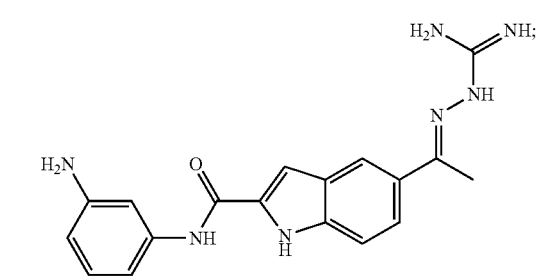
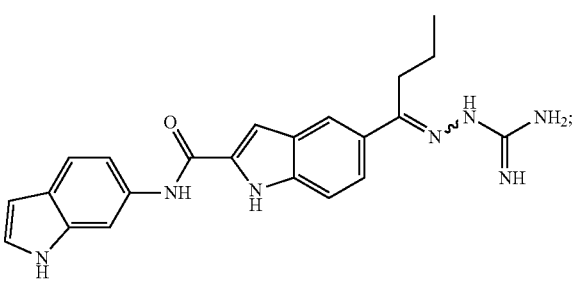
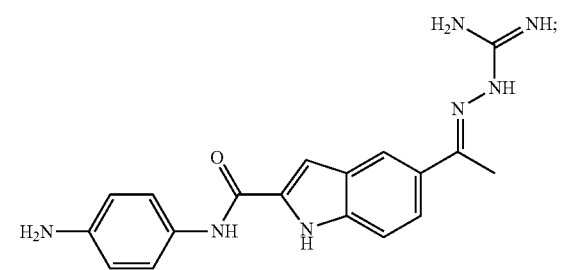
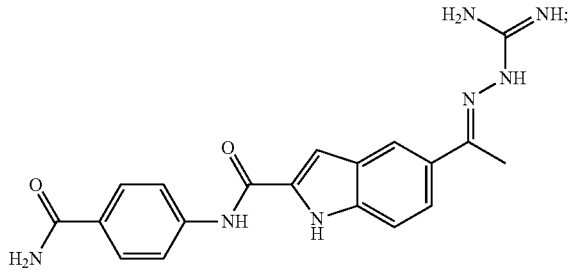
134
-continued
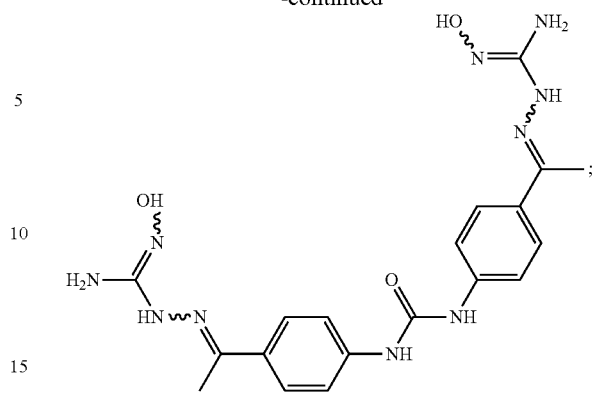
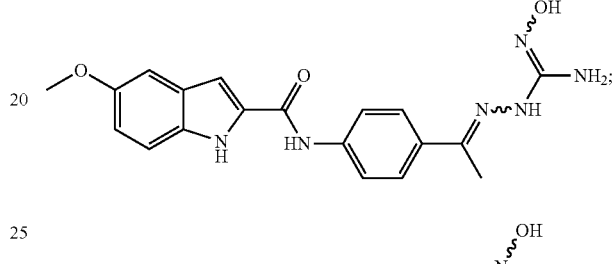
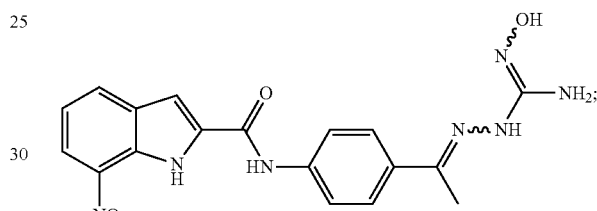
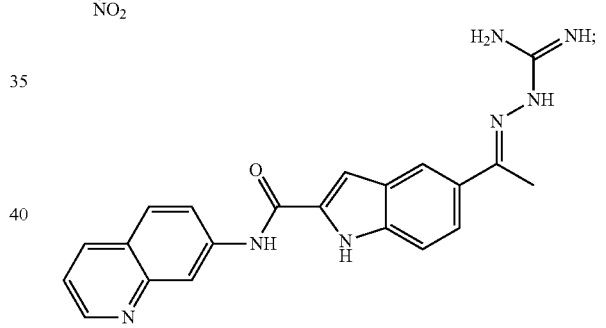
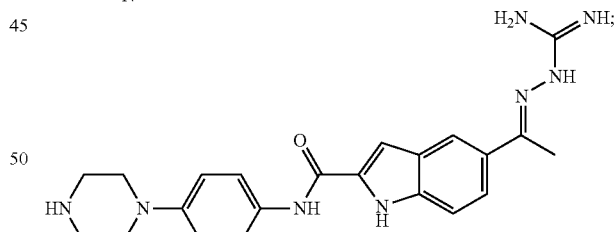
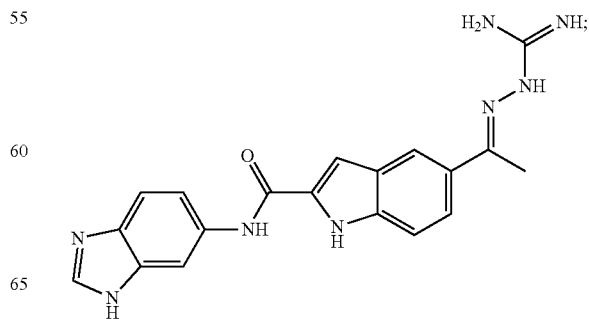

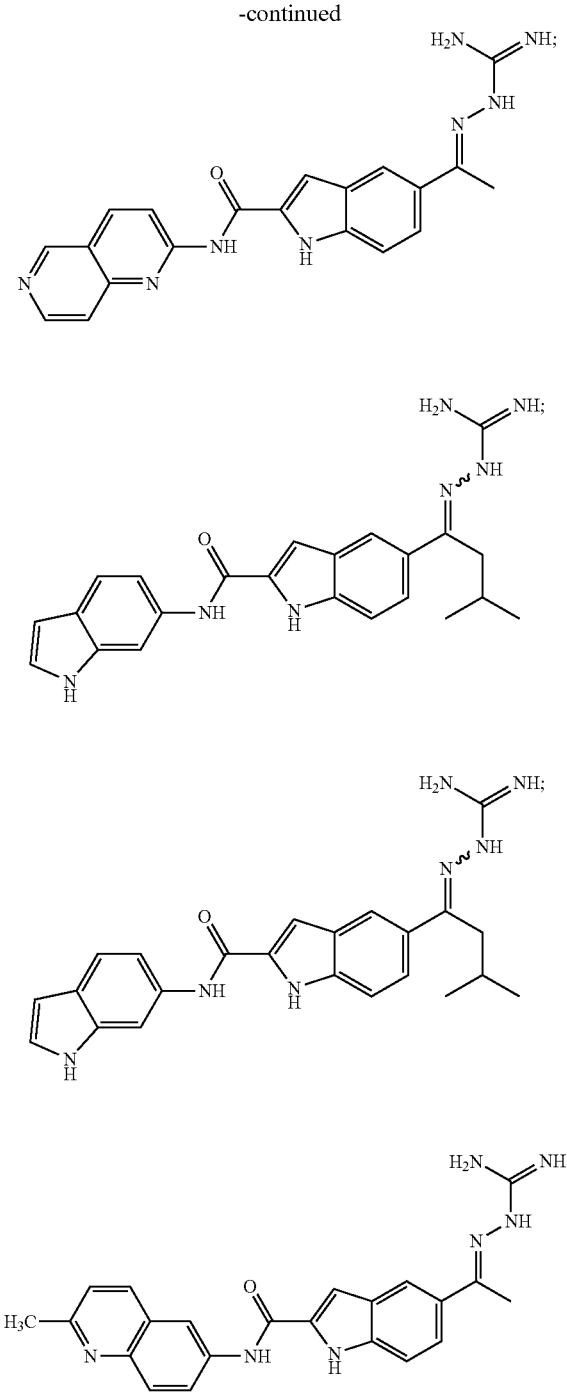
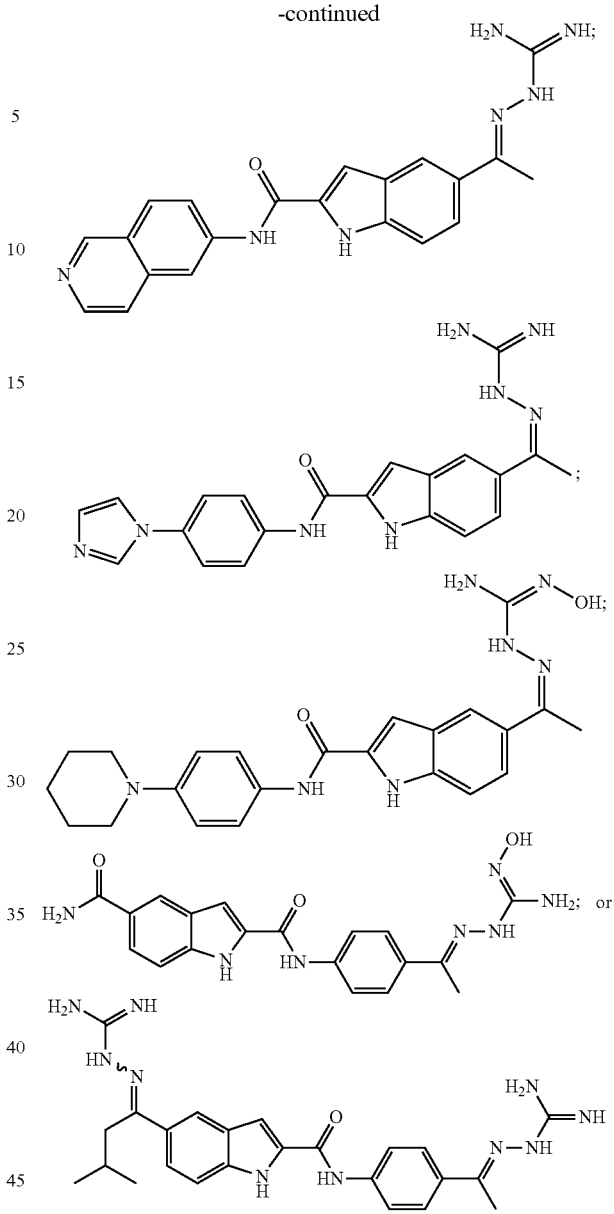
or a pharmaceutically acceptable salt or stereoisomer thereof.
3. A pharmaceutical composition comprising a compound of claim 2 and a pharmaceutically acceptable carrier, excipient or diluent.
* * * * *